(12) United States Patent
Andrews et al.

(10) Patent No.: US 6,329,400 B1
(45) Date of Patent: Dec. 11, 2001

(54) FORMAMIDE COMPOUNDS AS THERAPEUTIC AGENTS

(75) Inventors: Robert Carl Andrews, Durham; Marc Werner Andersen, Raleigh; Dulce Garrido Bubacz, Cary; Joseph Howing Chan, Chapel Hill; David John Cowan, Hillsborough; Michael David Gaul, Apex; Daryl Lynn McDougald, Durham; David Lee Musso, Raleigh; Michael Howard Rabinowitz, Durham; Jennifer Badiang Stanford, Cary; Robert William Wiethe, Durham, all of NC (US)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 09/382,924

(22) Filed: Aug. 25, 1999

Related U.S. Application Data

(60) Provisional application No. 60/097,958, filed on Aug. 26, 1998.

(30) Foreign Application Priority Data

Aug. 26, 1998 (GB) .................................................. 9818608

(51) Int. Cl.[7] ...................... C07D 409/12; C07D 213/74; A61K 31/4436; A61K 31/4409
(52) U.S. Cl. ...................... 514/336; 514/352; 546/281.4; 546/309
(58) Field of Search .................................. 514/336, 337, 514/338, 352; 546/271.7, 281.1, 281.4, 282.4, 284.1, 283.4, 309

(56) References Cited

U.S. PATENT DOCUMENTS

| | | |
|---|---|---|
| 4,996,358 | 2/1991 | Handa et al. .......................... 562/621 |
| 5,239,078 | 8/1993 | Galardy et al. ....................... 546/201 |
| 5,691,382 | 11/1997 | Crimmin et al. ..................... 514/575 |
| 5,747,514 | 5/1998 | Beckett et al. ........................ 514/352 |

FOREIGN PATENT DOCUMENTS

| | | |
|---|---|---|
| 0 082 088 A1 | 12/1982 | (EP) . |
| 0 236 872 A2 | 2/1987 | (EP) . |
| 92/09556 | 6/1992 | (WO) . |
| 92/09563 | 6/1992 | (WO) . |
| 93/00327 | 1/1993 | (WO) . |
| 93/13741 | 7/1993 | (WO) . |
| 93/21942 | 11/1993 | (WO) . |
| 94/07527 | 4/1994 | (WO) . |
| 94/10990 | 5/1994 | (WO) . |
| 94/22309 | 10/1994 | (WO) . |
| 95/04735 | 2/1995 | (WO) . |
| 95/06031 | 3/1995 | (WO) . |
| 95/12603 | 5/1995 | (WO) . |
| 95/19956 | 7/1995 | (WO) . |
| 95/19965 | 7/1995 | (WO) . |
| 95/22966 | 8/1995 | (WO) . |
| 95/32944 | 12/1995 | (WO) . |
| 95/33709 | 12/1995 | (WO) . |
| WO 96/16027 * | 5/1996 | (WO) . |
| 96/16027 | 5/1996 | (WO) . |
| 96/20918 | 7/1996 | (WO) . |
| 97/03783 | 2/1997 | (WO) . |
| WO 97/03783 * | 2/1997 | (WO) . |
| 97/19053 | 5/1997 | (WO) . |
| 98/17643 | 4/1998 | (WO) . |

OTHER PUBLICATIONS

Akiyama, M. et al., "N–Hydroxy Amides, Part 5.+Synthesis and Properties of N–Hydroxypeptides having Leucine Enkephalin Sequences", Journ. Chem Soc., Perkin Trans. 1, (1986) pp. 851–855.

Akiyama, M. et al., "Synthesis and Properties of Enkephalin Analogues Containing An N–Hydroxyamino Acid", Pept. Chem. (1985) 22:271–6.

Berner, I., et al., "Chiral Linear Hydroxamates as Biomimetic Analoguesof ferrioxamine and coprogen and their use in probing siderophore–receptor specifity in bacteria and fungi", Biol. Met. (1991) 4(3): 186–91.

Devlin, J., et al., "Studies Concerning the Antibiotic Actinonin. Part III. Synthesis of Structural analogues of actinonin by the Anhydride–Imide Method" J. Chem Soc. Perkin Trans. 1 (1975) 9:857–860.

Castelhano, et al., Chemical Abstracts, vol. 125, Abst. 143320, (1996).

Zaluski, et al., "New Bidentates as Full Inhibitors of Enkephalin–Degrading Enzymes: Synthesis and Analgesic Properties", J. Med. Chem Soc. Perkin 1 (1975) 9:830–41.

Floyd, et al., Chemical Abstracts, vol. 126, Abst. 212449, (1997).

* cited by examiner

Primary Examiner—Mukund J. Shah
Assistant Examiner—Deepak R. Rao
(74) Attorney, Agent, or Firm—John L. Lemanowicz

(57) ABSTRACT

A family of compounds having the general structural formula

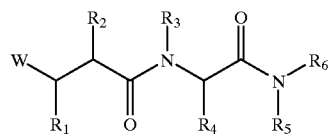

where W is a reverse hydroxamic acid group, and $R_1$, $R_2$, $R_3$, $R_4$, $R_5$ and $R_6$ are as described in the specification, or a pharmaceutically acceptable salt, solvate, biohydrolyzable ester, biohydrolyzable amide, affinity reagent, or prodrug thereof.

7 Claims, No Drawings

FORMAMIDE COMPOUNDS AS THERAPEUTIC AGENTS

This application claims priority from U.S. Provisional application 60/097,958 filed Aug. 26, 1998 and GB9818608.3, also filed Aug. 26, 1998.

FIELD OF THE INVENTION

The present invention provides novel compounds, novel compositions, methods of their use and methods of their manufacture, such compounds generally pharmacologically useful as agents in those disease states alleviated by the inhibition or antagonism of matrix metalloproteases, metalloproteases, and/or tumor necrosis factor-alpha (TNF), which pathologically involve aberrant extracellular matrix degradation, shedding of cell surface protein ectodomains, and/or TNF synthesis, such disease states including arthritis, tumor metastasis and diabetes. The aforementioned pharmacologic activities are useful in the treatment of mammals.

More specifically, the compounds of the present invention can be used in the treatment of rheumatoid arthritis, osteoarthritis, inflammatory bowel syndromes, periodontal disease, aberrant angiogenesis, tumor invasion and metastasis, corneal ulceration and the complications of diabetes. At the present time, there is a need in the areas of rheumatology, oncology, dentistry, opththalmology, gastroenterology, cardiology, neurology, nephrology, infectious disease and endocrinology therapy for such agents.

BACKGROUND OF THE INVENTION

The matrix metalloprotease (MMP) family of zinc endoproteases includes fibroblast collagenase (MMP-1, collagenase-1), neutrophil collagenase (MMP-8, collagenase-2), chondrocyte collagenase (MMP-13, collagenase-3), gelatinases A and B (MMP's 2 and 9), and members of the stromelysin family such as stromelysin-1 (MMP-3), stromelysin-3 (MMP-11), and matrilysin (MMP-7). These enzymes accelerate breakdown of connective tissue by catalyzed resorption of the extracellular matrix. This is a feature of diverse pathologies; therefore, inhibitors of one or more of the matrix metalloproteases would have utility in a wide range of disease states such as in abrogating the initiation of tumor metastasis and angiogenesis and in halting the pathogenesis of demyelinating diseases of the nervous system, multiple sclerosis being one example. MMP inhibitors would also find utility in diseases involving connective tissue degradation in the joint, as occurs in osteoarthritis and rheumatoid arthritis. MMP's-1 and -3 have been found in elevated levels in the synovial fluid of patients with rheumatoid arthritis and osteoarthritis.

Collagenase-3 (MMP-13) is a member of the family of MMP's which preferentially digest collagen. Collagenase-3 is one of the more newly characterized MMP's; biochemical studies on the recombinant protein have demonstrated that it cleaves type II collagen, the predominant matrix component of articular cartilage, more efficiently than either MMP-1 or MMP-2 and that it is expressed by chondrocytes in osteoarthritic cartilage. These data would implicate collagenase-3 as a significant target in rheumatoid arthritis and osteoarthritis for inhibition by MMP inhibitors.

Compounds which inhibit the activities of one or more of the matrix metalloproteases are recognized as having therapeutic benefit in one or more pathologies where MMP activity is upregulated, such as;

i) inflammatory/autoimmune diseases, including but not limited to rheumatoid arthritis, osteoarthritis, Crohn's disease and other inflammatory bowel diseases, periodontal disease, gingivitis, and corneal ulceration;

ii) cardiovascular diseases, including but not limited to atherosclerosis, and restenosis;

iii) metabolic diseases, including but not limited to complications of diabetes, osteoporosis, and other disorders involving resorption of bone;

iv) neurologic diseases, including but not limited to multiple sclerosis and other demyelination ailments;

v) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof;

vi) renal diseases, including but not limited to nephrotic syndromes and glomerulonephritis;

vii) infectious diseases, including but not limited to those mediated by viruses, bacteria, and fungi; and viii) respiratory diseases, including but not limited to emphysema and COPD.

Many inhibitors of matrix metalloproteases have been disclosed, including some structure activity relationships for a series of carboxylalylamine inhibitors. These molecules are exemplary for MMP inhibitors in general. They generally embody a functional group capable of tightly binding the zinc cofactor at the enzyme active site, which is contained within a peptidic or pseudopeptide structure. Zinc binding groups among the MMP inhibitor art have included hydroxamic acid, reverse hydroxamic acid, thiol, carboxylate, and phosphinate.

Hydroxamate metalloprotease inhibitors disclosed in the art usually have the following general structure (I):

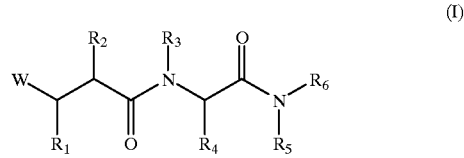

(I)

where W is a zinc-chelating acyl derivative group of the formula —C(O)NHOH (which by convention and in this application are referred to as "forward hydroxamates") or a zinc-chelating substituted amine group of the formula —NH(OH)C(O)R (which by convention and in this application are referred to as "reverse hydroxamates"), where R is usually hydrogen or alkyl. The other substituents vary according to specifications expressed by the art disclosure. It is understood and demonstrated that variations in these substituents can have dramatic effects on potency and selectivities between the matrix metalloproteases.

Suppression of MMP activity in conditions characterized by its overproduction would be of benefit, and compounds which inhibit MMP's would act in this manner at a specific target and be useful and of benefit. The present invention fills this need by providing compounds that are potetn, specific, orally active inhibitors of matrix metalloproteases.

Tumor necrosis factor-α (TNFα), hereinafter called "TNF", is a mammalian protein capable of inducing cellular effects by virtue of its interaction with specific cellular receptors. It was initially characterized and so named due to its ability to cause death of cancerous cells. It is produced primarily by activated monocytes and macrophages. Human TNF is produced as a larger pro-form of 26 kD which is processed to a secreted 17 kD) mature form by proteolytic processing of the alanine-76-valine-77 peptide bond.

Recently, certain compounds having matrix metalloprotease-inhibiting activity have been found to inhibit the release of mature 17 kD TNF from cells. Further, these inhibitors also protect mice from a lethal dose of endotoxin indicating that the compounds can inhibit TNF secretion in vivo. These compounds inhibit the cell-associated proteolytic processing of the 26 kD pro-TNF to the mature 17 kD form. The proteolytic activity is thought to reside in an intracellular or cell-associated specific enzyme or family of enzymes, which by convention is called a "TNF convertase", distinct from the matrix metalloproteases but related in that both contain a zinc cation at the active site. TNF convertase enzymatic activity can be detected in monocyte membrane fractions, and the enzyme activity can be inhibited by certain matrix metalloprotease-inhibiting compounds.

A metalloprotease is thought to mediate the proteolysis of the cell-surface IgE receptor CD23. Certain of the CD23-derived peptides possess biological activitites mimicking those of cytokines, including TNFα.

Metalloprotease-like activity is also thought to contribute to the shedding of certain cell surface protein ectodomains such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II.

TNF is known to mediate many biological responses in vivo. Preclinical and clinical studies in animals and humans with specific TNF neutralizing antibodies, soluble TNF receptor constructs, and TNF detection techniques have implicated TNF as a mediator in numerous pathologies. The compounds of the present invention by virtue of their activity in inhibiting TNF production and/or their activity in preventing cell surface protein ectodomain shedding should show utility in the treatment of diverse pathologies such as;

i) inflammatory/autoimmune diseases, including but not limited to rheumatoid arthritis, osteoarthritis, Crohn's disease and other inflammatory bowel diseases and inflammatory gastrointestinal diseases, and systemic lupus erythematosis;

ii) reperfusion injuries, such as those caused by an initial ischemic event;

iii) systemic inflammatory response syndromes, including but not limited to sepsis, burn injury, pancreatitis, and adult respiratory distress syndrome;

iv) allergic and dermatologic diseases, including but not limited to delayed type hypersensitivity, psoriasis, asthma, eczema, allergic rhinitis, and allergic conjunctivitis;

v) cardiovascular diseases, including but not limited to hyperlipidemia, myocardial infarction. atherosclerosis, chronic obstructive pulmonary disease, and restenosis;

vi) metabolic diseases, including but not limited to osteoporosis, obesity, and diabetes;

vii) neurologic diseases, including but not limited to Alzheimer's disease, Parkinson's disease, multiple sclerosis, aneurism, and stroke;

viii) transplant rejection, including but not limited to organ transplant rejection and graft versus host disease;

ix) diseases of cancer and malignancy, including but not limited to cancers of the oral cavity and pharynx (lip, tongue, mouth, pharynx), esophagus, stomach, small intestine, large intestine, rectum, liver and biliary passages, pancreas, larynx, lung, bone, connective tissue, skin, colon, breast, cervix uteri, corpus endometrium, ovary, prostate, testis, bladder, kidney and other urinary tissues, eye, brain and central nervous system, thyroid and other endocrine gland, leukemias (lymphocytic, granulocytic, monocytic), Hodgkin's disease, non-Hodgkin's lymphomas, multiple myeloma, tumor invasion, and metastatic and angiogenic events thereof, x) renal diseases, including but not limited to nephrotic syndromes and glomerulonephritis;

xi) cachexia and related wasting syndromes;

xii) infectious diseases, including but not limited to HIV infection and neuropathy, Epstein-Barr viral infection, herpes viral infection, malaria, meningitis, schistosomiasis, leprosy, hepatitis (which includes hepatitis A, hepatitis B, and hepatitis C), infectious arthritis, leishmaniasis, tuberculosis, Lyme disease, and viral encephalitis;

xiii) effects of disease therapy, including but not limited to cytokine therapy, chemotherapy, radiation therapy and therapies using anti-T-cell antibodies or cytotoxin-antibody conjugates; and xiv) ocular diseases, including but not limited to diabetic retinopathy and macular degeneration.

Suppression of TNF activity in conditions characterized by its overproduction would be of benefit, and compounds which inhibit TNF convertase would act in this manner at a specific target and be useful and of benefit. The present invention fulfills this need by providing potent, specific, orally active inhibitors of TNF-alpha release from monocyte cells acting via inhibition of TNF-alpha converting enzyme (TNFc).

Suppression of shedding of cell surface protein ectodomains in conditions characterized by an overactivity of such a shedding enzyme or enzymes would be of benefit, and compounds which inhibit this cell surface protein ectodomain shedding would be useful and of benefit. The present invention fulfills this need by providing potent, orally active inhibitors of shedding of cell surface protein ectodomains acting via inhibition of one or more specific enzymes which mediate this proteolytic event.

Suppression of CD23 proteolysis in conditions characterized by an overabundance of CD23 proteolytic fragments would be of benefit, and compounds which inhibit CD23 proteolysis would be useful and of benefit. The present invention fills this need by providing potent inhibitors of CD23 proteolysis acting via inhibition of one or more specific enzymes which mediate this proteolytic event.

SUMMARY OF THE INVENTION

Accordingly it is an object of the present invention to provide a potent, specific, orally active inhibitor of matrix metalloproteases.

It is another object of the present invention to provide a potent, specific, orally active inhibitor of TNF-alpha release from monocyte cells acting via inhibition of TNF-alpha converting enzyme (TNFc).

Accordingly it is another object of the present invention to provide a potent, orally active inhibitor of shedding of cell surface protein ectodomains acting via inhibition of one or more specific enzymes which mediate this proteolytic event.

Accordingly it is another object of the present invention to provide a potent inhibitor of CD23 proteolysis acting via inhibition of one or more specific enzymes which mediate this proteolytic event.

It is an object, therefore, of the present invention to provide a compound of the formula

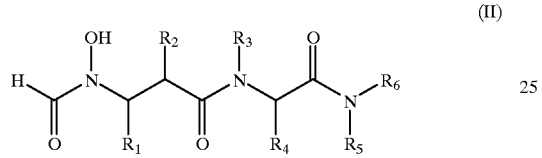

(II)

where $R_1$ is

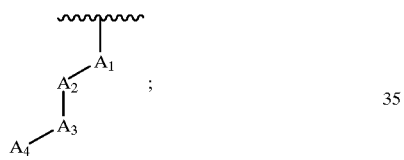

where $A_1$ is alkylene, alkenylene, alkynylene, cycloalkylene, cycloalkenylene, arylene, heterocyclylene, heteroarylene, or a direct bond;

$A_2$ is $C(O)NR_7$, $NR_7C(O)$, $SO_2NR_7$, $NR_7SO_2$, $NR_7$, S, SO, $SO_2$, O, or a direct bond, where $R_7$ is as defined below;

$A_3$ is alkylene, alkenylene, alkynylene, cycloalkylene, cycloalkenylene, arylene, heterocyclylene, heteroarylene, or a direct bond;

$A_4$ is alkyl, alkenyl, alkynyl, cycloalkyl, cycloalkenyl, heterocyclyl, heteroaryl, aryl, $NR_8R_9$, $OR_8$, or hydrogen, where $R_8$ and $R_9$ are as defined below;

$R_2$ is

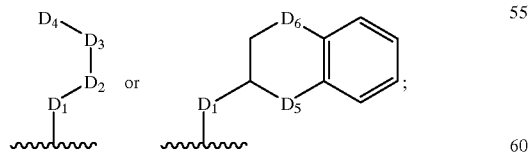

where $D_1$ is alkylene, alkenylene, alkynylene, $NR_{10}(O)C$, $NR_{10}$, S, SO, $SO_2$, O, or a direct bond, where $R_{10}$ is as defined below;

$D_2$ is S, SO, $SO_2$, O, $C(O)NR_{11}$, $NR_{11}C(O)$, $NR_{11}$, or a direct bond, where $R_{11}$ is as defined below;

$D_3$ isalkylene, alkenylene, alkynylene, arylene, heteroarylene, S, SO, $SO_2$, O, $C(O)NR_{12}$, $NR_{12}C(O)$, $SO_2NR_{12}$, $NR_{12}SO_2$, $NR_{12}$, or a direct bond, where $R_{12}$ is as defined below;

$D_4$ is aryl, aryloxy, heteroaryl, or heteroaryloxy;

$D_5$ and $D_6$ are, independently, lower alkylene, O, S, SO, or $SO_2$;

$R_3$ is hydrogen or lower alkyl;

$R_4$ is

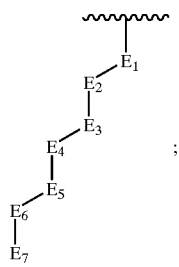

where $E_1$ is alkylene, alkenylene, alkynylene, cycloalkylene, cycloalkenylene, arylene, heterocyclylene, heteroarylene, $C(O)NR_{13}$, or a direct bond, where $R_{13}$ is as defined below;

$E_2$ is alkylene, alkenylene, alkynylene, cycloalkylene, cycloalkenylene, arylene, heterocyclylene, heteroarylene, $NR_{14}$, S, SO, $SO_2$, O, $C(O)$, or a direct bond, where $R_4$ is as defined below;

$E_3$ is alkylene, alkenylene, alkynylene, cycloalkylene, cycloalkenylene, arylene, heterocyclylene, heteroarylene, $NR_{15}$, S, SO, $SO_2$, O, $C(O)$,

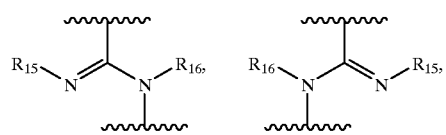

or a direct bond, where $R_{15}$ and $R_{16}$ are as defined below;

$E_4$ is alkylene, alkenylene, alkynylene, cycloalkylene, cycloalkenylene, arylene, heterocyclylene, heteroarylene, $NR_{18}$, S, SO, $SO_2$, O, $N(R_{18})C(O)$, $C(O)N(R_{18})$, $C(O)$,

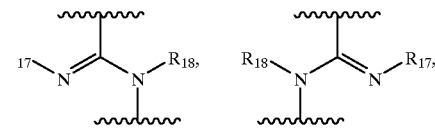

or a direct bond, where $R_{17}$ and $R_{18}$ are as defined below;

$E_5$ is alkylene, alkenylene, alkynylene, cycloalkylene, cycloalkenylene, arylene, heterocyclylene, heteroarylene, $NR_9$, S, SO, $SO_2$, O, $C(O)$,

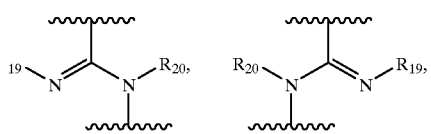

or a direct bond, where $R_{19}$ and $R_{20}$ are as defined below;

$E_6$ is alkylene, alkenylene, alkynylene, cycloalkylene, cycloalkenylene, arylene, heterocyclylene, heteroarylene, $NR_{21}$, S, SO, $SO_2$, O, C(O), or a direct bond, where $R_{21}$ is as defined below;

$E_7$ is hydrogen, $NR_{22}R_{23}$, $OR_{22}$, $SR_{22}$, $SOR_{22}$, $SO_2R_{22}$, alkyl, alkenyl, alkynyl, cycloalkyl, cycloalkenyl, heterocyclyl, aryl, or heteroaryl, where $R_{22}$ and $R_{23}$ are as defined below;

$R_5$ is hydrogen or lower alkyl;

$R_6$ is

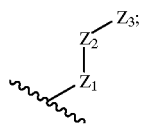

where $Z_1$ is heteroarylene;

$Z_2$ is lower alkylene, lower alkenylene, lower alkynylene, cycloalkylene, cycloalkenylene, arylene, heterocyclylene, heteroarylene, $C(O)NR_{24}$, $NR_{24}C(O)$, $SO_2NR_{24}$, $NR_{24}SO2$, $NR_{24}$, S, SO, $SO_2$, O, C(O), C(O)O, OC(O), or a direct bond, where $R_{24}$ is as defined below;

$Z_3$ is alkyl, alkenyl, alkynyl, cycloalkyl, cycloalkenyl, heterocyclyl, heteroaryl, aryl, $NR_{25}R_{26}$, $OR_{25}$, or hydrogen, where $R_{25}$ and $R_{26}$ are as defined below; and $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, and $R_{26}$ are, independently, hydrogen, alkyl, alkynyl, alkenyl, cycloalkyl, cycloalkenyl, aryl, heterocyclyl, or heteroaryl;

or a pharmaceutically acceptable salt, solvate, biohydrolyzable ester, biohydrolyzable amide, affinity reagent, or prodrug thereof.

DETAILED DESCRIPTION OF THE INVENTION

The present invention provides a family of compounds having the general structural formula:

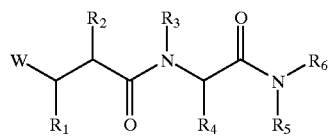

(I)

or a pharmaceutically acceptable salt, solvate, biohydrolyzable esters, biohydrolyzable amides, affinity reagents, or prodrugs thereof, wherein W is a reverse hydroxamic acid group;

$R_1$ is a substituent other than hydrogen;

$R_4$ is a lipophilic substituent preferably with steric bulk proximal to the peptide backbone, and;

$R_6$ is a heteroaryl substituent.

Such compounds are novel and are unknown in the art and, given the appropriate choice of $R_1$, $R_2$, $R_3$, $R_4$, $R_5$, and $R_6$, as described herein, show potent inhibition of MMP's, cell-free TNF convertase enzyme and TNF release from cells, and in some cases inhibit TNF convertase and TNF release from cells in preference to matrix metalloproteases. The heteroaryl nature of $R_6$ in combination with an appropriate choice of $R_1$, $R_2$, $R_3$, $R_4$, and $R_5$ as described herein is beneficial in achieving increased potency against TNF release from cells relative to inhibition of MMP's. Such molecules can be selective for TNF inhibition over MMP's and can possess an improved therapeutic profile where inhibition of one or more of the matrix metalloproteases is associated with an adverse biological response or abnormal pathology. The heteroaryl nature of $R_6$ in combination with an appropriate choice of $R_1$, $R_2$, $R_3$, $R_4$, and $R_5$ as described herein is also beneficial in achieving selective inhibition of one or more of the matrix metalloproteases (for example, collagenase-3) in preference to TNF convertase inhibition and inhibition of TNF release from whole cells.

In particular, a preferred group of compounds of the present invention include those of the formula (II):

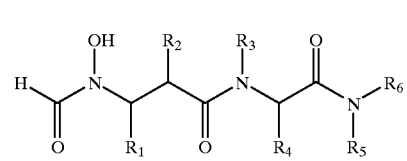

(II)

where $R_1$ is

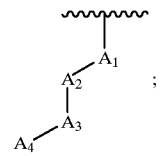

where $A_1$ is alkylene, alkenylene, alkynylene, cycloalkylene, cycloalkenylene, arylene, heterocyclylene, heteroarylene, or a direct bond;

$A_2$ is $C(O)NR_7$, $NR_7C(O)$, $SO_2NR_7$, $NR_7SO_2$, $NR_7$, S, SO, $SO_2$, O, or a direct bond, where $R_7$ is as defined below;

$A_3$ is alkylene, alkenylene, alkynylene, cycloalkylene, cycloalkenylene, arylene, heterocyclylene, heteroarylene, or a direct bond;

$A_4$ is alkyl, alkenyl, alkynyl, cycloalkyl, cycloalkenyl, heterocyclyl, heteroaryl, aryl, $NR_8R_9$, $OR_8$, or hydrogen, where $R_8$ and $R_9$ are as defined below;

$R_2$ is

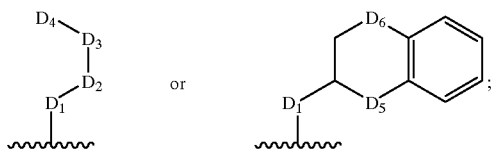

where $D_1$ is alkylene, alkenylene, alkynylene, $NR_{10}(O)C$, $NR_{10}$, S, SO, $SO_2$, O, or a direct bond, where $R_{10}$ is as defined below;

$D_2$ is S, SO, $SO_2$, O, $C(O)NR_{11}$, $NR_{11}C(O)$, $NR_{11}$, or a direct bond, where $R_{11}$ is as defined below;

$D_3$ is alkylene, alkenylene, alkynylene, cycloalkylene, arylene, heteroarylene, S, SO, $SO_2$, O, $C(O)NR_{12}$, $NR_{12}C(O)$, $SO_2NR_{12}$, $NR_{12}SO_2$, $NR_{12}$, or a direct bond, where $R_{12}$ is as defined below;

$D_4$ is aryl, aryloxy, heteroaryl, or heteroaryloxy;

$D_5$ and $D_6$ are, independently, lower alkylene, O, S, SO, or $SO_2$;

$R_3$ is hydrogen or lower alkyl;

$R_4$ is

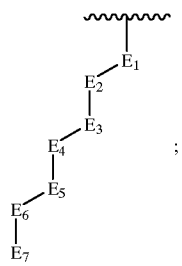

where $E_1$ is alkylene, alkenylene, alkynylene, cycloalkylene, cycloalkenylene, arylene, heterocyclylene, heteroarylene, $C(O)NR_{13}$, or a direct bond, where $R_{13}$ is as defined below;

$E_2$ is alkylene, alkenylene, alkynylene, cycloalkylene, cycloalkenylene, arylene, heterocyclylene, heteroarylene, $NR_{14}$, S, SO, $SO_2$, O, $C(O)$, or a direct bond, where $R_{14}$ is as defined below;

$E_3$ is alkylene, alkenylene, alkynylene, cycloalkyene, cycloalkenylene, arylene, heterocyclylene, heteroaryene, $NR_{15}$, S, SO, $SO_2$, O, $C(O)$,

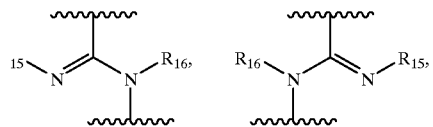

or a direct bond, where $R_{15}$ and $R_{16}$ are as defined below;

$E_4$ is alkylene, alkenylene, alkynylene, cycloalkylene, cycloalkenylene, arylene, heterocyclylene, heteroarylene, $NR_{18}$, S, SO, $SO_2$, O, $N(R_{18})C(O)$, $C(O)N(R_{18})$, $C(O)$,

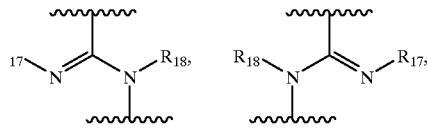

or a direct bond, where $R_{17}$ and $R_{18}$ are as defined below;

$E_5$ is alkylene, alkenylene, alkynylene, cycloalkylene, cycloalkenylene, arylene, heterocyclylene, heteroarylene, $NR_{19}$, S, SO, $SO_2$, O, $C(O)$,

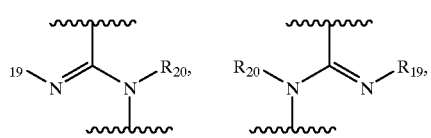

or a direct bond, where $R_{19}$ and $R_{20}$ are as defined below;

$E_6$ is alkylene, alkenylene, alkynylene, cycloalkylene, cycloalkenylene, arylene, heterocyclylene, heteroarylene, $NR_{21}$, S, SO, $SO_2$, O, $C(O)$, or a direct bond, where $R_{21}$ is as defined below;

$E_7$ is hydrogen, $NR_{22}R_{23}$, $OR_{22}$, $SR_{22}$, $SOR_{22}$, $SO_2R_{22}$, alkyl, alkenyl, alkynyl, cycloalkyl, cycloalkenyl, heterocyclyl, aryl, or heteroaryl, where $R_{22}$ and $R_{23}$ are as defined below;

$R_5$ is hydrogen or lower alkyl;

$R_6$ is

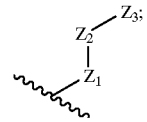

where $Z_1$ is heteroarylene;

$Z_2$ is lower alkylene, lower alkenylene, lower alkynylene, cycloalkylene, cycloalkenylene, arylene, heterocyclylene, heteroarylene, $C(O)NR_{24}$, $NR_{24}C(O)$, $SO_2NR_{24}$, $NR_{24}SO_2$, $NR_{24}$, S, SO, $SO_2$, O, $C(O)$, $OC(O)$, $C(O)O$, or a direct bond, where $R_{24}$ is as defined below;

$Z_3$ is alkyl, alkenyl, alkynyl, cycloalkyl, cycloalkenyl, heterocyclyl, heteroaryl, aryl, $NR_{25}R_{26}$, $OR_{25}$, or hydrogen, where $R_{25}$ and $R_{26}$ are as defined below;

$R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$ are, independently, hydrogen, alkyl, alkynyl, alkenyl, cycloalkyl, aryl, heterocyclyl, or heteroaryl;

or a pharmnaceutically acceptable salt, solvate, biohydrolyzable ester, biohydrolyzable amide, affinity reagent, or prodrug thereof.

Compounds of the present invention which are currently preferred for their high biological activity are listed below in Tables 1A and 1B; variables below are with reference to the generic structure (I).

TABLE IA

| Example | W | $R_1$ | $R_2$ | $R_3$ | $R_4$ | $R_5$ | $R_6$ |
|---|---|---|---|---|---|---|---|
| 1 | HO-N(H)-C(=O)H | methyl | 3-phenylpropyl | H | tert-butyl | H | pyridin-3-yl |
| 2 | HO-N(H)-C(=O)H | methyl | (4-phenylcyclohexyl)methyl | H | tert-butyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 3 | N-hydroxyformamide | propyl | 3-phenylpropyl | H | 4-(benzyloxycarbonylamino)butyl | H | 1,3,4-thiadiazol-2-yl |
| 4 | N-hydroxyformamide | propyl | 3-(furan-3-yl)propyl | H | 4-(benzyloxycarbonylamino)butyl | H | thiazol-2-yl |

TABLE IA-continued
| Example | W | R₁ | R₂ | R₃ | R₄ | R₅ | R₆ |
|---|---|---|---|---|---|---|---|
| 5 | 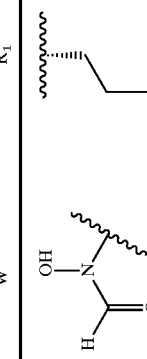 | 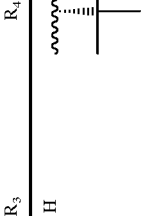 | 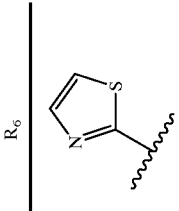 | H | 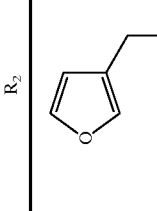 | H | 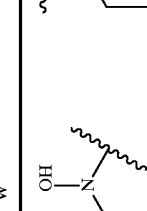 |
| 6 | 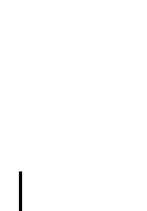 | 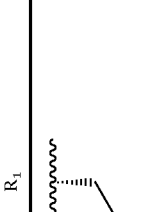 | 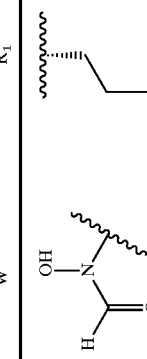 | H | 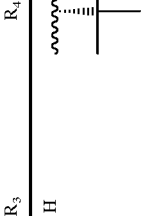 | H | 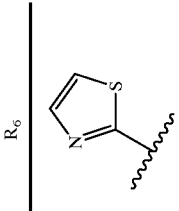 |

TABLE IA-continued
| Example | W | R1 | R2 | R3 | R4 | R5 | R6 |
|---|---|---|---|---|---|---|---|
| 7 | 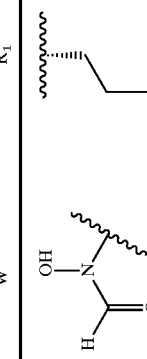 | 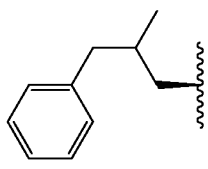 | 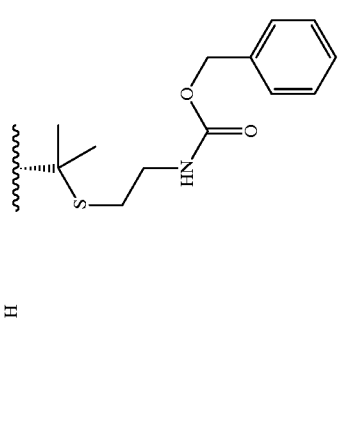 | H | 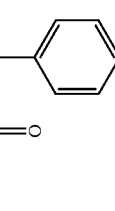 | H | 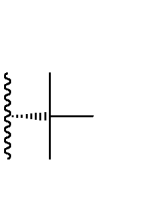 |
| 8 | 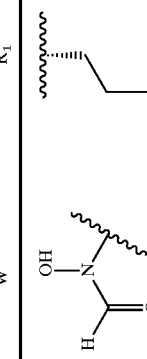 | 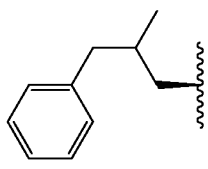 | 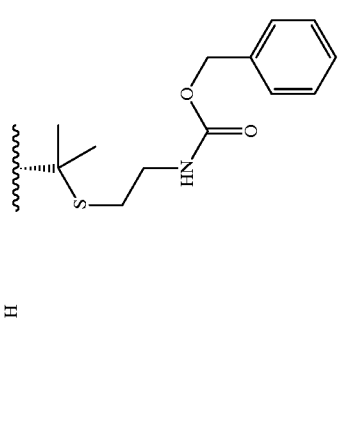 | H |  | H | 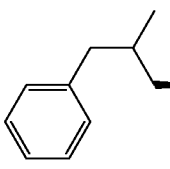 |

TABLE IA-continued

| Example | W | $R_1$ | $R_2$ | $R_3$ | $R_4$ | $R_5$ | $R_6$ |
|---|---|---|---|---|---|---|---|
| 9 | N(OH)CHO | propyl | isobutyl-benzyl | H | -(CH2)4-NHC(O)OCH2Ph | H | thiazol-2-yl |
| 10 | N(OH)CHO | ethyl | benzothiophen-2-ylmethyl | H | tert-butyl | H | thiazol-2-yl |
| 11 | N(OH)CHO | methyl | 3-phenylpropyl | H | tert-butyl | H | pyridin-2-yl |

TABLE IA-continued

| Example | W | $R_1$ | $R_2$ | $R_3$ | $R_4$ | $R_5$ | $R_6$ |
|---|---|---|---|---|---|---|---|
| 12 | N(OH)CHO | methyl | 3-phenylpropyl | H | 3-pyridylmethyl | H | 2-pyridyl |
| 13 | N(OH)CHO | methyl | 3-phenylpropyl | H | 4-(benzyloxycarbonylamino)butyl | H | 2-pyridyl |

TABLE IA-continued

| Example | W | R1 | R2 | R3 | R4 | R5 | R6 |
|---------|---|----|----|----|----|----|----|
| 14 | HC(O)N(OH)– | –CH3 | 3-phenylpropyl | H | –(CH2)4–NHC(O)CH2-(2-naphthyl) | H | 2-pyridyl |
| 15 | HC(O)N(OH)– | –CH3 | 3-phenylpropyl | H | –(CH2)4–NHC(O)O–CH2-phenyl | H | 2-thiazolyl |

TABLE IA-continued

| Example | W | $R_1$ | $R_2$ | $R_3$ | $R_4$ | $R_5$ | $R_6$ |
|---|---|---|---|---|---|---|---|
| 16 | N-OH, CHO | methyl | benzyloxypropyl | H | propyl-NH-C(O)-O-benzyl | H | thiazol-2-yl |
| 17 | N-OH, CHO | methyl | phenylpropyl | H | propyl-NH-C(O)-NH$_2$ | H | pyridin-2-yl |
| 18 | N-OH, CHO | isopentyl | phenylpropyl | H | sec-butyl | H | pyridin-2-yl |

TABLE IA-continued
| Example | W | R1 | R2 | R3 | R4 | R5 | R6 |
|---|---|---|---|---|---|---|---|
| 19 | 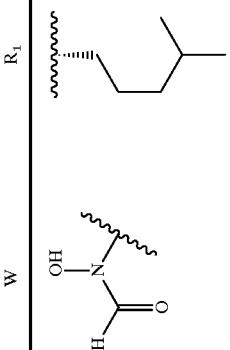 | 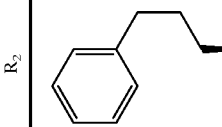 |  | H | 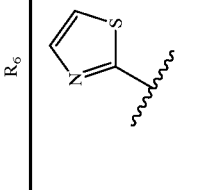 | H | 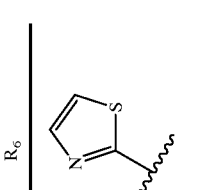 |
| 20 | 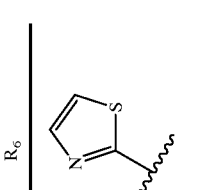 | 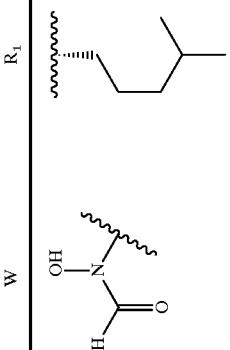 | 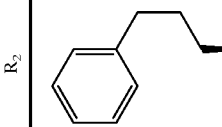 | H |  | H | 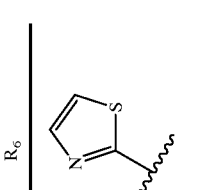 |

TABLE IA-continued
| Example | W | $R_1$ | $R_2$ | $R_3$ | $R_4$ | $R_5$ | $R_6$ |
|---|---|---|---|---|---|---|---|
| 21 | 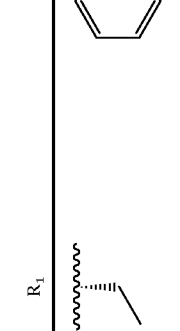 | 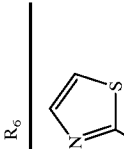 | 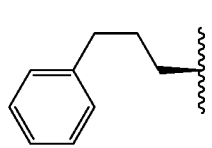 | H |  | H | 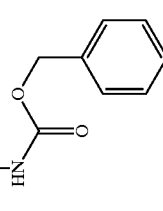 |
| 22 |  | 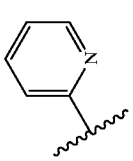 | 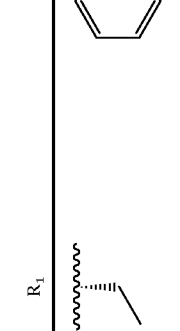 | H | 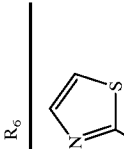 | H | 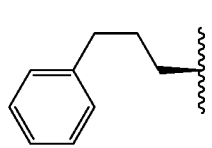 |
| 23 |  | 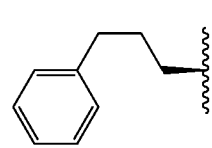 |  | H | 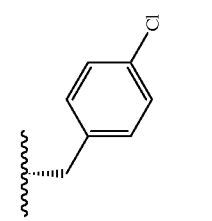 | H | 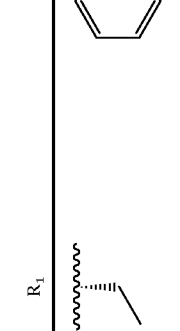 |

TABLE IA-continued

| Example | W | $R_1$ | $R_2$ | $R_3$ | $R_4$ | $R_5$ | $R_6$ |
|---|---|---|---|---|---|---|---|
| 24 | HO-N(H)-C(=O)- | methyl | 3-phenylpropyl | H | 4-fluorobenzyl | H | 2-pyridyl |
| 25 | HO-N(H)-C(=O)- | isopentyl | 3-phenylpropyl | H | 3-(N'-(2,3,6-trimethyl-4-methoxyphenylsulfonyl)guanidino)propyl | H | 2-thiazolyl |

TABLE IA-continued

| Example | W | $R_1$ | $R_2$ | $R_3$ | $R_4$ | $R_5$ | $R_6$ |
|---|---|---|---|---|---|---|---|
| 26 | N(OH)CHO | propyl | phenylpropyl | H | tert-butyl | H | thiazol-2-yl |
| 27 | N(OH)CHO | methyl | phenylpropyl | H | tert-butyl | H | thiazol-2-yl |
| 28 | N(OH)CHO | ethyl | phenylpropyl | H | (benzyloxycarbonylamino)propyl | H | pyridin-2-yl |

TABLE IA-continued

| Example | W | $R_1$ | $R_2$ | $R_3$ | $R_4$ | $R_5$ | $R_6$ |
|---|---|---|---|---|---|---|---|
| 29 | N(OH)CHO | methyl (wedge) | 3-phenylpropyl | H | 4-(benzyloxycarbonylamino)butyl | H | pyridin-2-yl |
| 30 | N(OH)CHO | methyl (wedge) | 3-phenylpropyl | H | 4-(benzyloxycarbonylamino)phenylmethyl | H | pyridin-2-yl |

TABLE IA-continued
| Example | W | $R_1$ | $R_2$ | $R_3$ | $R_4$ | $R_5$ | $R_6$ |
|---|---|---|---|---|---|---|---|
| 31 | 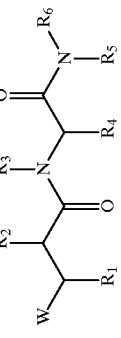 | 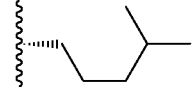 | 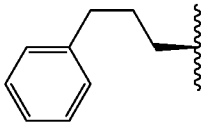 | H | 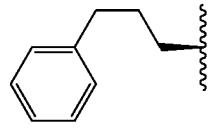 | H |  |
| 32 | 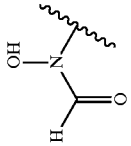 | 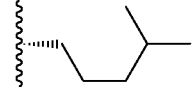 | 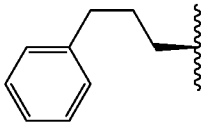 | H | 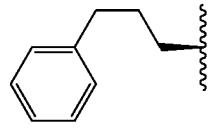 | H | 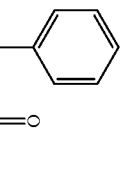 |

TABLE IA-continued

| Example | W | $R_1$ | $R_2$ | $R_3$ | $R_4$ | $R_5$ | $R_6$ |
|---|---|---|---|---|---|---|---|
| 33 | HN(OH)CHO | methyl | 2-methyl-3-phenylpropyl | H | 4-(benzyloxycarbonylamino)butyl | H | 2-pyridyl |
| 34 | HN(OH)CHO | methyl | 3-phenylpropyl | H | isopropyl | H | 2-pyridyl |
| 35 | HN(OH)CHO | methyl | 2-methyl-3-phenylpropyl | H | sec-butyl | H | 2-pyridyl |

TABLE IA-continued

| Example | W | $R_1$ | $R_2$ | $R_3$ | $R_4$ | $R_5$ | $R_6$ |
|---------|---|-------|-------|-------|-------|-------|-------|
| 36 | N(OH)CHO | propyl | phenylpropyl | H | cyclohexyl | H | 2-pyridyl |
| 37 | N(OH)CHO | methyl | phenylpropyl | H | 3-pyridylmethyl | H | 2-pyridyl |
| 38 | N(OH)CHO | methyl | 2-methyl-3-phenylpropyl | H | tert-butyl | H | 2-pyridyl |

TABLE IA-continued

| Example | W | R$_1$ | R$_2$ | R$_3$ | R$_4$ | R$_5$ | R$_6$ |
|---|---|---|---|---|---|---|---|
| 39 | N(OH)CHO | n-propyl | 3-phenylpropyl | H | (CH$_2$)$_3$NHC(=NH)NHSO$_2$-(2,4,6-trimethyl-3-methoxyphenyl) | H | 2-thiazolyl |
| 40 | N(OH)CHO | CH$_2$CH$_2$CF$_3$ | 3-phenylpropyl | H | tert-butyl | H | 2-pyridyl |

TABLE IA-continued

| Example | W | $R_1$ | $R_2$ | $R_3$ | $R_4$ | $R_5$ | $R_6$ |
|---|---|---|---|---|---|---|---|
| 41 | N(OH)CHO | methyl | 3-phenylpropyl | H | cyclohexyl | H | 2-pyridyl |
| 42 | N(OH)CHO | methyl | 3-phenylpropyl | H | tert-butyl | H | 2-thiazolyl |
| 43 | N(OH)CHO | methyl | 2-phenylethyl | H | tert-butyl | H | 2-thiazolyl |

TABLE IA-continued

| Example | W | $R_1$ | $R_2$ | $R_3$ | $R_4$ | $R_5$ | $R_6$ |
|---|---|---|---|---|---|---|---|
| 44 | OH-N-CHO | ⋮ | phenylpropyl | H | (CH₂)₄NHC(O)O-CH₂-cyclopentyl | H | thiazolyl |
| 45 | OH-N-CHO | ⋮ | phenylpropyl | H | (CH₂)₄NHC(O)O-CH₂-cyclopentyl | H | pyridyl |

TABLE IA-continued
| Example | W | R$_1$ | R$_2$ | R$_3$ | R$_4$ | R$_5$ | R$_6$ |
|---|---|---|---|---|---|---|---|
| 46 | 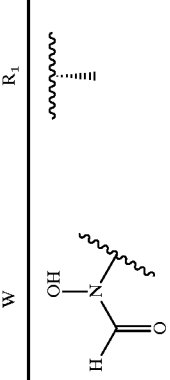 |  | 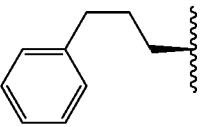 | H | 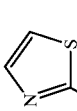 | H | 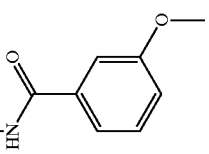 |
| 47 | 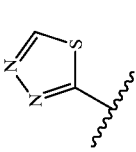 | 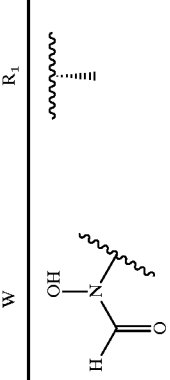 |  | H | 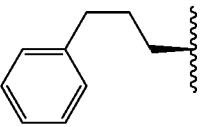 | H | 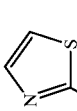 |

TABLE IA-continued

| Example | W | $R_1$ | $R_2$ | $R_3$ | $R_4$ | $R_5$ | $R_6$ |
|---|---|---|---|---|---|---|---|
| 48 | N(OH)CHO | propyl | 3-furyl-propyl | H | -(CH$_2$)$_4$-NH-C(O)-O-CH$_2$-phenyl | H | thiazol-2-yl |
| 49 | N(OH)CHO | propyl | 3-pyridyl-propyl | H | -(CH$_2$)$_4$-NH-C(O)-O-CH$_2$-phenyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 50 | N(OH)CHO | propyl | 3-phenylpropyl | H | 4-(benzyloxycarbonylamino)butyl | H | 5-methylisoxazol-3-yl |
| 51 | N(OH)CHO | propyl | 2-methyl-3-phenylpropyl | H | tert-butyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 52 | N(OH)CHO | propyl | benzyloxyethyl | H | (CH2)4NHC(O)OCH2Ph | H | thiazol-2-yl |
| 53 | N(OH)CHO | propyl | benzyloxymethyl | H | (CH2)4NHC(O)OCH2Ph | H | thiazol-2-yl |

TABLE IA-continued

| Example | W | $R_1$ | $R_2$ | $R_3$ | $R_4$ | $R_5$ | $R_6$ |
|---------|---|-------|-------|-------|-------|-------|-------|
| 54 | N(OH)CHO | methyl | 2-methyl-3-phenylpropyl | H | (CH$_2$)$_4$NHC(O)OCH$_2$Ph | H | thiazol-2-yl |
| 55 | N(OH)CHO | methyl | 2-methyl-3-phenylpropyl | H | tert-butyl | H | thiazol-2-yl |

TABLE IA-continued
| Example | W | $R_1$ | $R_2$ | $R_3$ | $R_4$ | $R_5$ | $R_6$ |
|---|---|---|---|---|---|---|---|
| 56 | 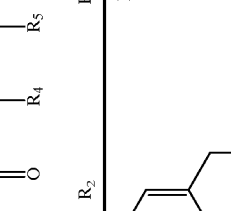 | 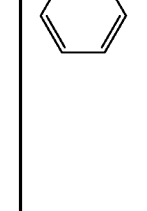 |  | H |  | H |  |
| 57 | 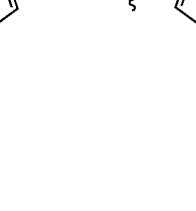 | 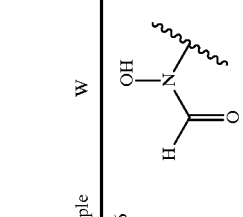 |  | H |  | H |  |
| 58 |  |  |  | H | 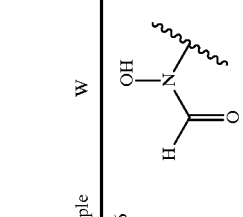 | H |  |

TABLE IA-continued

| Example | W | $R_1$ | $R_2$ | $R_3$ | $R_4$ | $R_5$ | $R_6$ |
|---|---|---|---|---|---|---|---|
| 59 | N(OH)CHO | propyl | benzofuran-2-ylmethyl | H | tert-butyl | H | thiazol-2-yl |
| 60 | N(OH)CHO | propyl | benzofuran-2-ylmethyl | H | -(CH$_2$)$_3$-NH-C(=O)-O-CH$_2$-phenyl | H | pyridin-2-yl |

TABLE IA-continued
| Example | W | $R_1$ | $R_2$ | $R_3$ | $R_4$ | $R_5$ | $R_6$ |
|---------|---|-------|-------|-------|-------|-------|-------|
| 61 | 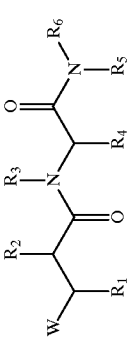 |  |  | H | 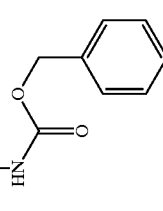 | H | 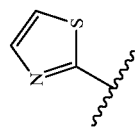 |
| 62 | 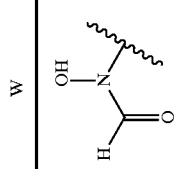 | 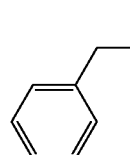 | 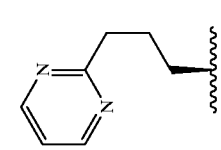 | H | 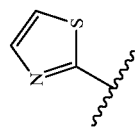 | H | 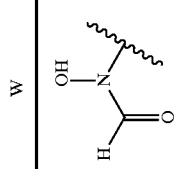 |
| 63 | 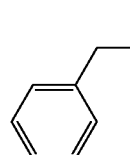 | 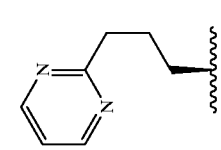 | 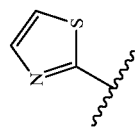 | H | t-Bu | H | thiazole |

TABLE IA-continued
| Example | W | $R_1$ | $R_2$ | $R_3$ | $R_4$ | $R_5$ | $R_6$ |
|---|---|---|---|---|---|---|---|
| 64 | 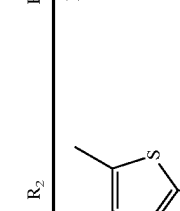 | 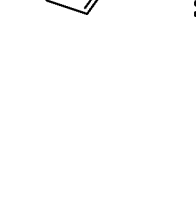 | 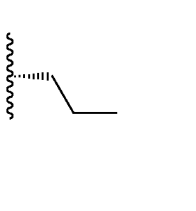 | H | 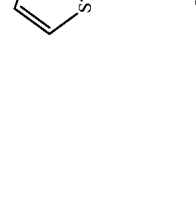 | H | 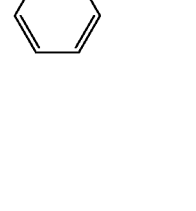 |
| 65 | 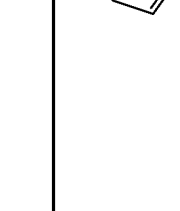 | 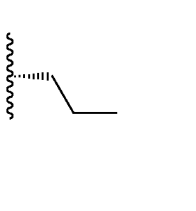 | 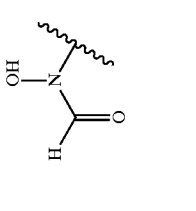 | H | 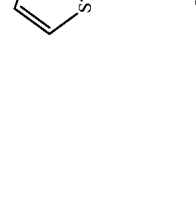 | H | 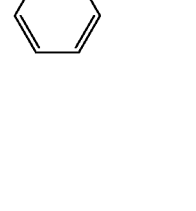 |
| 66 | 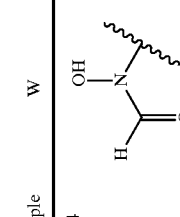 |  |  | H |  | H |  |

TABLE IA-continued

| Example | W | $R_1$ | $R_2$ | $R_3$ | $R_4$ | $R_5$ | $R_6$ |
|---|---|---|---|---|---|---|---|
| 67 | OH-N-CHO | CH$_2$-S-(2-thienyl) | benzyl-CH(CH$_3$)-CH$_2$- | H | t-Bu | H | thiazol-2-yl |
| 68 | OH-N-CHO | CH$_2$-(1,2,4-triazol-1-yl) | benzyl-CH(CH$_3$)-CH$_2$- | H | t-Bu | H | thiazol-2-yl |
| 69 | OH-N-CHO | n-propyl | 3-(furan-3-yl)propyl | H | t-Bu | H | thiazol-5-yl |

TABLE IA-continued

| Example | W | $R_1$ | $R_2$ | $R_3$ | $R_4$ | $R_5$ | $R_6$ |
|---|---|---|---|---|---|---|---|
| 70 | N(OH)CHO | 2-(pyridin-2-yl)ethyl | 2-methyl-3-phenylpropyl | H | t-Bu | H | thiazol-2-yl |
| 71 | N(OH)CHO | 2-(furan-3-yl)ethyl | 2-methyl-3-phenylpropyl | H | t-Bu | H | thiazol-2-yl |
| 72 | N(OH)CHO | 2-(thiazol-2-yl)ethyl | 2-methyl-3-phenylpropyl | H | t-Bu | H | thiazol-2-yl |

TABLE IA-continued
| Example | W | $R_1$ | $R_2$ | $R_3$ | $R_4$ | $R_5$ | $R_6$ |
|---------|---|-------|-------|-------|-------|-------|-------|
| 73 | 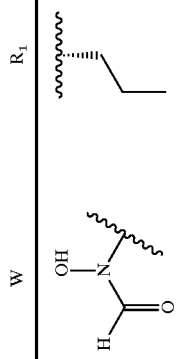 | 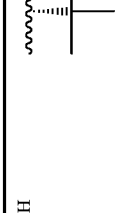 | 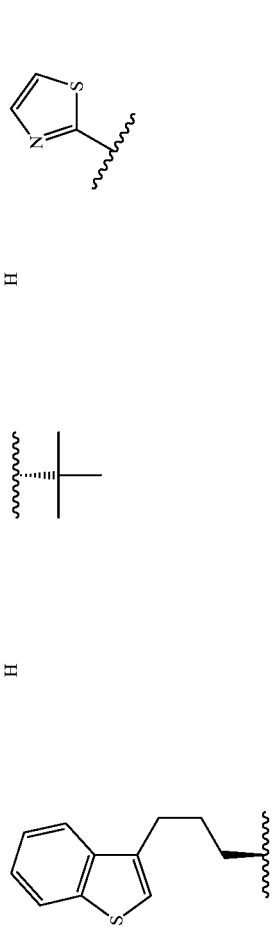 (benzothiophene) | H | 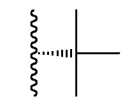 (t-Bu) | H | 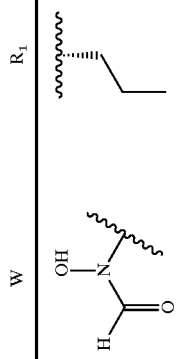 (thiazole) |
| 74 | 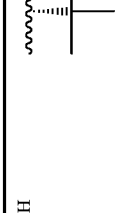 | 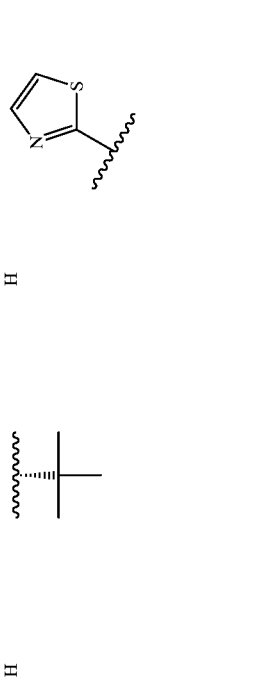 | 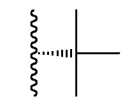 (benzofuran) | H | 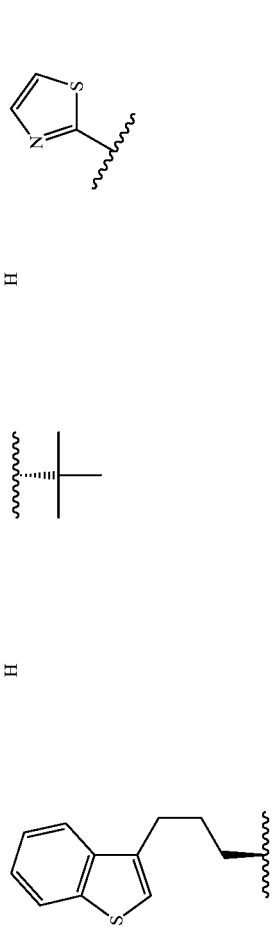 (t-Bu) | H | 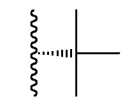 (thiazole) |

TABLE IA-continued

| Example | W | $R_1$ | $R_2$ | $R_3$ | $R_4$ | $R_5$ | $R_6$ |
|---|---|---|---|---|---|---|---|
| 75 | N(OH)CHO | ethyl | benzothiophen-2-ylmethyl | H | (CH$_2$)$_4$NHC(O)OCH$_2$Ph | H | thiazol-2-yl |
| 76 | N(OH)CHO | ethyl | benzothiophen-2-ylmethyl | H | (CH$_2$)$_4$NHC(O)OEt | H | pyridin-2-yl |
| 77 | N(OH)CHO | ethyl | cinnamyl | H | tert-butyl | H | 1,3,4-thiadiazol-2-yl |

TABLE IA-continued

| Example | W | R$_1$ | R$_2$ | R$_3$ | R$_4$ | R$_5$ | R$_6$ |
|---|---|---|---|---|---|---|---|
| 78 | N(OH)CHO | methyl (dashed) | phenyl-(CH$_2$)$_3$- | H | tert-butyl | H | 1,3,4-thiadiazol-2-yl |
| 79 | N(OH)CHO | ethyl | thiophen-2-yl-(CH$_2$)$_3$- | H | tert-butyl | H | 1,3,4-thiadiazol-2-yl |
| 80 | N(OH)CHO | ethyl | pyridin-2-yl-(CH$_2$)$_3$- | H | tert-butyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 81 | N(OH)CHO | propyl | thiophen-2-ylmethyl | H | (CH2)4NHC(O)OCH2Ph | H | thiazol-2-yl |
| 82 | N(OH)CHO | ethyl | furan-2-ylmethyl | H | (CH2)4NHC(O)OCH2Ph | H | thiazol-2-yl |

TABLE IA-continued

| Example | W | R₁ | R₂ | R₃ | R₄ | R₅ | R₆ |
|---------|---|----|----|----|----|----|----|
| 83 | N(OH)CHO | propyl | 4-fluorobenzyl | H | tert-butyl | H | thiazol-2-yl |
| 84 | N(OH)CHO | ethyl | benzothiophen-2-ylmethyl | H | C(CH₃)₂SCH₂CH₂NHC(O)OEt | H | thiazol-2-yl |
| 85 | N(OH)CHO | propyl | furan-2-ylmethyl | H | tert-butyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 86 | N(OH)CHO | ethyl | benzothiophen-2-ylmethyl | H | -(CH$_2$)$_4$-NH-C(O)-O-ethyl | H | thiazol-2-yl |
| 87 | N(OH)CHO | propyl | (5-methylthiophen-2-yl)methyl | H | tert-butyl | H | thiazol-2-yl |
| 88 | N(OH)CHO | methyl | -(CH$_2$)$_3$-O-CH$_2$-phenyl | H | -(CH$_2$)$_2$-NH-C(O)-O-CH$_2$-phenyl | H | pyridin-2-yl |

TABLE IA-continued

| Example | W | $R_1$ | $R_2$ | $R_3$ | $R_4$ | $R_5$ | $R_6$ |
|---------|---|-------|-------|-------|-------|-------|-------|
| 89 | N(OH)CHO | methyl | tetrahydronaphthalen-2-ylmethyl | H | -(CH$_2$)$_4$NHC(O)OCH$_2$Ph | H | pyridin-2-yl |
| 90 | N(OH)CHO | methyl | 3-phenylbutyl | H | -(CH$_2$)$_4$NHC(O)OCH$_2$Ph | H | pyridin-2-yl |

TABLE IA-continued

| Example | W | $R_1$ | $R_2$ | $R_3$ | $R_4$ | $R_5$ | $R_6$ |
|---------|---|-------|-------|-------|-------|-------|-------|
| 91 | -N(OH)-CHO | methyl | tetrahydronaphthalen-2-ylmethyl | H | sec-butyl | H | pyridin-2-yl |
| 92 | -N(OH)-CHO | propyl | 3-phenylpropyl | H | pyridin-3-ylmethyl | H | thiazol-2-yl |
| 93 | -N(OH)-CHO | methyl | 3-phenylpropyl | H | 2-phenylethyl | H | pyridin-2-yl |

TABLE IA-continued

| Example | W | $R_1$ | $R_2$ | $R_3$ | $R_4$ | $R_5$ | $R_6$ |
|---|---|---|---|---|---|---|---|
| 94 | OH-N-CHO | CH₂CH₂CF₃ | phenylpropyl | H | phenyl | H | thiazolyl |
| 95 | OH-N-CHO | CH₃ | 2-methyl-3-phenylpropyl | H | benzyloxycarbonylaminobutyl | H | pyridyl |
| 96 | OH-N-CHO | CH₃ | tetrahydronaphthalenylmethyl | H | tert-butyl | H | thiazolyl |

TABLE IA-continued

| Example | W | $R_1$ | $R_2$ | $R_3$ | $R_4$ | $R_5$ | $R_6$ |
|---|---|---|---|---|---|---|---|
| 97 | N(OH)CHO | methyl | (4-phenylcyclohexyl)methyl | H | -(CH2)4-NH-C(=O)-O-CH2-phenyl | H | 2-pyridyl |
| 98 | N(OH)CHO | vinyl | (1,2,3,4-tetrahydronaphthalen-2-yl)methyl | H | -(CH2)3-NH-C(=NH)-NH-SO2-(2,4,6-trimethyl-4-methoxyphenyl) | H | 2-thiazolyl |

TABLE IA-continued

| Example | W | R₁ | R₂ | R₃ | R₄ | R₅ | R₆ |
|---|---|---|---|---|---|---|---|
| 99 | OH-N(H)-C(=O)H | vinyl | tetralin-CH₂- | H | tert-butyl | H | thiazole |
| 100 | OH-N(H)-C(=O)H | H | tetralin-CH₂- | H | -(CH₂)₄-NH-C(=O)-O-CH₂-phenyl | H | pyridine |
| 101 | OH-N(H)-C(=O)H | -CH₂-CF₃ | -CH₂CH₂-phenyl | H | isobutyl | H | thiazole |

TABLE IA-continued
| Example | W | $R_1$ | $R_2$ | $R_3$ | $R_4$ | $R_5$ | $R_6$ |
|---|---|---|---|---|---|---|---|
| 102 |  |  |  | H |  | H |  |
| 103 |  |  |  | H |  | H |  |
| 104 |  |  |  | H |  | H |  |

TABLE IA-continued

| Example | W | $R_1$ | $R_2$ | $R_3$ | $R_4$ | $R_5$ | $R_6$ |
|---|---|---|---|---|---|---|---|
| 105 | N(OH)CHO | propyl | 2-naphthylmethyl | H | (CH2)4NHC(O)OCH2Ph | H | 2-pyridyl |
| 106 | N(OH)CHO | propyl | 2-phenyl-butyl | H | (CH2)4NHC(O)OCH2Ph | H | 2-pyridyl |

TABLE IA-continued
| Example | W | $R_1$ | $R_2$ | $R_3$ | $R_4$ | $R_5$ | $R_6$ |
|---|---|---|---|---|---|---|---|
| 107 | 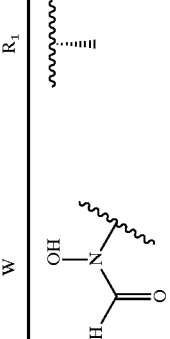 |  | 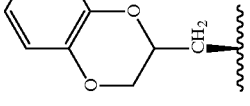 | H | 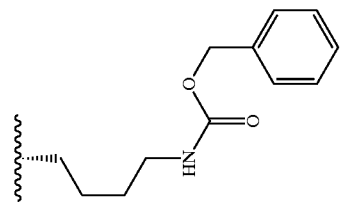 | H |  |
| 108 |  |  | 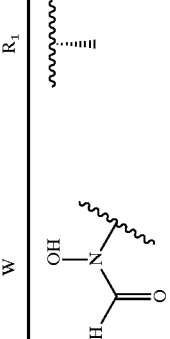 | H |  | H | 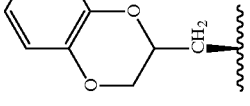 |
| 109 | 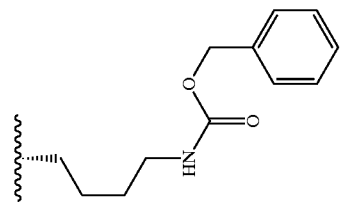 |  |  | H |  | H | 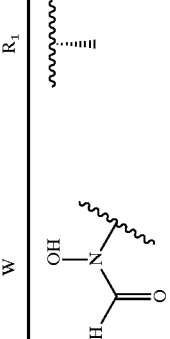 |

TABLE IA-continued

| Example | W | R1 | R2 | R3 | R4 | R5 | R6 |
|---|---|---|---|---|---|---|---|
| 110 | OH-N-CHO | CH2-O-(2-nitrophenyl) | phenyl-CH(CH3)-CH2- | H | -(CH2)3-NH-C(=NH)-NH-SO2-(2,4,6-trimethyl-4-methoxyphenyl) | H | thiazol-2-yl |
| 111 | OH-N-CHO | CH3 | chroman-2-yl-CH2- | H | tert-butyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 112 | HON(OH)CHO | propyl | 3-phenylpropyl | H | t-Bu | H | thiadiazolyl |
| 113 | HON(OH)CHO | thienylethynyl | 2-methyl-3-phenylallyl | H | t-Bu | H | thiazolyl |
| 114 | HON(OH)CHO | 4-(trifluoromethyl)phenethyl | 2-methyl-3-phenylpropyl | H | t-Bu | H | thiazolyl |

TABLE IA-continued

| Example | W | $R_1$ | $R_2$ | $R_3$ | $R_4$ | $R_5$ | $R_6$ |
|---|---|---|---|---|---|---|---|
| 115 | N(OH)CHO | propyl | 3-(thien-2-yl)propyl | H | tert-butyl | H | thiazol-2-yl |
| 116 | N(OH)CHO | propyl | 2-methyl-3-phenylpropyl... (benzyl isobutyl) | H | benzyloxycarbonylaminobutyl | H | thiazol-2-yl |
| 117 | N(OH)CHO | propyl | (thien-2-yl)methyl | H | tert-butyl | H | thiazol-2-yl |

TABLE IA-continued
| Example | W | R1 | R2 | R3 | R4 | R5 | R6 |
|---|---|---|---|---|---|---|---|
| 118 | 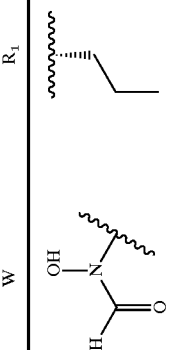 | 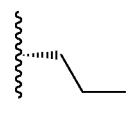 | 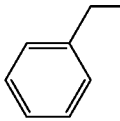 | H |  | H | 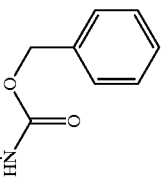 |
| 119 |  | 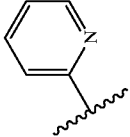 | 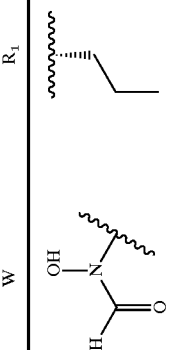 | H |  | H | 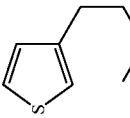 |

TABLE IA-continued

| Example | W | $R_1$ | $R_2$ | $R_3$ | $R_4$ | $R_5$ | $R_6$ |
|---|---|---|---|---|---|---|---|
| 120 | N(OH)CHO | ethyl | benzothiophen-2-ylmethyl | H | (CH2)4NHC(O)OCH2Ph | H | pyridin-2-yl |
| 121 | N(OH)CHO | CH2CF3 | 3-phenylpropyl | H | sec-butyl | H | thiazol-2-yl |
| 122 | N(OH)CHO | CH2CF3 | 3-phenylpropyl | H | 1-hydroxyethyl | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 123 | OH-N-CHO | propyl | 5-methylthiophene-CH₂- | H | -(CH₂)₄-NH-C(O)-O-ethyl | H | 2-pyridyl |
| 124 | OH-N-CHO | propyl | 2-thienyl-(CH₂)₃- | H | -(CH₂)₄-NH-C(O)-O-ethyl | H | 2-pyridyl |
| 125 | OH-N-CHO | propyl | benzoxazol-2-yl-CH₂- | H | -(CH₂)₄-NH-C(O)-O-ethyl | H | 2-pyridyl |

TABLE IA-continued

| Example | W | $R_1$ | $R_2$ | $R_3$ | $R_4$ | $R_5$ | $R_6$ |
|---|---|---|---|---|---|---|---|
| 126 | N-hydroxyformamide | ethyl | benzothiophen-2-ylmethyl | H | -(CH2)4-NH-C(O)-O-ethyl | H | pyridin-2-yl |
| 127 | N-hydroxyformamide | ethyl | benzothiophen-3-ylmethyl | H | -(CH2)4-NH-C(O)-O-ethyl | H | pyridin-2-yl |
| 128 | N-hydroxyformamide | ethyl | benzoxazol-2-ylmethyl | H | tert-butyl | H | pyridin-2-yl |

TABLE IA-continued

| Example | W | R₁ | R₂ | R₃ | R₄ | R₅ | R₆ |
|---|---|---|---|---|---|---|---|
| 129 | N(OH)CHO | ethyl | benzothiophen-2-ylmethyl | H | CH(OMe)CH₃ | H | pyridin-2-yl |
| 130 | N(OH)CHO | propyl | thiophen-3-ylmethyl | H | tert-butyl | H | thiazol-2-yl |
| 131 | N(OH)CHO | propyl | 3-(furan-3-yl)-1-methylpropyl | H | (CH₂)₃NHC(O)OCH₂Ph | H | pyridin-2-yl |

TABLE IA-continued

| Example | W | $R_1$ | $R_2$ | $R_3$ | $R_4$ | $R_5$ | $R_6$ |
|---|---|---|---|---|---|---|---|
| 132 | OH-N(CHO) | propyl | 2-methyl-3-phenylpropyl | H | t-butyl | H | thiadiazolyl |
| 133 | OH-N(CHO) | propyl | (5-methylthien-2-yl)methyl | H | CH(CH$_3$)-OBn | H | thiazolyl |
| 134 | OH-N(CHO) | propyl | (5-methylthien-2-yl)methyl | H | CH(CH$_3$)-OH | H | thiazolyl |

TABLE IA-continued

| Example | W | $R_1$ | $R_2$ | $R_3$ | $R_4$ | $R_5$ | $R_6$ |
|---|---|---|---|---|---|---|---|
| 135 | OH-N-CHO | propyl | phenylpropyl | H | tert-butyl | H | 5-methylthiazol-2-yl |
| 136 | OH-N-CHO | propyl | phenylpropyl | H | tert-butyl | H | pyridin-3-yl |
| 137 | OH-N-CHO | propyl | (5-methylthiophen-2-yl)methyl | H | tert-butyl | H | pyridin-3-yl |

TABLE IA-continued

| Example | W | R₁ | R₂ | R₃ | R₄ | R₅ | R₆ |
|---|---|---|---|---|---|---|---|
| 138 | N(OH)CHO | propyl | 5-methylthiophen-2-ylmethyl | H | t-butyl | H | 3-hydroxypyridin-2-yl |
| 139 | N(OH)CHO | propyl | 3-phenylpropyl | H | t-butyl | H | 2-(ethylthio)-1,3,4-thiadiazol-5-yl |
| 140 | N(OH)CHO | propyl | 5-methylthiophen-2-ylmethyl | H | t-butyl | H | pyridin-4-yl |

TABLE IA-continued

| Example | W | $R_1$ | $R_2$ | $R_3$ | $R_4$ | $R_5$ | $R_6$ |
|---|---|---|---|---|---|---|---|
| 141 | HO-N(H)-CHO | n-propyl | 5-methylthiophen-2-yl-CH₂- | H | tert-butyl | H | thiadiazolyl |
| 142 | HO-N(H)-CHO | n-propyl | 5-methylthiophen-2-yl-CH₂- | H | C(CH₃)₂OH | H | pyridin-2-yl |
| 143 | HO-N(H)-CHO | isopropyl | 3-phenylpropyl | H | tert-butyl | H | thiadiazolyl |

TABLE IA-continued

| Example | W | R₁ | R₂ | R₃ | R₄ | R₅ | R₆ |
|---|---|---|---|---|---|---|---|
| 144 | OH-N-CHO | propyl | 5-methylthiophen-2-ylmethyl | H | C(CH₃)(H)OH | H | pyrazin-2-yl |
| 145 | OH-N-CHO | propyl | 5-methylthiophen-2-ylmethyl | H | C(CH₃)(H)OMe | H | thiazol-2-yl |
| 146 | OH-N-CHO | propyl | 5-methylthiophen-2-ylmethyl | H | C(CH₃)(H)OCH₂(pyridin-2-yl) | H | thiazol-2-yl |

TABLE IA-continued
| Example | W | R1 | R2 | R3 | R4 | R5 | R6 |
|---|---|---|---|---|---|---|---|
| 147 |  | 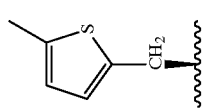 | 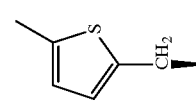 | H | 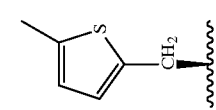 | H | 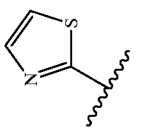 |
| 148 | 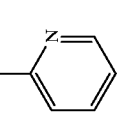 |  | 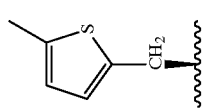 | H | 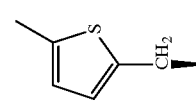 | H | 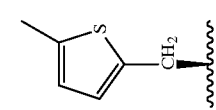 |
| 149 | 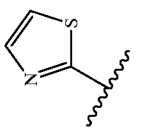 | 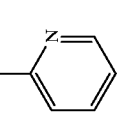 |  | H | 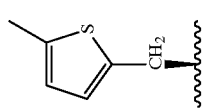 | H | 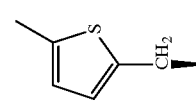 |

TABLE IA-continued

| Example | W | R<sub>1</sub> | R<sub>2</sub> | R<sub>3</sub> | R<sub>4</sub> | R<sub>5</sub> | R<sub>6</sub> |
|---|---|---|---|---|---|---|---|
| 150 | N(OH)CHO | isopropyl | 3-phenylpropyl | H | t-butyl | H | 3-pyridyl |
| 151 | N(OH)CHO | n-propyl | (5-methylthien-2-yl)methyl | H | t-butyl | H | pyrazinyl |
| 152 | N(OH)CHO | n-propyl | (5-methylthien-2-yl)methyl | H | C(CH<sub>3</sub>)<sub>2</sub>OH | H | thiazol-2-yl |

TABLE IA-continued

| Example | W | R₁ | R₂ | R₃ | R₄ | R₅ | R₆ |
|---|---|---|---|---|---|---|---|
| 153 | OH-N-CHO | propyl | 5-methylthiophen-2-ylmethyl | H | CH(CH₃)SCH₃ | H | thiazol-2-yl |
| 154 | OH-N-CHO | propyl | 5-methylthiophen-2-ylmethyl | H | tert-butyl | H | 2-methylthiazol-5-yl |
| 155 | OH-N-CHO | propyl | 5-methylthiophen-2-ylmethyl | H | CH(CH₃)CH₂SO₂N(CH₃)₂ | H | thiazol-2-yl |

TABLE IA-continued

| Example | W | $R_1$ | $R_2$ | $R_3$ | $R_4$ | $R_5$ | $R_6$ |
|---|---|---|---|---|---|---|---|
| 156 | N-hydroxyformamide | n-propyl | 5-methylthiophen-2-ylmethyl | H | CH2C(O)N(CH3)2 | H | pyridin-2-yl |
| 157 | N-hydroxyformamide | n-propyl | 5-methylthiophen-2-ylmethyl | H | tert-butyl | H | 5-methylthiazol-2-yl |
| 158 | N-hydroxyformamide | n-propyl | 5-methylthiophen-2-ylmethyl | H | tert-butyl | H | 6-aminopyridin-3-yl |

TABLE IA-continued

| Example | W | $R_1$ | $R_2$ | $R_3$ | $R_4$ | $R_5$ | $R_6$ |
|---|---|---|---|---|---|---|---|
| 159 | OH-N-CHO | propyl | 5-methylthien-2-ylmethyl | H | sec-butyl | H | thiazol-2-yl |
| 160 | OH-N-CHO | propyl | 5-methylthien-2-ylmethyl | H | -CH2-NH-C(O)-NH2 | H | thiazol-2-yl |
| 161 | OH-N-CHO | propyl | 5-methylthien-2-ylmethyl | H | -C(CH3)(H)-O-CH2-CH(CH3)2 | H | thiazol-2-yl |

TABLE IA-continued

| Example | W | $R_1$ | $R_2$ | $R_3$ | $R_4$ | $R_5$ | $R_6$ |
|---------|---|-------|-------|-------|-------|-------|-------|
| 162 | N(OH)CHO | isopropyl | 2-methyl-3-phenylpropyl | H | tert-butyl | H | thiazol-2-yl |
| 163 | N(OH)CHO | isopropyl | 2-methyl-3-phenylpropyl | H | C(OH)(CH₃) (hydroxyisopropyl) | H | thiazol-2-yl |
| 164 | N(OH)CHO | n-propyl | (5-methylthiophen-2-yl)methyl | H | CH₂NHC(O)CH₃ | H | thiazol-2-yl |

TABLE IA-continued

| Example | W | R₁ | R₂ | R₃ | R₄ | R₅ | R₆ |
|---|---|---|---|---|---|---|---|
| 165 | NHOH-C(=O)- | propyl | 5-methyl-thiophen-2-yl-CH₂- | H | -CH₂-C(=O)-NH-(pyridin-2-yl) | H | thiazol-2-yl |
| 166 | NHOH-C(=O)- | propyl | 5-methyl-thiophen-2-yl-CH₂- | H | -CH₂-CH₂-C(=O)-morpholin-4-yl | H | thiazol-2-yl |
| 167 | NHOH-C(=O)- | propyl | 5-methyl-thiophen-2-yl-CH₂- | H | -CH₂-CH₂-C(=O)-N(CH₃)(CH₂-phenyl) | H | pyridin-2-yl |

TABLE IA-continued

| Example | W | R1 | R2 | R3 | R4 | R5 | R6 |
|---|---|---|---|---|---|---|---|
| 168 | OH-NH-CHO | propyl | 5-methylthiophen-2-yl-CH2 | H | tert-butyl | H | 6-amino-pyridin-2-yl |
| 169 | OH-NH-CHO | propyl | 5-methylthiophen-2-yl-CH2 | H | tert-butyl | H | 4-aminopyridin-3-yl |
| 170 | OH-NH-CHO | propyl | 5-methylthiophen-2-yl-CH2 | H | tert-butyl | H | 3-aminopyridin-2-yl |

TABLE IA-continued

| Example | W | $R_1$ | $R_2$ | $R_3$ | $R_4$ | $R_5$ | $R_6$ |
|---|---|---|---|---|---|---|---|
| 171 | N(OH)CHO | n-propyl | 5-methylthiophen-2-ylmethyl | H | CH2C(CH3)2CH2NHC(O)(2-pyridyl) | H | 2-pyridyl |
| 172 | N(OH)CHO | isopropyl | 2-methyl-3-phenylpropyl | H | 3-pyridyl | H | 2-thiazolyl |

TABLE IA-continued

TABLE IA-continued

| Example | W | $R_1$ | $R_2$ | $R_3$ | $R_4$ | $R_5$ | $R_6$ |
|---|---|---|---|---|---|---|---|
| 175 | HO-N(H)-CHO | propyl | 3-pyridyl-propyl | H | butyl-NH-C(O)-O-ethyl | H | thiazol-2-yl |
| 176 | HO-N(H)-CHO | propyl | (5-methylthien-2-yl)methyl | H | -CH2-C(O)-N(piperazine)-C(O)-O-ethyl | H | thiazol-2-yl |

TABLE IA-continued

| Example | W | R₁ | R₂ | R₃ | R₄ | R₅ | R₆ |
|---|---|---|---|---|---|---|---|
| 177 | OH-N(H)-C(=O)H | propyl | 5-methylthiophen-2-ylmethyl | H | -CH₂C(=O)N(CH₃)(OCH₃) | H | thiazol-2-yl |
| 178 | OH-N(H)-C(=O)H | isopropyl | 3-phenylpropyl | H | sec-butyl | H | thiazol-2-yl |
| 179 | OH-N(H)-C(=O)H | isopropyl | 3-phenylpropyl | H | sec-butyl | H | pyridin-2-yl |
| 180 | OH-N(H)-C(=O)H | propyl | benzyl | H | sec-butyl | H | pyridin-2-yl |

TABLE IA-continued

| Example | W | $R_1$ | $R_2$ | $R_3$ | $R_4$ | $R_5$ | $R_6$ |
|---|---|---|---|---|---|---|---|
| 181 | NHOH-CHO | iPr | 4-Cl-C6H4-(CH2)3- | H | tBu | H | 3-pyridyl |
| 182 | NHOH-CHO | Me | 2-thienyl-(CH2)3- | H | tBu | H | 3-pyridyl |
| 183 | NHOH-CHO | -CH2CH2CF3 | Ph-(CH2)3- | H | tBu | H | 2-thiazolyl |

TABLE IA-continued

| Example | W | $R_1$ | $R_2$ | $R_3$ | $R_4$ | $R_5$ | $R_6$ |
|---|---|---|---|---|---|---|---|
| 184 | HO-NH-CHO | CH₂CH₂CF₃ | PhCH₂CH₂CH₂- | H | isopropyl | H | thiazol-2-yl |
| 185 | HO-NH-CHO | CH₂CH₂CF₃ | PhCH₂CH₂CH₂- | H | CH(OMe)CH₃ | H | thiazol-2-yl |
| 186 | HO-NH-CHO | CH₂CH₂CF₃ | PhCH₂CH₂CH₂- | H | sec-butyl | H | pyridin-2-yl |

TABLE 1B
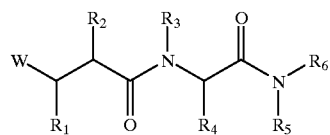
(I)
| Example | W | R₁ | R₂ | R₃ | R₄ | R₅ | R₆ |
|---|---|---|---|---|---|---|---|
| 187 | H-C(=O)-N(OH)- | ~ | phenylbutyl | H | -CH(CH₃)OCH₃ | H | 3-pyridyl |
| 188 | H-C(=O)-N(OH)- | ~ | phenylbutyl | H | -CH(CH₃)CH₂CH₃ | H | 3-pyridyl |
| 189 | H-C(=O)-N(OH)- | ~ | 4-(CF₃)phenylbutyl | H | -C(CH₃)₃ | H | 3-pyridyl |
| 190 | H-C(=O)-N(OH)- | ~ | 4-methylphenylbutyl | H | -C(CH₃)₃ | H | 3-pyridyl |
| 191 | H-C(=O)-N(OH)- | ~ | 4-tert-butylphenylbutyl | H | -C(CH₃)₃ | H | 3-pyridyl |

TABLE 1B-continued
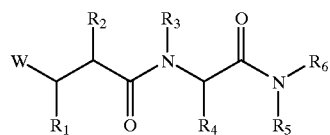
(I)
| Example | W | R₁ | R₂ | R₃ | R₄ | R₅ | R₆ |
|---|---|---|---|---|---|---|---|
| 192 | H-C(=O)-N(OH)- | — | -(CH₂)₅-Ph | H | t-Bu | H | 3-pyridyl |
| 193 | H-C(=O)-N(OH)- | — | -(CH₂)₃-(4-MeO-C₆H₄) | H | t-Bu | H | 3-pyridyl |
| 194 | H-C(=O)-N(OH)- | — | -(CH₂)₄-Ph | H | t-Bu | H | 3-pyridyl |
| 195 | H-C(=O)-N(OH)- | — | -(CH₂)₃-(4-Cl-C₆H₄) | H | t-Bu | H | 3-pyridyl |

TABLE 1B-continued (I)

| Example | W | R₁ | R₂ | R₃ | R₄ | R₅ | R₆ |
|---|---|---|---|---|---|---|---|
| 196 | H-C(=O)-N(OH)- | (attachment) | 4-phenoxyphenyl-propyl | H | tert-butyl | H | pyridin-3-yl |
| 197 | H-C(=O)-N(OH)- | CH₂CF₃ | 3-phenylpropyl | H | cyclohexyl | H | 1,3-thiazol-2-yl |

Compounds of the present invention which are currently preferred for their high biological activity are listed by name below in Tables 2A and 2B.

TABLE 2A

| Example | Chemical Name |
|---|---|
| 1 | (2R,3S)-3-(Formyl-hydroxyamino)-2-(3-phenyl-1-propyl)butanoic Acid [(1S)-2,2-Dimethyl-1-(pyridine-3-ylcarbamoyl)-1-propyl]amide |
| 2 | (2R,3S)-3-(Formyl-hydroxyamino)-2-(4-phenylcyclohexylmethyl)butanoic Acid [(1S)-2,2-Dimethyl-1-(1,3-thiazol-2-ylcarbamoyl)-1-propyl]amide |
| 3 | (2R,3S)-3-(Formyl-hydroxyamino)-2-(3-phenyl-1-propyl)hexanoic Acid [(1S)-5-Benzyloxycarbonylamino-1-(1,3,4-thiadiazol-2-yl-carbamoyl)-1-pentyl]amide |
| 4 | (2R,3S)-3-(Formyl-hydroxyamino)-2-(3-(3-furyl)-1-propyl)hexanoic Acid [(1S)-5-Benzyloxycarbonylamino-1-(1,3-thiazol-2-ylcarbamoyl)-1-pentyl]amide |
| 5 | (2R,3S)-3-(Formyl-hydroxyamino)-2-(3-(3-furyl)-1-propyl)hexanoic Acid [(1S)-2,2-Dimethyl-1-(1,3-thiazol-2-ylcarbamoyl)-1-propyl]amide |
| 6 | (2R,3S)-3-(Formyl-hydroxyamino)-2-(benzyloxymethyl)hexanoic Acid [(1S)-5-Benzyloxycarbonylamino-1-(1,3-thiazol-2-ylcarbamoyl)-1-pentyl]amide |
| 7 | (2R,3S)-3-(Formyl-hydroxyamino)-2-(3-phenyl-2-methyl-1-propyl)hexanoic Acid [(1R)-2-Methyl-2-(2-benzyloxycarbonylamino-1-ethylsulfanyl)-1-(1,3-thiazol-2-ylcarbamoyl)-1-propyl]-amide |
| 8 | (2R,3S)-3-(Formyl-hydroxyamino)-2-(3-phenyl-2-methyl-1-propyl)hexanoic Acid [(1S)-2,2-Dimethyl-1-(1,3-thiazol-2-ylcarbamoyl)-propyl]amide |
| 9 | (2R,3S)-3-(Formyl-hydroxyamino)-2-(3-phenyl-2-methyl-1-propyl)hexanoic Acid [(1S)-5-Benzyloxycarbonylamino-1-(1,3-thiazol-2-ylcarbamoyl)-1-pentyl]amide |
| 10 | (2R,3S)-3-(Formyl-hydroxyamino)-2-(benzothiophene-2-methyl)pentanoic Acid [(1S)-2,2-Dimethyl-1-(1,3-thiazol-2-yl-carbamoyl)-1-propyl]amide |
| 11 | (2R,3S)-3-(Formyl-hydroxyamino)-2-(3-phenyl-1-propyl)butanoic Acid [(1S)-2,2-Dimethyl-1-(2-pyridylcarbamoyl)-1-propyl]amide |

TABLE 2A-continued

| Example | Chemical Name |
|---|---|
| 12 | (2R,3S)-3-(Formyl-hydroxyamino)-2-(3-phenyl-1-propyl)butanoic Acid [(1S)-2-(3-Pyridyl)-1-(2-pyridylcarbamoyl)-1-ethyl]amide |
| 13 | (2R,3S)-3-(Formyl-hydroxyamino)-2-(3-phenyl-1-propyl)butanoic Acid [(1S)-5-Benzyloxycarbonylamino-1-(2-pyridylcarbamoyl)-1-pentyl]amide |
| 14 | (2R,3S)-3-(Formyl-hydroxyamino)-2-(3-phenyl-1-propyl)butanoic Acid [(1S)-5-(2-Naphthylacetylamino)-1-(2-pyridylcarbamoyl)-1-pentyl]amide |
| 15 | (2R,3S)-3-(Formyl-hydroxyamino)-2-(3-phenyl-1-propyl)butanoic Acid [(1S)-5-Benzyloxycarbonylamino-1-(1,3-thiazol-2-ylcarbamoyl)-1-pentyl]amide |
| 16 | (2R,3S)-3-(Formyl-hydroxyamino)-2-(3-benzyloxy-1-propyl)butanoic Acid [(1S)-4-Benzyloxycarbonylamino-1-(1,3-thiazol-2-ylcarbamoyl)-1-butyl]amide |
| 17 | (2R,3S)-3-(Formyl-hydroxyamino)-2-(3-phenyl-1-propyl)butanoic Acid [(1S)-4-Carbamoylamino-1-(2-pyridylcarbamoyl)-1-butyl]amide |
| 18 | (2R,3S)-3-(Formyl-hydroxyamino)-2-(3-phenyl-1-propyl)-7-methyloctanoic Acid [(1S,2S)-2-Methyl-1-(2-pyridylcarbamoyl)-1-butyl]amide |
| 19 | (2R,3S)-3-(Formyl-hydroxyamino)-2-(3-phenyl-1-propyl)-7-methyloctanoic Acid [(1S)-5-Benzyloxycarbonylamino-1-(1,3-thiazol-2-ylcarbamoyl)-1-pentyl]amide |
| 20 | (2R,3S)-3-(Formyl-hydroxyamino)-2-(3-phenyl-1-propyl)-7-methyloctanoic Acid [(1S)-2-(4-Hydroxphenyl)-1-(2-pyridylcarbamoyl)-1-ethyl]amide |
| 21 | (2R,3S)-3-(Formyl-hydroxyamino)-2-(3-phenyl-1-propyl)pentanoic Acid [(1S)-5-Benzyloxycarbonylamino-1-(1,3-thiazol-2-ylcarbamoyl)-1-pentyl]amide |
| 22 | 2R,3S)-3-(Formyl-hydroxyamino)-2-(3-phenyl-1-propyl)butanoic Acid [(1S,2S)-2-Methyl-1-(2-pyridylcarbamoyl)-1-butyl]amide |
| 23 | (2R,3S)-3-(Formyl-hydroxyamino)-2-(3-phenyl-1-propyl)-7-methyloctanoic Acid [(1 S)-2-(4-Chlorophenyl)-1-(2-pyridylcarbamoyl)-1-ethyl]amide |
| 24 | (2R,3S)-3-(Formyl-hydroxyamino)-2-(3-phenyl-1-propyl)butanoic Acid [(1S)-2-(4-Fluorophenyl)-1-(2-pyridylcarbamoyl)-1-ethyl]amide |
| 25 | (2R,3S)-3-(Formyl-hydroxyamino)-2-(3-phenyl-1-propyl)-7-methyloctanoic Acid [(1S)-4-(Imino-(2,3,6-trimethyl-4-methoxybenzenesulfonylamino)methylamino)-1-(1,3-thiazol-2-ylcarbamoyl)-1-butyl]amide |
| 26 | (2R,3S)-3-(Formyl-hydroxyamino)-2-(3-phenyl-1-propyl)hexanoic Acid [(1S)-2,2-Dimethyl-1-(1,3-thiazol-2-ylcarbamoyl)-1-propyl]amide |
| 27 | (2R,3S)-3-(Formyl-hydroxyamino)-2-(3-phenyl-1-propyl)butanoic Acid [(1S)-2,2-Dimethyl-1-(1,3-thiazol-2-ylcarbamoyl)-1-propyl]amide |
| 28 | (2R,3S)-3-(Formyl-hydroxyamino)-2-(3-phenyl-1-propyl)pentanoic Acid [(1S)-5-Benzyloxycarbonylamino-1-(pyridine-2-ylcarbamoyl)-1-pentyl]amide |
| 29 | (2R,3S)-3-(Formyl-hydroxyamino)-2-(3-phenyl-1-propyl)butanoic Acid [(1S)-5-Benzyloxycarbonylamino-1-(1,3-pyrimidin-2-ylcarbamoyl)-1-pentyl]amide |
| 30 | (2R,3S)-3-(Formyl-hydroxyamino)-2-(3-phenyl-1-propyl)butanoic Acid [2-(4-Benzyloxycarbonylaminophenyl)-1-(2-pyridylcarbamoyl)-1-ethyl]amide |
| 31 | (2R,3S)-3-(Formyl-hydroxyamino)-2-(3-phenyl-1-propyl)-7-methyloctanoic Acid [(1S)-2,2-Dimethyl-1-(2-pyridylcarbamoyl)-1-propyl]amide |
| 32 | (2R,3S)-3-(Formyl-hydroxyamino)-2-(3-phenyl-1-propyl)hexanoic Acid [(1S)-5-Benzyloxycarbonylamino-1-(1,3-thiazol-2-ylcarbamoyl)-1-pentyl]amide |
| 33 | (2R,3S)-3-(Formyl-hydroxyamino)-2-(3-phenyl-2-methyl-1-propyl)butanoic Acid [(1S)-5-Benzyloxycarbonylamino-1-(2-pyridylcarbamoyl)-1-pentyl]amide |
| 34 | (2R,3S)-3-(Formyl-hydroxyamino)-2-(3-phenyl-1-propyl)butanoic Acid [(1S)-2-Methyl-1-(2-pyridylcarbamoyl)-1-propyl]amide |
| 35 | (2R,3S)-3-(Formyl-hydroxyamino)-2-(3-phenyl-2-methyl-1-propyl)butanoic Acid [(1S,2S)-2-Methyl-1-(2-pyridylcarbamoyl)-1-butyl]amide |
| 36 | (2R,3S)-3-(Formyl-hydroxyamino)-2-(3-phenyl-1-propyl)hexanoic Acid [(1S)-1-Cyclohexyl-1-(2-pyridylcarbamoyl)methyl]amide |
| 37 | (2R,3S)-3-(Formyl-hydroxyamino)-2-(3-phenyl-1-propyl)butanoic Acid [(1S)-2-(3-Pyridyl)-1-(2-pyridylcarbamoyl)-1-ethyl]amide |
| 38 | (2R,3S)-3-(Formyl-hydroxyamino)-2-(3-phenyl-2-methyl-1-propyl)butanoic Acid [(1S)-2,2-Dimethyl-1-(2-pyridylcarbamoyl)-1-propyl]amide |
| 39 | (2R,3S)-3-(Formyl-hydroxyamino)-2-(3-phenyl-1-propyl)hexanoic Acid [(1S)-4-(Imino-(2,3,6-trimethyl-4-methoxybenzenesulfonylamino)methylamino)-1-(1,3-thiazol-2-ylcarbamoyl)-1-butyl]amide |
| 40 | (2R,3S)-3-(Formyl-hydroxyamino)-2-(3-phenyl-1-propyl)-6,6,6-trifluorohexanoic Acid [(1S)-2,2-Dimethyl-1-(pyridine-2-ylcarbamoyl)-1-methyl]amide |
| 41 | (2R,3S)-3-(Formyl-hydroxyamino)-2-(3-phenyl-1-propyl)butanoic Acid [(1S)-1-Cyclohexyl-1-(2-pyridylcarbamoyl)methyl]amide |
| 42 | (2R,3S)-3-(Formyl-hydroxyamino)-2-(3-phenyl-1-propyl)butanoic Acid [(1S)-2,2-Dimethyl-1-(1,3-thiazol-2-ylcarbamoyl)-1-propyl]amide |
| 43 | (2R,3S)-3-(Formyl-hydroxyamino)-2-(2-phenyl-1-ethyl)butanoic Acid [(1S)-2,2-Dimethyl-1-(1,3-thiazol-2-ylcarbamoyl)-1-propyl]amide |
| 44 | (2R,3S)-3-(Formyl-hydroxyamino)-2-(3-phenyl-1-propyl)butanoic Acid [(1S)-5-Cyclopentylacetylamino-1-(1,3-thiazol-2-ylcarbamoyl)-1-pentyl]amide |
| 45 | (2R,3S)-3-(Formyl-hydroxyamino)-2-(3-phenyl-1-propyl)butanoic Acid [(1S)-5-Cyclopentylacetylamino-1-(pyridine-2-ylcarbamoyl)-1-pentyl]amide |

TABLE 2A-continued

| Example | Chemical Name |
|---|---|
| 46 | (2R,3S)-3-(Formyl-hydroxyamino)-2-(3-phenyl-1-propyl)butanoic Acid [(1S)-5-(3-Methoxyphenylcarbonylamino)-1-(1,3-thiazol-2-ylcarbamoyl)-1-pentyl]amide |
| 47 | (2R,3S)-3-(Formyl-hydroxyamino)-2-(3-phenyl-1-propyl)hexanoic Acid [(1S)-5-Benzyloxycarbonylamino-1-(1,3,4-thiadiazol-2-ylcarbamoyl)-1-pentyl]amide |
| 48 | (2R,3S)-3-(Formyl-hydroxyamino)-2-(3-(3-furyl)-1-propyl)hexanoic Acid [(1S)-5-Benzyloxycarbonylamino-1-(1,3-thiazol-2-ylcarbamoyl)-1-pentyl]amide |
| 49 | (2R,3S)-3-(Formyl-hydroxyamino)-2-(3-(3-pyridyl)-1-propyl)hexanoic Acid [(1S)-5-Benzyloxycarbonylamino-1-(1,3-thiazol-2-ylcarbamoyl)-1-pentyl]amide |
| 50 | (2R,3S)-3-(Formyl-hydroxyamino)-2-(3-phenyl-1-propyl)hexanoic Acid [(1S)-5-Benzyloxycarbonylamino-1-(5-methyl-1,2-isoxazol-3-ylcarbamoyl)-1-pentyl]amide |
| 51 | (2R,3S)-3-(Formyl-hydroxyamino)-2-(3-phenyl-2-methyl-1-propyl)hexanoic Acid [(1S)-2,2-Dimethyl-1-(1,3-thiazol-2-ylcarbamoyl)-1-propyl]amide |
| 52 | (2R,3S)-3-(Formyl-hydroxyamino)-2-(2-benzyloxy-1-ethyl)hexanoic Acid [(1S)-5-Benzyloxycarbonylamino-1-(1,3-thiazol-2-ylcarbamoyl)-1-pentyl]amide |
| 53 | (2R,3S)-3-(Formyl-hydroxyamino)-2-(benzyloxymethyl)hexanoic Acid [(1S)-5-Benzyloxycarbonylamino-1-(1,3-thiazol-2-ylcarbamoyl)-1-pentyl]amide |
| 54 | (2R,3S)-3-(Formyl-hydroxyamino)-2-(3-phenyl-2-methyl-1-propyl)butanoic Acid [(1S)-5-Benzyloxycarbonylamino-1-(1,3-thiazol-2-ylcarbamoyl)-1-pentyl]amide |
| 55 | (2R,3S)-3-(Formyl-hydroxyamino)-2-(3-phenyl-2-methyl-1-propyl)butanoic Acid [(1S)-2,2-Dimethyl-1-(1,3-thiazol-2-ylcarbamoyl)-1-propyl]amide |
| 56 | (2R,3S)-3-(Formyl-hydroxyamino)-2-(3-phenyl-2-methyl-1-propyl)hexanoic Acid [(1S)-5-Benzyloxycarbonylamino-1-(pyridine-2-ylcarbamoyl)-1-pentyl]amide |
| 57 | (2R,3S)-3-(Formyl-hydroxyamino)-2-(3-(3-thiophene)-1-propyl)hexanoic Acid [(1S)-2,2-Dimethyl-1-(1,3-thiazol-2-ylcarbamoyl)-1-propyl]amide |
| 58 | (2R,3S)-3-(Formyl-hydroxyamino)-2-(3-(3-furyl)-1-propyl)hexanoic Acid [(1S)-2,2-Dimethyl-1-(1,3-thiazol-2-ylcarbamoyl)-1-propyl]amide |
| 59 | (2R,3S)-3-(Formyl-hydroxyamino)-2-(2-benzofuranmethyl)hexanoic Acid [(1S)-2,2-Dimethyl-1-(1,3-thiazol-2-ylcarbamoyl)-1-propyl]amide |
| 60 | (2R,3S)-3-(Formyl-hydroxyamino)-2-(2-benzofuranmethyl)hexanoic Acid [(1S)-5-Benzyloxycarbonylamino-1-(2-pyridylcarbamoyl)-1-pentyl]amide |
| 61 | (2R,3S)-3-(Formyl-hydroxyamino)-2-(3-phenyl-2-methyl-1-propyl)hexanoic Acid [(1S)-5-Benzyloxycarbonylamino-1-(1,3-thiazol-2-ylcarbamoyl)-1-pentyl]amide |
| 62 | (2R,3R)-4-(2-Thiophenesulfanyl)-3-(formyl-hydroxyamino)-2-(3-phenyl-2-methyl-1-propyl)butanoic Acid [(1S)-2,2-Dimethyl-1-(1,3-thiazol-2-ylcarbamoyl)-1-propyl]amide |
| 63 | (2R,3S)-3-(Formyl-hydroxyamino)-2-(3-(1,3-pyrimidine-2-yl)-1-propyl)hexanoic Acid [(1S)-2,2-Dimethyl-1-(1,3-thiazol-2-ylcarbamoyl)-1-propyl]amide |
| 64 | (2R,3S)-3-(Formyl-hydroxyamino)-2-(5-methyl-2-thiophenemethyl)hexanoic Acid [(1S)-2,2-Dimethyl-1-(1,3-thiazol-2-ylcarbamoyl)-1-propyl]amide |
| 65 | (2R,3S)-3-(Formyl-hydroxyamino)-2-(3-(1,3-thiazol-2-yl)-1-propyl)hexanoic Acid [(1S)-2,2-Dimethyl-1-(1,3-thiazol-2-ylcarbamoyl)-1-propyl]amide |
| 66 | (2R,3R)-4-(3-Aminophenoxy)-3-(formyl-hydroxyamino)-2-(3-phenyl-2-methyl-1-propyl)butanoic Acid [(1S)-2,2-Dimethyl-1-(1,3-thiazol-2-ylcarbamoyl)-1-propyl]amide |
| 67 | (2R,3R)-4-(2-Thiophenesulfanyl)-3-(formyl-hydroxyamino)-2-(3-phenyl-2-methyl-1-propyl)butanoic Acid [(1S)-2,2-Dimethyl-1-(1,3-thiazol-2-ylcarbamoyl)-1-propyl]amide |
| 68 | (2R,3R)-4-(2-Tetrazolyl)-3-(formyl-hydroxyamino)-2-(3-phenyl-2-methyl-1-propyl)butanoic Acid [(1S)-2,2-Dimethyl-1-(1,3-thiazol-2-ylcarbamoyl)-1-propyl]amide |
| 69 | (2R,3S)-3-(Formyl-hydroxyamino)-2-(3-(3-furyl)-1-propyl)hexanoic Acid [(1S)-2,2-Dimethyl-1-(1,3,4-thiadiazol-2-ylcarbamoyl)-1-propyl]amide |
| 70 | (2R,3S)-5-(2-Pyridyl)-3-(formyl-hydroxyamino)-2-(3-phenyl-2-methyl-1-propyl)pentanoic Acid [(1S)-2,2-Dimethyl-1-(1,3-thiazol-2-ylcarbamoyl)-1-propyl]amide |
| 71 | (2R,3R)-5-(3-Furyl)-3-(formyl-hydroxyamino)-2-(3-phenyl-2-methyl-1-propyl)pentanoic Acid [(1S)-2,2-Dimethyl-1-(1,3-thiazol-2-ylcarbamoyl)-1-propyl]amide |
| 72 | (2R,3S)-5-(1,3-Thiazol-2-yl)-3-(formyl-hydroxyamino)-2-(3-phenyl-2-methyl-1-propyl)pentanoic Acid [(1S)-2,2-Dimethyl-1-(1,3-thiazol-2-ylcarbamoyl)-1-propyl]amide |
| 73 | (2R,3S)-3-(Formyl-hydroxyamino)-2-(3-(3-benzothiophene)-1-propyl)hexanoic Acid [(1S)-2,2-Dimethyl-1-(1,3-thiazol-2-ylcarbamoyl)-1-propyl]amide |
| 74 | (2R,3S)-3-(Formyl-hydroxyamino)-2-(3-(3-benzofuran)-1-propyl)hexanoic Acid [(1S)-2,2-Dimethyl-1-(1,3-thiazol-2-ylcarbamoyl)-1-propyl]amide |

TABLE 2A-continued

| Example | Chemical Name |
| --- | --- |
| 75 | (2R,3S)-3-(Formyl-hydroxyamino)-2-(2-benzothiophenemethyl)pentanoic Acid [(1S)-5-Benzyloxycarbonylamino)-1-(1,3-thiazol-2-ylcarbamoyl)-1-pentyl]amide |
| 76 | (2R,3S)-3-(Formyl-hydroxyamino)-2-(benzothiophene-2-methyl)pentanoic Acid [(1S)-5-Ethoxycarbonylamino-1-(2-pyridylcarbamoyl)-1-pentyl]amide |
| 77 | (2R,3S)-3-(Formyl-hydroxyamino)-2-[(2E)-3-phenyl-2-propene-1-yl]hexanoic Acid [(1S)-2,2-Dimethyl-1-(1,3,4-thiadiazol-2-ylcarbamoyl)-1-propyl]amide |
| 78 | (2R,3S)-3-(Formyl-hydroxyamino)-2-(4-phenyl-1-butyl)butanoic Acid [(1S)-2,2-Dimethyl-1-(1,3,4-thiadiazol-2-ylcarbamoyl)-1-propyl]amide |
| 79 | (2R,3S)-3-(Formyl-hydroxyamino)-2-(3-(2-thiophene)-1-propyl)hexanoic Acid [(1S)-2,2-Dimethyl-1-(1,3,4-thiadiazol-2-ylcarbamoyl)-1-propyl]amide |
| 80 | (2R,3S)-3-(Formyl-hydroxyamino)-2-(3-(2-pyridyl)-1-propyl)hexanoic Acid [(1S)-2,2-Dimethyl-1-(1,3-thiazol-2-ylcarbamoyl)-1-propyl]amide |
| 81 | (2R,3S)-3-(Formyl-hydroxyamino)-2-(2-thiophenemethyl)hexanoic Acid [(1S)-5-Benzyloxycarbonylamino)-1-(1,3-thiazol-2-ylcarbamoyl)-1-pentyl]amide |
| 82 | (2R,3S)-3-(Formyl-hydroxyamino)-2-(2-furanmethyl)pentanoic Acid [(1S)-5-Benzyloxycarbonylamino)-1-(1,3-thiazol-2-ylcarbamoyl)-1-pentyl]amide |
| 83 | (2R,3S)-3-(Formyl-hydroxyamino)-2-(4-fluorobenzyl)hexanoic Acid [(1S)-2,2-Dimethyl-1-(1,3-thiazol-2-ylcarbamoyl)-1-propyl]amide |
| 84 | (2R,3S)-3-(Formyl-hydroxyamino)-2-(2-benzothiophenemethyl)pentanoic Acid [(1R)-2-Methyl-2-(2-ethoxycarbonylamino-1-ethylsulfanyl)-1-(1,3-thiazol-2-ylcarbamoyl)-1-propyl]amide |
| 85 | (2R,3S)-3-(Formyl-hydroxyamino)-2-(2-furylmethyl)hexanoic Acid [(1S)-2,2-Dimethyl-1-(1,3-thiazol-2-ylcarbamoyl)-1-propyl]amide |
| 86 | (2R,3S)-3-(Formyl-hydroxyamino)-2-(2-benzothiophenemethyl)pentanoic Acid [(1S)-5-Ethoxycarbonylamino)-1-(1,3-thiazol-2-ylcarbamoyl)-1-pentyl]amide |
| 87 | (2R,3S)-3-(Formyl-hydroxyamino)-2-(5-methyl-2-thiophenemethyl)hexanoic Acid [(1S)-2,2-Dimethyl-1-(1,3-thiazol-2-ylcarbamoyl)-1-propyl]amide |
| 88 | (2R,3S)-3-(Formyl-hydroxyamino)-2-(3-benzyloxy-1-propyl)butanoic Acid [(1S)-4-Benzyloxycarbonylamino)-1-(pyridine-2-ylcarbamoyl)-1-butyl]amide |
| 89 | (2R,3S)-3-(Formyl-hydroxyamino)-2-(1,2,3,4-tetrahydronaphthyl-2-methyl)butanoic Acid [(1S)-S-Benzyloxycarbonylamino)-1-(pyridine-2-ylcarbamoyl)-1-pentyl]amide |
| 90 | (2R,3S)-3-(Formyl-hydroxyamino)-2-(3-phenyl-1-butyl)butanoic Acid [(1S)-5-Benzyloxycarbonylamino)-1-(pyridine-2-ylcarbamoyl)-1-pentyl]amide |
| 91 | (2R,3S)-3-(Formyl-hydroxyamino)-2-(1,2,3,4-tetrahydronaphthyl-2-methyl)butanoic Acid [(1S,2S)-2-Methyl-1-(pyridine-2-ylcarbamoyl)-1-butyl]amide |
| 92 | (2R,3S)-3-(Formyl-hydroxyamino)-2-(3-phenyl-1-propyl)hexanoic Acid [(1S)-2-(3-Pyridyl)-1-(1,3-thiazol-2-ylcarbamoyl)-1-ethyl]amide |
| 93 | (2R,3S)-3-(Formyl-hydroxyamino)-2-(3-phenyl-1-propyl)butanoic Acid [(1S)-3-Phenyl-1-(2-pyridylcarbamoyl)-1-propyl]amide |
| 94 | (2R,3S)-3-(Formyl-hydroxyamino)-2-(3-phenyl-1-propyl)-6,6,6-trifluorohexanoic Acid [(1S)-1-Phenyl-1-(1,3-thiazol-2-ylcarbamoyl)-1-methyl]amide |
| 95 | (2R,3S)-3-(Formyl-hydroxyamino)-2-(3-phenyl-2-methyl-1-propyl)butanoic Acid [(1S)-5-Benzyloxycarbonylamino)-1-(pyridine-2-ylcarbamoyl)-1-pentyl]amide |
| 96 | (2R,3S)-3-(Formyl-hydroxyamino)-2-(1,2,3,4-tetrahydronaphthyl-2-methyl)butanoic Acid [(1S)-2,2-Dimethyl-1-(1,3-thiazol-2-ylcarbamoyl)-1-propyl]amide |
| 97 | (2R,3S)-3-(Formyl-hydroxyamino)-2-(4-phenylcyclohexylmethyl)butanoic Acid [(1S)-5-Benzyloxycarbonylamino)-1-(pyridine-2-ylcarbamoyl)-1-pentyl]amide |
| 98 | (2R,3S)-3-(Formyl-hydroxyamino)-2-(1,2,3,4-tetrahydronaphthyl-2-methyl)-4-pentenoic Acid [(1S)-4-(Imino-(2,3,6-trimethyl-4-methoxybenzenesulfonylamino)methylamino)-1-(1,3-thiazol-2-ylcarbamoyl)-1-butyl]amide |
| 99 | (2R,3S)-3-(Formyl-hydroxyamino)-2-(1,2,3,4-tetrahydronaphthyl-2-methyl)-4-pentenoic Acid [(1S)-2,2-Dimethyl-1-(1,3-thiazol-2-ylcarbamoyl)-1-propyl]amide |
| 100 | (2R,3S)-3-(Formyl-hydroxyamino)-2-(1,2,3,4-tetrahydronaphthyl-2-methyl)butanoic Acid [(1S)-5-Benzyloxycarbonylamino)-1-(pyridine-2-ylcarbamoyl)-1-pentyl]amide |
| 101 | (2R,3S)-3-(Formyl-hydroxyamino)-2-(3-phenyl-1-propyl)-6,6,6-trifluorohexanoic Acid [(1S)-3-Methyl-1-(1,3-thiazol-2-ylcarbamoyl)-1-butyl]amide |
| 102 | (2R,3S)-3-(Formyl-hydroxyamino)-2-(2,3-dihydrobenzo[1,4]dioxine-2-methyl)butanoic Acid [(1S)-2,2-Dimethyl-1-(1,3-thiazol-2-ylcarbamoyl)-1-propyl]amide |
| 103 | (2R,3S)-3-(Formyl-hydroxyamino)-2-(2-benzyloxy-1-ethyl)hexanoic Acid [(1S)-2,2-Dimethyl-1-(1,3-thiazol-2-ylcarbamoyl)-1-propyl]amide |
| 104 | (2R,3S)-3-(Formyl-hydroxyamino)-2-(3-phenyl-2-ethyl-1-propyl)hexanoic Acid [(1S)-2,2-Dimethyl-1-(1,3-thiazol-2-ylcarbamoyl)-1-propyl]amide |
| 105 | (2R,3S)-3-(Formyl-hydroxyamino)-2-(2-naphthylmethyl)hexanoic Acid [(1S)-5-Benzyloxycarbonylamino)-1-(pyridine-2-ylcarbamoyl)-1-pentyl]amide |

TABLE 2A-continued

| Example | Chemical Name |
|---|---|
| 106 | (2R,3S)-3-(Formyl-hydroxyamino)-2-(3-phenyl-2-ethyl-1-propyl)hexanoic Acid [(1S)-5-Benzyloxycarbonylamino)-1-(pyridine-2-ylcarbamoyl)-1-pentyl]amide |
| 107 | (2R,3S)-3-(Formyl-hydoxyamino)-2-(2,3-dihydrobenzo[1,4]dioxine-2-methyl)butanoic Acid [(1S)-5-Benzyloxycarbonylamino)-1-(pyridine-2-ylcarbamoyl)-1-pentyl]amide |
| 108 | (2R,3R)-3-(Formyl-hydroxyamino)-2-(3-phenyl-2-methyl-1-propyl)-4-(2-nitrophenoxy)butanoic Acid [(1S)-2,2-Dimethyl-1-(1,3-thiazol-2-ylcarbamoyl)-1-propyl]amide |
| 109 | (2R,3R)-3-(Formyl-hydroxyamino)-2-(3-phenyl-2-methyl-1-propyl)-4-(3-nitrophenoxy)butanoic Acid [(1S)-2,2-Dimethyl-1-(1,3-thiazol-2-ylcarbamoyl)-1-propyl]amide |
| 110 | (2R,3R)-3-(Formyl-hydroxyamino)-2-(3-phenyl-2-methyl-1-propyl)-4-(2-nitrophenoxy)butanoic Acid [(1S)-4-(Imino-(2,3,6-trimethyl-4-methoxybenzenesulfonylamino)methylamino)-1-(1,3-thiazol-2-ylcarbamoyl)-1-butyl]amide |
| 111 | (2R,3S)-3-(Formyl-hydroxyamino)-2-(chroman-2-methyl)butanoic Acid [(1S)-2,2-Dimethyl-1-(1,3-thiazol-2-ylcarbamoyl)-1-propyl]amide |
| 112 | (2R,3S)-3-(Formyl-hydroxyamino)-2-(3-phenyl-1-propyl)hexanoic Acid [(1S-2,2-Dimethyl-1-(1,3,4-thiadiazol-2-ylcarbamoyl)-1-propyl]amide |
| 113 | (2R,3R)-3-(Formyl-hydroxyamino)-2-((2E)-3-phenyl-2-methyl-2-propen-1-yl)-5-(thiophene-3-yl)-4-pentynoic Acid [(1S)-2,2-Dimethyl-1-(1,3-thiazol-2-ylcarbamoyl)-1-propyl]amide |
| 114 | (2R,3S)-3-(Formyl-hydroxyamino)-2-(3-phenyl-2-methyl-1-propyl)-5-(4-trifluorophenyl)pentanoic Acid [(1S)-2,2-Dimethyl-1-(1,3-thiazol-2-ylcarbamoyl)-1-propyl]amide |
| 115 | (2R,3S)-3-(Formyl-hydroxyamino)-2-(3-(thiophene-2-yl)-1-propyl)hexanoic Acid [(1S)-2,2-Dimethyl-1-(1,3-thiazol-2-ylcarbamoyl)-1-propyl]amide |
| 116 | (2R,3S)-3-(Formyl-hydroxyamino)-2-(4-phenyl-3-methyl-2-butyl)hexanoic Acid [(1S)-5-Benzyloxycarbonylamino)-1-(1,3-thiazol-2-ylcarbamoyl)-1-pentyl]amide |
| 117 | (2R,3S)-3-(Formyl-hydroxyamino)-2-(2-thiophenemethyl)hexanoic Acid [(1S)-2,2-Dimethyl-1-(1,3-thiazol-2-ylcarbamoyl)-1-propyl]amide |
| 118 | (2R,3S)-3-(Formyl-hydroxyamino)-2-(4-phenyl-2-butyl)hexanoic Acid [(1S)-5-Benzyloxycarbonylamino)-1-(pyridine-2-ylcarbamoyl)-1-pentyl]amide |
| 119 | (2R,3S)-3-(Formyl-hydroxyamino)-2-(4-(thiophene-3-yl)-2-butyl)hexanoic Acid [(1S)-5-Benzyloxycarbonylamino)-1-(pyridine-2-ylcarbamoyl)-1-pentyl]amide |
| 120 | (2R,3S)-3-(Formyl-hydroxyamino)-2-(2-benzothiophenemethyl)pentanoic Acid [(1S)-5-Benzyloxycarbonylamino)-1-(pyridine-2-ylcarbamoyl)-1-pentyl]amide |
| 121 | (2R,3S)-3-(Formyl-hydroxyamino)-2-(3-phenyl-1-propyl)-6,6,6-trifluorohexanoic Acid [(1S,2S)-2-Methyl-1-(1,3-thiazol-2-ylcarbamoyl)-1-butyl]amide |
| 122 | (2R,3S)-3-(Formyl-hydroxyamino)-2-(3-phenyl-1-propyl)-6,6,6-trifluorohexanoic Acid [(1S,2R)-2-Hydroxy-1-(1,3-thiazol-2-ylcarbamoyl)-1-propyl]amide |
| 123 | (2R,3S)-3-(Formyl-hydroxyamino)-2-(5-methyl-2-thiophenemethyl)hexanoic Acid [(1S)-5-Ethoxycarbonylamino)-1-(pyridine-2-ylcarbamoyl)-1-pentyl]amide |
| 124 | (2R,3S)-3-(Formyl-hydroxyamino)-2-(3-(thiophene-2-yl)-1-propyl)hexanoic Acid [(1S)-5-Ethoxycarbonylamino)-1-(pyridine-2-ylcarbamoyl)-1-pentyl]amide |
| 125 | (2R,3S)-3-(Formyl-hydroxyamino)-2-(2-benzoxazolylmethyl)hexanoic Acid [(1S)-5-Ethoxycarbonylamino)-1-(pyridine-2-ylcarbamoyl)-1-pentyl]amide |
| 126 | (2R,3S)-3-(Formyl-hydroxyamino)-2-(2-benzothiophenemethyl)pentanoic Acid [(1S)-5-Ethoxycarbonylamino)-1-(pyridine-2-ylcarbamoyl)-1-pentyl]amide |
| 127 | (2R,3S)-3-(Formyl-hydroxyamino)-2-(3-benzothiophenemethyl)pentanoic Acid [(1S)-5-Ethoxycarbonylamino)-1-(pyridine-2-ylcarbamoyl)-1-pentyl]amide |
| 128 | (2R,3S)-3-(Formyl-hydroxyamino)-2-(2-benzoxazolylmethyl)hexanoic Acid [(1S)-2,2-Dimethyl-1-(pyridine-2-ylcarbamoyl)-1-propyl]amide |
| 129 | (2R,3S)-3-(Formyl-hydroxyamino)-2-(2-benzothiophenemethyl)pentanoic Acid [(1S,2R)-2-Methoxy-1-(pyridine-2-ylcarbamoyl)-1-propyl]amide |
| 130 | (2R,3S)-3-(Formyl-hydroxyamino)-2-(3-thiophenemethyl)hexanoic Acid [(1S)-2,2-Dimethyl-1-(1,3-thiazol-2-ylcarbamoyl)-1-propyl]amide |
| 131 | (2R,3S)-3-(Formyl-hydroxyamino)-2-(4-(furan-3-yl)-2-butyl)hexanoic Acid [(1S)-5-Benzyloxycarbonylamino)-1-(pyridine-2-ylcarbamoyl)-1-pentyl]amide |
| 132 | (2R,3S)-3-(Formyl-hydroxyamino)-2-(3-phenyl-2-methyl-1-propyl)hexanoic Acid [(1S)-2,2-Dimethyl-1-(1,3,4-thiadiazol-2-ylcarbamoyl)-1-propyl]amide |
| 133 | (2R,3S)-3-(Formyl-hydroxyamino)-2-(5-methyl-2-thiophenemethyl)hexanoic Acid [(1S,2R)-2-Benzyloxy-1-(1,3-thiazol-2-ylcarbamoyl)-1-propyl]amide |
| 134 | (2R,3S)-3-(Formyl-hydroxyamino)-2-(5-methyl-2-thiophenemethyl)hexanoic Acid [(1S,2R)-2-Hydroxy-1-(1,3-thiazol-2-ylcarbamoyl)-1-propyl]amide |
| 135 | (2R,3S)-3-(Formyl-hydroxyamino)-2-(3-phenyl-1-propyl)hexanoic Acid [(1S)-2,2-Dimethyl-1-(5-methyl-1,3-thiazol-2-ylcarbamoyl)-1-propyl]amide |

TABLE 2A-continued

| Example | Chemical Name |
|---|---|
| 136 | (2R,3S)-3-(Formyl-hydroxyamino)-2-(3-phenyl-1-propyl)hexanoic Acid [(1S)-2,2-Dimethyl-1-(pyridine-3-ylcarbamoyl)-1-propyl]amide |
| 137 | (2R,3S)-3-(Formyl-hydroxyamino)-2-(5-methyl-2-thiophenemethyl)hexanoic Acid [(1S)-2,2-Dimethyl-1-(pyridine-3-ylcarbamoyl)-1-propyl]amide |
| 138 | (2R,3S)-3-(Formyl-hydroxyamino)-2-(5-methyl-2-thiophenemethyl)hexanoic Acid [(1S)-2,2-Dimethyl-1-(3-hydroxypyridine-2-ylcarbamoyl)-1-propyl]amide |
| 139 | (2R,3S)-3-(Formyl-hydroxyamino)-2-(3-phenyl-1-propyl)hexanoic Acid [(1S)-2,2-Dimethyl-1-(5-ethanesulfanyl-1,3,4-thiadiazol-2-ylcarbamoyl)-1-propyl]amide |
| 140 | (2R,3S)-3-(Formyl-hydroxyamino)-2-(5-methyl-2-thiophenemethyl)hexanoic Acid [(1S)-2,2-Dimethyl-1-(pyridine-4-ylcarbamoyl)-1-propyl]amide |
| 141 | (2R,3S)-3-(Formyl-hydroxyamino)-2-(5-methyl-2-thiophenemethyl)hexanoic Acid [(1S)-2,2-Dimethyl-1-(1,3,4-thiadiazol-2-ylcarbamoyl)-1-propyl]amide |
| 142 | (2R,3S)-3-(Formyl-hydroxyamino)-2-(5-methyl-2-thiophenemethyl)hexanoic Acid [(1S,2R)-2-Hydroxy-1-(pyridine-2-ylcarbamoyl)-1-propyl]amide |
| 143 | (2R,3S)-3-(Formyl-hydroxyamino)-2-(3-phenyl-1-propyl)-4-methylpentanoic Acid [(1S)-2,2-Dimethyl-1-(1,3,4-thiadiazol-2-ylcarbamoyl)-1-propyl]amide |
| 144 | (2R,3S)-3-(Formyl-hydroxyamino)-2-(5-methyl-2-thiophenemethyl)hexanoic Acid [(1S,2R)-2-Hydroxy-1-(1,3-pyrimidine-2-ylcarbamoyl)-1-propyl]amide |
| 145 | (2R,3S)-3-(Formyl-hydroxyamino)-2-(5-methyl-2-thiophenemethyl)hexanoic Acid [(1S,2R)-2-Methoxy-1-(1,3-thiazol-2-ylcarbamoyl)-1-propyl]amide |
| 146 | (2R,3S)-3-(Formyl-hydroxyamino)-2-(5-methyl-2-thiophenemethyl)hexanoic Acid [(1S,2R)-2-(2-Pyridylmethoxy)-1-(1,3-thiazol-2-ylcarbamoyl)-1-propyl]amide |
| 147 | (2R,3S)-3-(Formyl-hydroxyamino)-2-(5-methyl-2-thiophenemethyl)hexanoic Acid [(1S)-3-Methanesulfonyl-1-(pyridine-2-ylcarbamoyl)-1-propyl]amide |
| 148 | (2R,3S)-3-(Formyl-hydroxyamino)-2-(5-methyl-2-thiophenemethyl)hexanoic Acid [(1S)-3-Dimethylaminocarbonyl-1-(pyridine-2-ylcarbamoyl)-1-propyl]amide |
| 149 | (2R,3S)-3-(Formyl-hydroxyamino)-2-(5-methyl-2-thiophenemethyl)hexanoic Acid [(1S)-5-(2-Pyridylcarbonylamino)-1-(1,3-thiazol-2-ylcarbamoyl)-1-pentyl]amide |
| 150 | (2R,3S)-3-(Formyl-hydroxyamino)-2-(3-phenyl-1-propyl)-4-methylpentanoic Acid [(1S)-2,2-Dimethyl-1(pyridine-3-ylcarbamoyl)-1-propyl]amide |
| 151 | (2R,3S)-3-(Formyl-hydroxyamino)-2-(5-methyl-2-thiophenemethyl)hexanoic Acid [(1S)-2,2-Dimethyl-1-(pyrazine-2-ylcarbamoyl)-1-propyl]amide |
| 152 | (2R,3S)-3-(Formyl-hydroxyamino)-2-(5-methyl-2-thiophenemethyl)hexanoic Acid [(1S)-2-Methyl-2-hydroxy-1-(1,3-thiazol-2-ylcarbamoyl)-1-propyl]amide |
| 153 | (2R,3S)-3-(Formyl-hydroxyamino)-2-(5-methyl-2-thiophenemethyl)hexanoic Acid [(1R)-2-Methyl-2-methanesulfanyl-1-(1,3-thiazol-2-ylcarbamoyl)-1-propyl]amide |
| 154 | (2R,3S)-3-(Formyl-hydroxyamino)-2-(5-methyl-2-thiophenemethyl)hexanoic Acid [(1S)-2,2-Dimethyl-1-(5-methyl-1,3,4-thiadiazol-2-ylcarbamoyl)-1-propyl]amide |
| 155 | (2R,3S)-3-(Formyl-hydroxyamino)-2-(5-methyl-2-thiophenemethyl)hexanoic Acid [(1S)-3-Dimethylaminosulfonyl-1-(1,3-thiazol-2-ylcarbamoyl)-1-propyl]amide |
| 156 | (2R,3S)-3-(Formyl-hydroxyamino)-2-(5-methyl-2-thiophenemethyl)hexanoic Acid [(1S)-2-Dimethylaminocarbonyl-1-(2-pyridylcarbamoyl)-1-ethyl]amide |
| 157 | (2R,3S)-3-(Formyl-hydroxyamino)-2-(5-methyl-2-thiophenemethyl)hexanoic Acid [(1S)-2,2-Dimethyl-1-(5-methyl-1,3-thiazol-2-ylcarbamoyl)-1-propyl]amide |
| 158 | (2R,3S)-3-(Formyl-hydroxyamino)-2-(5-methyl-2-thiophenemethyl)hexanoic Acid [(1S)-2,2-Dimethyl-1-(6-aminopyridine-3-ylcarbamoyl)-1-propyl]amide |
| 159 | (2R,3S)-3-(Formyl-hydroxyamino)-2-(5-methyl-2-thiophenemethyl)hexanoic Acid [(1S,2S)-2-Methyl-1-(1,3-thiazol-2-ylcarbamoyl)-1-butyl]amide |
| 160 | (2R,3S)-3-(Formyl-hydroxyamino)-2-(5-methyl-2-thiophenemethyl)hexanoic Acid [(1S)-2-Carbamoylamino-1-(1,3-thiazol-2-ylcarbamoyl)-1-ethyl]amide |
| 161 | (2R,3S)-3-(Formyl-hydroxyamino)-2-(5-methyl-2-thiophenemethyl)hexanoic Acid [(1S,2R)-2-(2-Methyl-1-propoxy)-1-(1,3-thiazol-2-ylcarbamoyl)-1-propyl]amide |
| 162 | (2R,3S)-3-(Formyl-hydroxyamino)-2-(3-phenyl-2-methyl-1-propyl)-4-methylpentanoic Acid [(1S)-2,2-Dimethyl-1-(1,3-thiazol-2-ylcarbamoyl)-1-propyl]amide |
| 163 | (2R,3S)-3-(Formyl-hydroxyamino)-2-(3-phenyl-2-methyl-1-propyl)-4-methylpentanoic Acid [(1S,2R)-2-Hydroxy-1-(1,3-thiazol-2-ylcarbamoyl)-1-propyl]amide |
| 164 | (2R,3S)-3-(Formyl-hydroxyamino)-2-(5-methyl-2-thiophenemethyl)hexanoic Acid [(1S)-2-Acetylamino-1-(1,3-thiazol-2-ylcarbamoyl)-1-ethyl]amide |
| 165 | (2R,3S)-3-(Formyl-hydroxyamino)-2-(5-methyl-2-thiophenemethyl)hexanoic Acid [(1S)-2-(2-Pyridinecarbonylamino)-1-(1,3-thiazol-2-ylcarbamoyl)-1-ethyl]amide |
| 166 | (2R,3S)-3-(Formyl-hydroxyamino)-2-(5-methyl-2-thiophenemethyl)hexanoic Acid [(1S)-3-(4-Morpholinecarbonyl)-1-(1,3-thiazol-2-ylcarbamoyl)-1-propyl]amide |

TABLE 2A-continued

| Example | Chemical Name |
|---|---|
| 167 | (2R,3S)-3-(Formyl-hydroxyamino)-2-(5-methyl-2-thiophenemethyl)hexanoic Acid [(1S)-3-Methyl-benzylaminocarbonyl-1-(pyridine-2-ylcarbamoyl)-1-propyl]amide |
| 168 | (2R,3S)-3-(Formyl-hydroxyamino)-2-(5-methyl-2-thiophenemethyl)hexanoic Acid [(1S)-2,2-Dimethyl-1-(6-aminopyridine-2-ylcarbamoyl)-1-propyl]amide |
| 169 | (2R,3S)-3-(Formyl-hydroxyamino)-2-(5-methyl-2-thiophenemethyl)hexanoic Acid [(1S)-2,2-Dimethyl-1-(4-aminopyridine-3-ylcarbamoyl)-1-propyl]amide |
| 170 | (2R,3S)-3-(Formyl-hydroxyamino)-2-(5-methyl-2-thiophenemethyl)hexanoic Acid [(1S)-2,2-Dimethyl-1-(3-aminopyridine-2-ylcarbamoyl)-1-propyl]amide |
| 171 | (2R,3S)-3-(Formyl-hydroxyamino)-2-(5-methyl-2-thiophenemethyl)hexanoic Acid [(1S)-2,2-Dimethyl-4-(2-Pyridylcarbonylamino)-1-(pyridine-2-ylcarbamoyl)-1-butyl]amide |
| 172 | (2R,3S)-3-(Formyl-hydroxyamino)-2-(3-phenyl-2-methyl-1-propyl)-4-methylpentanoic Acid [(1S)-2-(3-Pyridyl)-1-(1,3-thiazol-2-ylcarbamoyl)-1-ethyl]amide |
| 173 | (2R,3S)-3-(Formyl-hydroxyamino)-2-(5-methyl-2-thiophenemethyl)hexanoic Acid [(1S)-4-(Imino-(2,3,6-trimethyl-4-methoxybenzenesulfonylamino)methylamino)-1-(1,3-thiazol-2-ylcarbamoyl)-1-butyl]amide |
| 174 | (2R,3S)-3-(Formyl-hydroxyamino)-2-(5-methyl-2-thiophenemethyl)hexanoic Acid [(1S)-3-Guanidinesulfonyl-1-(1,3-thiazol-2-ylcarbamoyl)-1-propyl]amide |
| 175 | (2R,3S)-3-(Formyl-hydroxyamino)-2-(3-(3-pyridyl)-1-propyl)hexanoic Acid [(1S)-5-Ethoxycarbonylamino-1-(1,3-thiazol-2-ylcarbamoyl)-1-pentyl]amide |
| 176 | (2R,3S)-3-(Formyl-hydroxyamino)-2-(3-(5-methyl-2-thiophenemethyl)hexanoic Acid [(1S)-3-(4-Ethoxycarbonyl-1-piperazinecarbonyl)-1-(1,3-thiazol-2-ylcarbamoyl)-1-propyl]amide |
| 177 | (2R,3S)-3-(Formyl-hydroxyamino)-2-(5-methyl-2-thiophenemethyl)hexanoic Acid [(1S-3-(Methyl-methoxyaminocarbonyl)-1-(1,3-thiazol-2-ylcarbamoyl)-1-propyl]amide |
| 178 | (2R,3S)-3-(Formyl-hydroxyamino)-2-(3-phenyl-1-propyl)-4-methylpentanoic Acid [(1S,2S)-2-Methyl-1-(1,3-thiazol-2-ylcarbamoyl)-1-butyl]amide |
| 179 | (2R,3S)-3-(Formyl-hydroxyamino)-2-(3-phenyl-1-propyl)-4-methylpentanoic Acid [(1S,2S)-2-Methyl-1-(pyridine-2-ylcarbamoyl)-1-butyl]amide |
| 180 | (2R,3S)-3-(Formyl-hydroxyamino)-2-benzylhexanoic Acid [(1S,2S)-2-Methyl-1-(pyridine-2-ylcarbamoyl)-1-butyl]amide |
| 181 | (2R,3S)-3-(Formyl-hydroxyamino)-2-(3-(4-chlorophenyl)-1-propyl)-4-methylpentanoic Acid [(1S)-2,2-Dimethyl-1-(pyridine-3-ylcarbamoyl)-1-propyl]amide |
| 182 | (2R,3S)-3-(Formyl-hydroxyamino)-2-(3-(thiophene-2-yl)-1-propyl)butanoic Acid [(1S)-2,2-Dimethyl-1-(pyridine-3-ylcarbamoyl)-1-propyl]amide |
| 183 | (2R,3S)-3-(Formyl-hydroxyamino)-2-(3-phenyl-1-propyl)-6,6,6-trifluorohexanoic Acid [(1S)-2,2-Dimethyl-1-(1,3-thiazol-2-ylcarbamoyl)-1-propyl]amide |
| 184 | (2R,3S)-3-(Formyl-hydroxyamino)-2-(3-phenyl-1-propyl)-6,6,6-trifluorohexanoic Acid [(1S)-2-Methyl-1-(1,3-thiazol-2-ylcarbamoyl)-1-propyl]amide |
| 185 | (2R,3S)-3-(Formyl-hydroxyamino)-2-(3-phenyl-1-propyl)-6,6,6-trifluorohexanoic Acid [(1S,2R)-2-Methoxy-1-(1,3-thiazol-2-ylcarbamoyl)-1-propyl]amide |
| 186 | (2R,3S)-3-(Formyl-hydroxyamino)-2-(3-phenyl-1-propyl)-6,6,6-trifluorohexanoic Acid [(1S,2S)-2-Methyl-1-(pyridine-2-ylcarbamoyl)-1-butyl]amide |

TABLE 2B

| Example | Chemical Name |
|---|---|
| 187 | (2R,3S)-3-(Formyl-hydroxyamino)-2-(3-phenyl-1-propyl)butanoic Acid [1S,2R)-2-Methoxy-1-(pyridine-3-ylcarbamoyl)-1-propyl]amide |
| 188 | (2R,3S)-3-(Formyl-hydroxyamino)-2-(3-phenyl-1-propyl)butanoic Acid [(1S,2S)-2-Methyl-1-(pyridine-3-ylcarbamoyl-1-butyl]amide |
| 189 | (2R,3S)-3-(Formyl-hydroxyamino)-2-(3-(4-trifluoromethylphenyl)-1-propyl)butanoic Acid [(1S)-2,2-Dimethyl-1-(pyridine-3-ylcarbamoyl)-1-propyl]amide |
| 190 | (2R,3S)-3-(Formyl-hydroxyamino)-2-(3-(4-methylphenyl)-1-propyl)butanoic Acid [(1S)-2,2-Dimethyl-1-(pyridine-3-ylcarbamoyl)-1-propyl]amide |
| 191 | (2R,3S)-3-(Formyl-hydroxyamino)-2-(3-(4-tert-butylphenyl)-1-propyl)butanoic Acid [(1S)-2,2-Dimethyl-1-(pyridine-3-ylcarbamoyl)-1-propyl]amide |
| 192 | (2R,3S)-3-(Formyl-hydroxyamino)-2-(5-phenyl-1-pentyl)butanoic Acid [(1S)-2,2-Dimethyl-1-(pyridine-3-ylcarbamoyl)-1-propyl]amide |
| 193 | (2R,3S)-3-(Formyl-hydroxyamino)-2-(3-(4-methoxyphenyl)-1-propyl)butanoic Acid [(1S)-2,2-Dimethyl-1-(pyridine-3-ylcarbamoyl)-1-propyl]amide |

TABLE 2B-continued

| Example | Chemical Name |
|---|---|
| 194 | (2R,3S)-3-(Formyl-hydroxyamino)-2-(4-phenyl-1-butyl)butanoic Acid [(1S)-2,2-Dimethyl-1-(pyridine-3-ylcarbamoyl)-1-propyl]amide |
| 195 | (2R,3S)-3-(Formyl-hydroxyamino)-2-(3-(4-chlorophenyl)-1-propyl)butanoic Acid [(1S)-2,2-Dimethyl-1-(pyridine-3-ylcarbamoyl)-1-propyl]amide |
| 196 | (2R,3S)-3-(Formyl-hydroxyamino)-2-(3-(4-phenoxyphenyl)-1-propyl)butanoic Acid [(1S)-2,2-Dimethyl-1-(pyridine-3-ylcarbamoyl)-1-propyl]amide |
| 197 | (2R,3S)-3-(Formyl-hydroxyamino)-2-(3-phenyl-1-propyl)-6,6,6-trifluorohexanoic Acid [(1S)-Cyclohexyl(1,3-thiazol-2-ylcarbamoyl)methyl]amide |

Preferred embodiments of the invention include compounds of general formula (II) where $R_1$ is methyl, trifluoromethyl, ethyl, isopropyl, n-propyl, tert-butyl, 3-methoxycyclopentyl, furan-2-ethynyl, 4-methyl-1-pentyl, 2-thiophenesulfanylmethyl, 4-trifluoromethylcyclohexyl, 3-aminophenoxymethyl, 3-(4-morpholine)-1-propyl, 2-(3-tetrazolyl)-1-ethyl, 2-(3-pyridyl)-1-ethyl, 2-(3-furyl)-1-ethyl, 2-(2-thiazolyl)-1-ethyl, 3,3,3-trifluoro-1-propyl, 4,4,4-trifluoro-1-butyl, 2-(4-trifluorophenyl)-1-ethyl, thiophene-3-ethynyl, 2-nitrophenoxymethyl, 3-nitrophenoxymethyl, ethynyl, 2-propynyl, 2-butynyl, phenylethynyl, or vinyl;

$R_2$ is 5-methylthiophene-2-methyl, 2-furanmethyl, thiophene-2-methyl, benzothiophene-2-methyl, benzofuran-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(benzofuran-3-yl)-1-propyl, 3-(benzothiophene-3-yl)-1-propyl, 3-(furan-2-yl)-1-propyl, 3-(2-thiazolyl)-1-propyl, 3-(pyrimidin-2-yl)-1-propyl, 3-phenyl-2-ethyl-1-propyl, benzyloxymethyl, 2-benzyloxy-1-ethyl, 3-(3-pyridyl)-1-propyl, 2-phenyl-1-ethyl, 3-benzyloxy-1-propyl. 4-phenylcyclohexylmethyl, 3-(furan-3-yl)-1-propyl, 1,2,3,4-tetrahydronaphthalene-2-methyl, 4-biphenylpropyl, 3-phenyl-1-butyl, 2,3-dihydrobenzo[1,4]dioxine-2-methyl, 2-naphthylmethyl, chroman-2-methyl, 3-phenyl-2-ethyl-2-propene-1-yl, 3-biphenyl, 4-phenyl-3-methyl-2-butyl, 4-(3-thiophenyl)-2-butyl, benzothiophene-3-methyl, benzoxazole-2-methyl, 4-(3-furyl)-2-butyl, 3-(4-chlorophenyl)-1-propyl, 3-phenoxyphenyl-1-propyl, or benzyl;

$R_3$ is hydrogen, isobutyl, or methyl;

$R_4$ is tert-butyl, 1-propoxy-1-ethyl, 4-(benzyloxycarbonylamino)-1-butyl, 2-(2-(benzyloxycarbonylamino)-1-ethylsulfanyl)-2-propyl, 4-(2-pyridylcarbonylamino)-2-methyl-2-butyl, 4-isobutoxycarbonylamino-1-butyl, 3-pyridylmethyl, 3-(2-thiophenecarbonylamino)-2-methyl-2-propyl, 4-propoxycarbonylamino-2-butyl, 4-(2-naphthylacetylamino)-1-butyl, 1-ethoxycarbonylamino-1-ethyl, 4-(2-pyridylcarbonylamino)-2-methyl-2-butyl, 3-(benzyloxycarbonylamino)-1-propyl, 1-methanesulfanyl-1-ethyl, 3-(2-pyridylcarbonylamino)-2-methyl-2-propyl, 3-(2-thiophenecarbonylamino)-2-propyl, 3-carbamoylamino-1-propyl, 4-(4-pyridylcarbonylamino)-2-methyl-2-butyl, 2-ethoxycarbonylamino-1-propyl, 4-bydroxybenzyl, 4-chlorobenzyl, 1-(tetrahydrofuran-3-yloxy)-1-ethyl, 1-methanesulfenyl-1-ethyl, 4-fluorobenzyl, 3-(imino-benzenesulfonylamino)-methylamino-1-propyl, 4-propoxycarbonylamino-1-butyl, 3-(imino-(2,3,6-trimethyl-4-methoxybenzenesulfonylamino))-methylamino-1-propyl, 2-(2-(1,3,4-thiadiazol)ylaminosulfonyl)-1-ethyl, 3-methylcarbamoylamino-1-propyl, 4-benzyloxycarbonylaminobenzyl, isopropyl, 2-(3-pyridylcarbonylamino)-1-ethyl, 1,1-dimethyl-1-propyl, 2-(2-thiophene)-1-ethyl, cyclohexyl, 3-phenylcarbamoylamino-1-propyl, 4-cyclopentylacetylamino-1-butyl, 4-(3-methoxybenzoylamino)-1-butyl, 4-ethoxycarbonylamino-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, 2-(methoxymethylaminocarbonyl)-1-ethyl, 2-(4-ethoxycarbonyl-1-piperazinecarbonyl)-1-ethyl, 2-guanidinesulfonyl-1-ethyl, 2-methyl-4-(2-pyridylcarbonylamino)-2-butyl, 2-(methylbenzylaminocarbonyl)-1-ethyl, 2-(4-morpholinecarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, phenyl, 2-methyl-1-propyl, or 2-phenyl-1-ethyl;

$R_5$ is hydrogen, methyl, ethyl, or propyl; and $R_6$ is 2-thiazolyl, 2-pyridyl, 2-pyrimidinyl, 2-(1,3,4-thiadiazolyl), 3-(5-methylisoxazolyl), 3-pyridyl, 3-indolyl, 2-(5-methylthiazolyl), 3-hydroxy-2-pyridyl, 2-(5-ethanesulfanyl-1,3,4-thiadiazolyl), 2-benzothiazolyl, 6-methoxy-2-benzothiazolyl, 4-pyridyl, 2-pyrazinyl, 3-quinolinyl, 2-(5-methyl-1,3,4-thiadiazolyl), 6-amino-3-pyridyl, 6-amino-2-pyridyl, 4-amino-3-pyridyl, or 3-amino-2-pyridyl.

Other preferred embodiments of the invention include compounds of general formula (II) where where $R_1$, $R_3$, $R_4$, $R_5$ and $R_6$ are as defined above and $R_2$ is 5-phenyl-1-pentyl, 3-(4-trifluorophenyl)-1-propyl, 3-(4-methylphenyl)-1-propyl, 3-(4-phenoxyphenyl)-1-propyl, 3-(4-tert-butylphenyl)-1-propyl, 3-(4-methoxyphenyl)-1-propyl, 3-(4-trifluorophenyl)-1-propyl, or 3-(3-phenoxyphenyl)-1-propyl;

Particularly preferred embodiments of the invention include compounds of general formula (II) where $R_1$ is methyl, ethyl, n-propyl, isopropyl, 4-methyl-1-pentyl, 2-thiophenesulfanylmethyl, 3-aminophenoxymethyl, 2-(3-tetrazolyl)-1-ethyl, 2-(3- pyridyl)-1-ethyl, 2-(3-furyl)-1-ethyl, 2-(2-thiazolyl)-1-ethyl, 3,3,3-trifluoro-1-propyl, 2-(4-trifluorophenyl)-1-ethyl, thiophene-3-ethynyl, 2-nitrophenoxymethyl, 3-nitrophenoxymethyl, or vinyl;

$R_2$ is 5-methylthiophene-2-methyl, 2-furanmethyl, thiophene-2-methyl, benzothiophene-2-methyl, benzofuran-2-methyl, 4-fluorobenzyl, 3-phenyl-1-propyl, 3-phenyl-2-methyl-1-propyl, 3-(2-pyridyl)-1-propyl, 3-(thiophene-2-yl)-1-propyl, 4-phenyl-1-butyl, 3-phenyl-2-propene-1-yl, 3-(benzofuran-3-yl)-1-propyl, 3-(benzothiophene-3-yl)-1-propyl, 3-(furan-2-yl)-1-propyl, 3-(2-thiazolyl)-1-propyl, 3-(pyrimidin-2-yl)-1-propyl, 3-phenyl-2-ethyl-1-propyl, benzyloxymethyl, 2-benzyloxy-1-ethyl, 3-(3-pyridyl)-1-propyl, 2-phenyl-1-ethyl, 3-benzyloxy-1-propyl, 4-phenylcyclohexylmethyl, 3-(furan-3-yl)-1-propyl, 1,2,3,4-tetrahydronaphthalene-2-methyl, 3-phenyl-1-butyl, 2,3-dihydrobenzo[1,4]dioxine-2-methyl, 2-naphthylmethyl, chroman-2-methyl, 3-phenyl-2-methyl-2-propene-1-yl, 4-phenyl-3-methyl-2-butyl, 4-(3-thiophenyl)-2-butyl, benzothiophene-3-methyl, benzoxazole-2-methyl, 4-(3-furyl)-2-butyl, 3-(4-chlorophenyl)-1-propyl, or benzyl;

$R_3$ is hydrogen;

$R_4$ is tert-butyl, 4-(benzyloxycarbonylamino)-1-butyl, 2-(2-(benzyloxycarbonylamino)-1-ethylsulfanyl)-2-propyl, 3-pyridylmethyl, 4-(2-naphthylacetylamino)-1-butyl, 3-(benzyloxycarbonylamino)-1-propyl, 3-carbamoylamino-1-propyl, 4-hydroxybenzyl, 4-chlorobenzyl, 4-fluorobenzyl, 3-(imino-(2,3,6-trimethyl-4-methoxybenzenesulfonylamino))-methylamino-1-propyl, 4-benzyloxycarbonylaminobenzyl, isopropyl, cyclohexyl, 4-cyclopentylacetylamino-1-butyl, 4-(3-methoxybenzoylamino)-1-butyl, 4-ethoxycarbonylamino-1-butyl, 2-(2-(ethoxycarbonylamino)-1-ethylsulfanyl)-2-propyl, 2-butyl, 1-methoxy-1-ethyl, 1-hydroxy-1-ethyl, 2-(methoxy methylaminocarbonyl)-1-ethyl, 2-(4-ethoxycarbonyl-1-piperazinecarbonyl)-1-ethyl, 2-guanidinesulfonyl-1-ethyl, 2-methyl-4-(2-pyridylcarbonylamino)-2-butyl, 2-(methyl benzylaminocarbonyl)-1-ethyl, 2-(4-morpholinecarbonyl)-1-ethyl, 2-pyridylcarbonylaminomethyl, acetylaminomethyl, 1-isobutoxy-1-ethyl, carbamoylaminomethyl, dimethylaminocarbonylmethyl, 2-dimethylaminosulfonyl-1-ethyl, 2-methanesulfanyl-2-propyl, 2-hydroxy-2-propyl, 4-(2-pyridylcarbonylamino-1-butyl, 2-(dimethylaminocarbonyl)-1-ethyl, 2-methanesulfonyl-1-ethyl, 1-(2-pyridylmethoxy)-1-ethyl, 1-benzyloxy-1-ethyl, phenyl, 2-methyl-1-propyl, or 2-phenyl-1-ethyl;

$R_5$ is hydrogen; and $R_6$ is 2-thiazolyl, 2-pyridyl, 2-pyrimidinyl, 2-(1,3,4-thiadiazolyl), 3-(5-methylisoxazolyl), 3-pyridyl, 2-(5-methylthiazolyl), 3-hydroxy-2-pyridyl, 2-(5-ethanesulfanyl-1,3,4-thiadiazolyl), 4-pyridyl, 2-pyrazinyl, 2-(5-methyl-1,3,4-thiadiazolyl), 6-amino-3-pyridyl, 6-amino-2-pyridyl, 4-amino-3-pyridyl, or 3-amino-2-pyridyl.

Other particularly preferred embodiments of the invention include compounds of general formula (II) where where $R_1$, $R_3$, $R_4$, $R_5$ and $R_6$ are as defined above and $R_2$ is 5-phenyl-1-pentyl, 3-(4-trifluorophenyl)-1-propyl, 3-(4-methylphenyl)-1-propyl, or 3-(4-phenoxyphenyl)-1-propyl;

More particularly preferred embodiments of the invention include compounds of general formula (II) where $R_1$ is methyl, n-propyl, isopropyl, ethyl, or 3,3,3-trifluoro-1-propyl;

$R_2$ is 5-methylthiophene-2-methyl, 3-phenyl-1-propyl, 4-phenyl-1-butyl, 2-phenyl-1-ethyl, 4-phenylcyclohexylmethyl, 3-(4-chlorophenyl)-1-propyl, or benzyl;

$R_3$ is hydrogen;

$R_4$ is tert-butyl, isopropyl, 2-butyl, 1-methoxy-1-ethyl, 1-hydroxy-1-ethyl, 2-methanesulfanyl-2-propyl, or 2-hydroxy-2-propyl;

$R_5$ is hydrogen; and $R_6$ is 2-thiazolyl, 2-pyridyl, 3-pyridyl, or 4-pyridyl.;

Other more particularly preferred embodiments of the invention include compounds of general formula (II) where where $R_1$, $R_3$, $R_4$ and $R_5$ are as defined above; $R_2$ is 5-phenyl-1-pentyl, 3-(4-trifluorophenyl)-1-propyl, 3-(4-methylphenyl)-1-propyl, or 3-(4-phenoxyphenyl)-1-propyl; and $R_6$ is 2-(1,3,4-thiadiazolyl);

The compounds of the present invention are inhibitors of matrix metalloproteases, TNF converting enzyme, and TNF activity from whole cells. The compounds of the present invention may also inhibit shedding of pathologically significant cell surface protein ectodomains. The compounds of the present invention may also inhibit CD23 proteolysis. The invention described herein is additionally directed to pharmaceutical compositions and methods of inhibiting matrix metalloprotease and/or TNF activity and/or CD23 proteolytic fragment activity in a mammal, which methods comprise administering to a mammal in need of a therapeutically defined amount of a compound of formula (I) or (II), defined above, as a single or polymorphic crystalline form or forms, an amorphous form, a single enantiomer, a racemic mixture, a single stereoisomer, a mixture of stereoisomers, a single diastereoisomer, a mixture of diastereomers, a solvate, a pharmaceutically acceptable salt, a solvate, a prodrug, a biohydrolyzable ester, or a biohydrolyzable amide thereof.

According to a further aspect of the present invention there is provided a compound of formula (II) as defined above or a pharmaceutically acceptable salt, solvate, biohydrolyzable ester, biohydrolyzable amide, affinity reagent or prodrug thereof.

Thus, the present invention provides a method of inhibiting a matrix metalloprotease, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit a matrix metalloprotease. A matrix metalloprotease-inhibiting amount can be an amount that reduces or inhibits a matrix metalloprotease activity in the subject.

According to a further aspect of the invention there is provided the use of a compound of the present invention in the preparation of a medicament to inhibit a matrix metalloprotease.

The present invention further provides a method of inhibiting the intracellular release of tumor necrosis factor alpha, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit cellular release of mature tumor necrosis factor. An amount sufficient to inhibit cellular release of mature tumor necrosis factor can be an amount that reduces or inhibits cellular release of mature tumor necrosis factor in the subject.

According to a further aspect of the invention there is provided the use of a compound of the present invention in the preparation of a medicament to inhibit the cellular release of mature tumor necrosis factor alpha.

Also provided is a method of inhibition of shedding of cell surface protein ectodomains, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit shedding of cell surface protein ectodomains. An amount sufficient to inhibit shedding of cell surface protein ectodomains can be an amount that reduces or inhibits shedding of one or more cell surface protein ectodomains, such as L-selectin, fibronectin, thyrotropin stimulating hormone receptor, transforming growth factor alpha precursor, low density lipoprotein receptor, beta amyloid precursor protein, interleukin-6 receptor alpha subunit, Fas ligand, CD40 ligand, epidermal growth factor receptor, macrophage colony stimulating factor, interleukin-1 receptor type II, CD30, and tumor necrosis factor receptors type I and II, in the subject.

According to a further aspect of the invention there is provided the use of a compound of the present invention in the preparation of a medicament to inhibit the shedding of cell surface protein ectodomains.

A method of inhibiting CD23 proteolysis, comprising the step of administering to a mammal in need thereof a pharmacologically effective amount of a compound of the present invention. The invention further provides a pharmaceutical composition comprising a pharmaceutically acceptable carrier and a pharmacologically effective amount of a compound of the present invention sufficient to inhibit CD23 proteolysis. An amount sufficient to inhibit CD23 proteolysis can be an amount that reduces or inhibits CD23 proteolysis in the subject.

According to a further aspect of the invention there is provided the use of a compound of the present invention in the preparation of a medicament to inhibit CD23 proteolysis.

Additionally provided is a pharmaceutical composition comprising a pharmaceutically acceptable carrier and a pharmacologically effective amount of a compound of the present invention sufficient to decrease, or inhibit, a malignant growth.

According to a further aspect of the invention there is provided the use of a compound of the present invention in the preparation of a medicament to decrease or inhibit a malignant growth.

Further, the present invention provides a pharmaceutical composition comprising a pharmaceutically acceptable carrier and a pharmacologically effective amount of a compound of the present invention sufficient to treat arthritis. Such an amount can be an amount that relieves, i.e., reduces or eliminates, one or more physiologic characteristic of arthritis.

According to a further aspect of the invention there is provided the use of a compound of the present invention in the preparation of a medicament to treat arthritis.

Also provided is a pharmaceutical composition comprising a pharmaceutically acceptable carrier and a pharmacologically effective amount of a compound of the present invention sufficient to treat diabetes. Such an amount can be an amount that reduces or eliminates one or more of the complications associated with diabetes. Additionally, the present invention contemplates treating any of these diseases/conditions in a subject by administering to the subject the recited pharmaceutical composition.

According to a further aspect of the invention there is provided the use of a compound of the present invention in the preparation of a medicament to treat diabetes.

The compounds of the present invention can be administered to any mammal in need of inhibition of matrix metalloprotease activity, CD23 proteolysis, shedding of cell surface protein ectodomains and/or TNF activity. Such mammals can include, for example, horses, cows, sheep, pigs, mice, dogs, cats, primates such as chimpanzees, gorillas, rhesus monkeys, and, most preferably humans.

Certain examples of the invention also are orally bioavailable in animals and possess oral activity in animal models of disease.

Salts encompassed within the term "pharmaceutically acceptable salts" refer to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrocloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate.

Other salts which are not pharmaceutically acceptable may be useful in the preparation of compounds of formula (I) or (II) and these form a further aspect of the invention.

Also included within the scope of the invention are the individual enantiomers of the compounds represented by formula (I) or (II) above as well as any wholly or partially racemic mixtures thereof. The present invention also covers the individual enantiomers of the compounds represented by formula above as mixtures with diastereoisomers thereof in which one or more of the three stereocenters are inverted.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkyl" as used herein include, but are not limited to, n-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkenylene" refers to an straight or branched chain divalent hydrocarbon radical having from two to ten carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed.

As used herein, the term "alkynylene" refers to a straight or branched chain divalent hydrocarbon radical having from two to ten carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "alkynylene" as used herein include, but are not limited to, ethyne-1,2-diyl, propyne-1,3-diyl, and the like.

As used herein, "cycloalkyl" refers to a alicyclic hydrocarbon group with one or more degrees of unsaturation, having from three to twelve carton atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

As used herein, the term "cycloalkylene" refers to an non-aromatic alicyclic divalent hydrocarbon radical having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

As used herein, the term "cycloalkenyl" refers to a substituted alicyclic hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 1-cyclopentene-3-yl, 1-cyclohexene-3-yl, 1-cycloheptene-4-yl, and the like.

As used herein, the term "cycloalkenylene" refers to a substituted alicyclic divalent hydrocarbon radical having from three to twelve carbon atoms and at least one carbon-carbon double bond in the ring system, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkenylene" as used herein include, but are not limited to, 4,5-cyclopentene-1,3-diyl, 3,4-cyclohexene-1,1-diyl, and the like.

As used herein, the term "heterocyclic" or the term "heterocyclyl" refers to a three to twelve-membered heterocyclic ring having one or more degrees of unsaturation containing one or more heteroatomic substitutions selected from S, SO, $SO_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alky, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein, the term "heterocyclylene" refers to a three to twelve-membered heterocyclic ring diradical having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, and the like.

As used herein, the term "aryl" refers to a benzene ring or to an optionally substituted benzene ring system fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

As used herein, the term "arylene" refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of "arylene" include, but are not limited to, benzene-1,4-diyl, naphthalene-1,8-diyl, anthracene-1,4-diyl, and the like.

As used herein, the term "heteroaryl" refers to a five- to seven-membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, and indazole, and the like.

As used herein, the term "heteroarylene" refers to a five- to seven-membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "aryloxy" refers to the group $R_aO$—, where $R_a$ is aryl.

As used herein, the term "heteroaryloxy" refers to the group $R_aO$—, where $R_a$ is heteroaryl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "akynaylosufany" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alky, alkenyl, alkynyl, cycloalkyl, cycloalkenyl, or heterocyclyl.

As used herein, the term "aroyl" refers to the group $R_aC(O)$—, where $R_a$ is aryl.

As used herein, the termn "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O-$, where $R_a$ is aryl.

As used herein, the term "heteroaroyloxy" refers to the group $R_aC(O)O-$, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the terms "contain" or "containing" can refer to in-line substitutions at any position along the above-defined alkyl, alkenyl, alkynyl or cycloalkyl substituents with one or more of any of O, S, SO, $SO_2$, N, or N-alkyl, including, for example, $-CH_2-O-CH_2-$, $-CH_2-SO_2-CH_2-$, $-CH_2-NH-CH_3$ and so forth.

As used herein, the term "solvate" is a complex of variable stoichiometry formed by a solute (in this invention, a compound of formula (I) or (II)) and a solvent. Such solvents for the purpose of the invention may not interfere with the biological activity of the solute. Solvents may be, by way of example, water, ethanol, or acetic acid.

As used herein, the term "biohydrolyzable ester" is an ester of a drug substance (in this invention, a compound of general formula (I) or (II) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) or (II) in plasma. Many examples of such are known in the art and include by way of example lower alkyl esters, lower acyloxy-alkyl esters, lower alkoxyacyloxyalkyl esters, alkoxyacyloxy esters, alkyl acylamino alkyl esters, and choline esters. An example of such a biohydrolyzable ester applied to the general formula (II) is illustrated below in general formula (III).

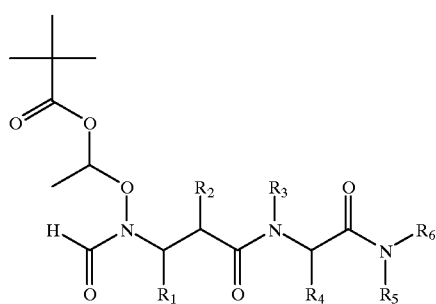

(III)

As used herein, the term "biohydrolyzable amide" is an amide of a drug substance (in this invention, a compound of general formula (I) or (II) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) or (II) in plasma. Many examples of such are known in the art and include by way of example lower alkyl amides, a-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) or (II): for example, the lactam formed by a carboxylic group in $R_2$ and an amine in $R_4$, and b) compounds which may be oxidized or reduced biologically at a given functional group to yield drug substances of formula (I) or (II) . Examples of these functional groups are, but are not limited to, 1,4-dihydropyridine, N-alkylcarbonyl-1,4-dihydropyridine, 1,4-cyclohexadiene, tert-butyl, and the like.

As used herein, the term "affinity reagent" is a group attached to the compound of formula (I) or (II) which does not affect its in vitro biological activity, allowing the compound to bind to a target, yet such a group binds strongly to a third component allowing a) characterization of the target as to localization within a cell or other organism component, perhaps by visualization by fluorescence or radiography, or b) facile separation of the target from an unknown mixture of targets, whether proteinaceous or not proteinaceous. An example of an affinity reagent according to b) would be biotin either directly attached to (I) or (II) or linked with a spacer of one to 50 atoms selected from the group consisting of C, H, O, N, S, or P in any combination. An example of an affinity reagent according to a) above would be fluorescein, either directly attached to (I) or (II) or linked with a spacer of one to 50 atoms selected from the group consisting of C, H, O, N, S, or P in any combination.

The term "pharmacologically effective amount" shall mean that amount of a drug or pharmaceutical agent that will elicit the biological or medical response of a tissue, system, animal or human that is being sought by a researcher or clinician. This amount can be a therapeutically effective amount.

Whenever the terms "alkyl" or "aryl" or either of their prefix roots appear in a name of a substituent (e.g. arylalkoxyaryloxy) they shall be interpreted as including those limitations given above for "alkyl" and "aryl". Alkyl or cycloalkyl substituents shall be recognized as being functionally equivalent to those having one or more degrees of unsaturation. Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent $=O$.

As used herein, the term "halogen" or "halo" shall include iodine, bromine, chlorine and fluorine.

As used herein, the term "mercapto" shall refer to the substituent $-SH$.

As used herein, the term "carboxy" shall refer to the substituent $-COOH$.

As used herein, the term "cyano" shall refer to the substituent $-CN$.

As used herein, the term "aminosulfonyl" shall refer to the substituent $-SO_2NH_2$.

As used herein, the term "carbamoyl" shall refer to the substituent $-C(O)NH_2$.

As used herein, the term "sulfanyl" shall refer to the substituent $-S-$.

As used herein, the term "sulfenyl" shall refer to the substituent $-S(O)-$.

As used herein, the term "sulfonyl" shall refer to the substituent —S(O)$_2$—.

The compounds of formula (I) and (II) can be prepared readily according to the following reaction Schemes (in which all variables are as defined before) and Examples or modifications thereof using readily available starting materials, reagents and conventional synthesis procedures. In these reactions, it is also possible to make use of variants which are themselves known to those of ordinary skill in this art, but are not mentioned in greater detail.

The most preferred compounds of the invention are any or all of those specifically set forth in these examples. These compounds are not, however, to be construed as forming the only genus that is considered as the invention, and any combination of the compounds or their moieties may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless noted otherwise.

Abbreviations used in the Examples are as follows:

| | |
|---|---|
| g = | grams |
| mg = | milligrams |
| L = | liters |
| mL = | milliliters |
| psi = | pounds per square inch |
| M = | molar |
| N = | normal |
| mM = | millimolar |
| i.v. = | intravenous |
| p.o. = | per oral |
| s.c. = | subcutaneous |
| Hz = | hertz |
| mol = | moles |
| mmol = | millimoles |
| mbar = | millibar |
| rt = | room temperature |
| min = | minutes |
| h = | hours |
| mp = | melting point |
| TLC = | thin layer chromatography |
| R$_f$ = | relative TLC mobility |
| MS = | mass spectrometry |
| NMR = | nuclear magnetic resonance spectroscopy |
| APCI = | atmospheric pressure chemical ionization |
| ESI = | electrospray ionization |
| m/z = | mass to charge ratio |
| t$_{96}$ = | retention time |
| ether = | diethyl ether |
| MeOH = | methanol |
| EtOAc = | ethyl acetate |
| TEA = | triethylamine |
| DIEA = | diisopropylethylamine |
| BOP = | (1-benzotriazolyloxy)tris(dimethylamino) phosphonium hexafluorophosphate |
| THF = | tetrahydrofuran |
| DMF = | N,N-dimethylformamide |
| DBU = | 1,8-diazabicyclo[5.4.0]undec-7-ene |
| DMSO = | dimethylsulfoxide |
| LAH = | lithium aluminum hydride |
| TFA = | trifluoroacetic acid |
| EDC = | 1-ethyl-3-(3-dimethylaminopropyl)-carbodiimide hydrochloride |
| HOBt = | 1-hydroxybenzotriazole |
| LDA = | lithium diisopropylamide |
| THP = | tetrahydropyranyl |
| NMM = | N-methylmorpholine, 4-methylmorpholine |
| HMPA = | hexamethylphosphonc triamide |
| DMPU = | 1,3-dimethypropylene urea |
| d = | days |
| min = | minutes |

-continued

| | |
|---|---|
| ppm = | parts per million |
| kD = | kiloDalton |
| LPS = | lipopolysaccharide |
| PMA = | phorbol myristate acetate |
| SPA = | scintillation proximity assay |
| EDTA = | ethylenediamine tetraacetic acid |
| FBS = | fetal bovine serum |
| PBS = | phosphate buffered saline solution |
| ELISA = | enzyme - linked immunosorbent assay |

Several of the following examples represent pairs of stereoisomers which were separated as diastereoisomers but were not identified therein. Determination and/or preparation of the R and S isomers can advantageously be approached by stereoselective chemical methods, see "Advanced Organic Chemistry", Carey and Sundberg, 3rd edition, Plenum Press, 1990, 596, by analytical methods such as X-ray crystallography, or by determination of biological activity and subsequent correlation to biologically active compounds of known stereochemistry.

GENERAL REACTION SCHEMES

Compounds of the invention may be prepared by methods known in the art, where such a method is shown in reaction Scheme 1.

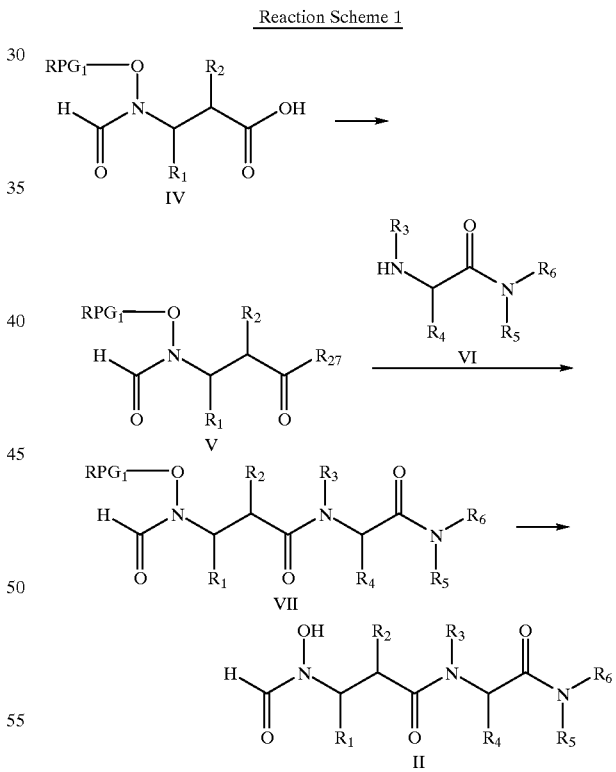

Reaction Scheme 1

R$_1$, R$_2$, R$_3$, R$_4$, R$_5$, and R$_6$ are as defined as for formula (II).
RPG$_1$ is selected from the group consisting of benzyl or 2-tetrahydropyranyl.
R$_{27}$ is chosen from the group consisting of hydroxyl, O—C$_6$F$_5$, or halogen.
When R$_{27}$ is hydroxyl, the conversion of (V) and (VI) to (VII) involves methods known in peptide chemistry; for example, the reaction may be conducted using HOBt in combination with a dehydrating agent such as dicyclohexylcarbodiimide in a suitable solvent, such as DMF. When $R_{27}$ is O—$C_6F_5$, the conversion of (IV) to (V) is conducted by treating (IV) in a suitable solvent such as dichloromethane with pentafluorophenyl trifluoroacetate in the presence of pyridine, or with EDC and pentafluorophenol in a suitable solvent such as dichloromethane. The displacement reaction to produce (VII) employing (VI) is carried out in the presence of a suitable solvent such as dioxane, THF, dichloromethane, or DMF, at a temperature of 0° C. to 140° C. The reaction is effected in the presence of an organic base such as NMM or TEA. It is understood that if $R_1$ in (VII) contains a monosubstituted alkenyl group, then addition of an aryl or heteroaryl bromide to (VII) in the presence of tetrakis(triphenylphosphine)palladium and TEA in DMF or THF affords the alkenylaryl or alkynylheteroaryl intermediate. If $R_1$ in (VII) contains a terminal alkynyl group, then addition of an aryl or heteroaryl bromide to (VII) in the presence of tetrakis(triphenylphosphine)palladium, CuI, and TEA in DMF or THF affords the alkynylaryl or alkynylheteroaryl intermediate. These $R_1$ substituents may be reduced with palladium on carbon and hydrogen to the saturated species. The removal of the $RPG_1$ group where $RPG_1$ is benzyl may be achieved by hydrogenation of (VII) with palladium on barium sulfate in a suitable solvent such as ethanol or THF, or, where $RPG_1$ is 2-tetrahydropyranyl, by hydrolysis with aqueous acetic acid at a temperature of 20° C. to 100° C.

Reaction Scheme 2 depicts the synthesis of a compound of formula (IV).

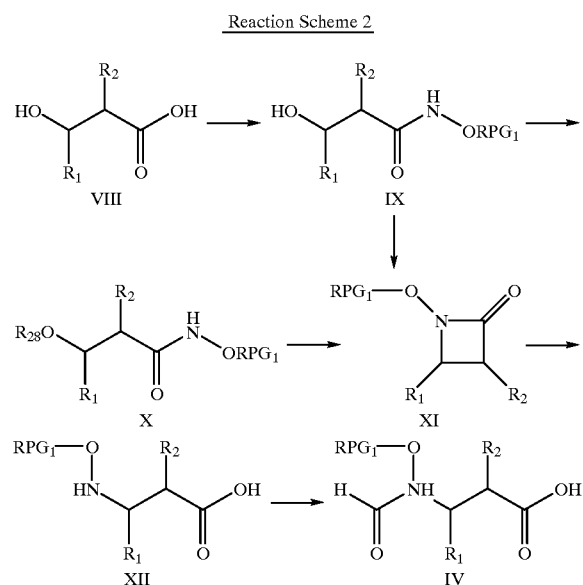

$R_1$ and $R_2$ are as defined for formula (II).
$R_{28}O$ is a nucleofugal group such as methanesulfonate or p-toluenesulfonate.
$RPG_1$ is defined as for reaction scheme 1.

The acid of formula (VIII) may be converted to the alcohol of formula (IX) by treatment with HOBt, O-benzylhydroxylamine hydrochloride or 2-tetrahydropyranyloxyamine, NMM, and a carbodiimide reagent such as EDC in a suitable solvent such as DMF. The alcohol of formula (IX) may be converted to (X) by treatment with methanesulfonyl chloride and pyridine in a suitable solvent such as dichloromethane. The conversion of (X) to (XI) may be conducted by treatment with potassium carbonate in a suitable solvent such as acetone or 2-butanone, at temperature of 20° C. to 90° C. Alternatively, (IX) may be converted directly to (XI) by treatment with triphenylphosphine and diethyl azodicarboxylate or another azodicarbonyl diester or diamide in a suitable solvent such as THF at a temperature of −78° C. to 50° C. (XI) where $R_1$ contains a primary or secondary hydroxyl group may be treated with a thiol, phenol, or heteroaryl species containing an NH group in the presence of triphenylphosphine and diethyl azodicarboxylate or another azodicarbonyl diester or diamide in a suitable solvent such as THF to afford the respective product of hydroxy displacement in (XI). The compound of formula (XI) may be converted to (XII) by treatment with an inorganic base such as sodium hydroxide in water or water in combination with a water-soluble organic cosolvent such as methanol or THF, followed by acidification with an acidic solution such as aqueous citric acid or aqueous sodium bisulfate. The compound of formula (XII) may be converted to (IV) by treatment with acetic anhydride and formic acid or by treatment with formic acetic anhydride in pyridine in the presence or absence of a suitable cosolvent such as dichloromethane.

An alternative route of preparation of compounds of formula (IX) is depicted in reaction Scheme 3.

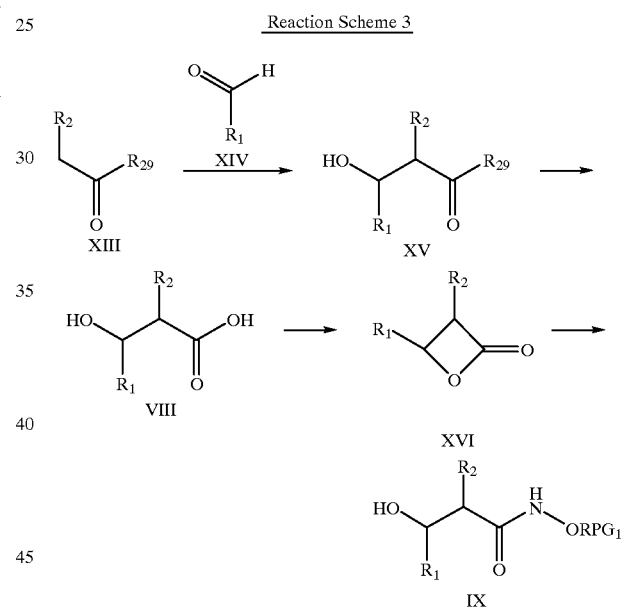

$R_1$ and $R_2$ are as defined as for formula (II).
$RPG_1$ is defined as for reaction scheme 1.
$R_{29}$ is chosen from the group consisting of lower alkoxy or oxazolidinon-1-yl, where the 4 and 5 positions of an oxazolidinon-1-yl group may be substituted with a lower alkyl, aryl, or lower alkylaryl group and where such an oxazolidinon-1-yl substituent may exist as a single stereoisomer or as a mixture of stereoisomers.

A carbonyl compound of formula (XIII), where $R_{29}$ is an alkoxy group such as methoxy or tert-butoxy, may be treated with a strong base such as LDA in a solvent such as THF at a temperature of from −78° C. to 0° C., followed by treatment with the aldehyde (XIV) to provide (XV). Where $R_{29}$ is a oxazolidinon-1-yl substituent, treatment of (XIII) with a Lewis acid such as di(n-butyl)boron trifluoromethanesulfonate in the presence of DIEA in a suitable solvent such as dichloromethane at a temperature of 0° C., followed by addition of the aldehyde (XIV) provides (XV).

Treatment of (XV) with aqueous base in the presence or absence of hydrogen peroxide affords (VIII) upon acidification. The acid (VIII) may be converted directly to (IX) as in reaction Scheme 2, or may be treated with a dehydrating agent such a p-toluenesulfonyl chloride in pyridine or with triphenylphosphine and diethyl azodicarboxylate in a suitable solvent such as THF, to afford the lactone (XVI). Treatment of the lactone (XVI) with H$_2$NO—RPG$_1$ in the presence of a Lewis acid such as trimethylaluminum in a suitable solvent such as toluene affords the alcohol (IX).

A preparation of compounds of general formula (IV) is depicted in reaction Scheme 4.

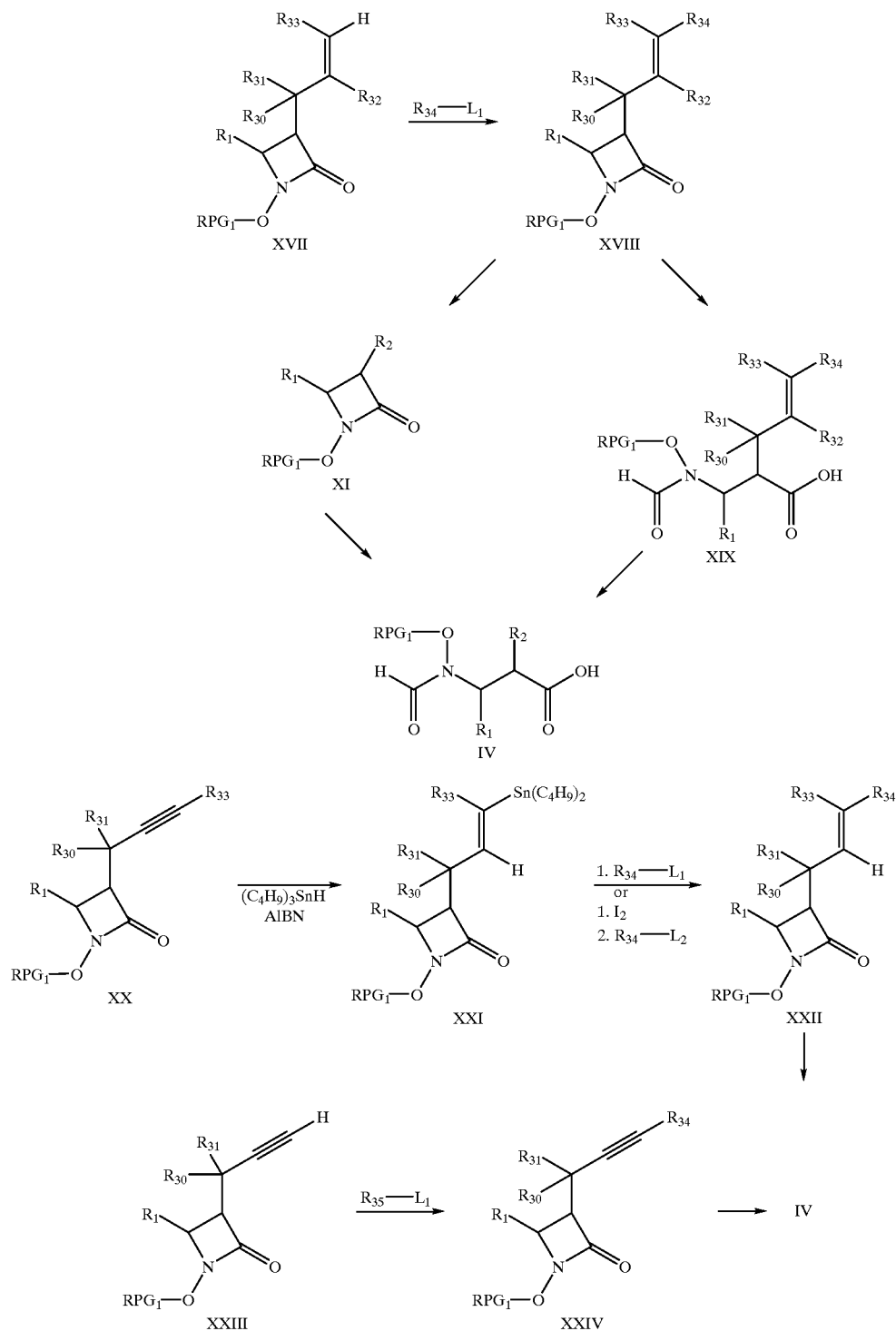

Reaction Scheme 4

$R_1$ and $R_2$ are as defined as for formula (II).

$R_{30}$, $R_{31}$, $R_{32}$, and $R_{33}$ may be, independently, alkyl, alkenyl, alkynyl, or hydrogen.

$R_{34}$ and $R_{35}$ are selected from the group consisting of aryl, heteroaryl, alkynyl, or alkenyl, with the proviso that the unsaturated carbons of alkenyl and alkynyl groups are directly bonded to $L_1$.

$L_1$ is selected from the group consisting of bromide, iodide, or trifluoromethanesulfonate.

$L_2$ is tri(lower alkyl)stannyl or —B(OH)$_2$.

$RPG_1$ is defined as for reaction scheme 1.

The lactam of general formula (XVII) may be treated with a palladium catalyst such as tetrakis(triphenylphosphine) palladium and $R_{34}$-$L_1$ in a solvent such as acetonitrile in the presence of a tertiary amine base such as NMM at a temperature of from 20° C. to 200° C. to afford (XVIII). Reduction of the olefinic group in (XVIII) with hydrogen and a metal catalyst such as palladium on carbon and conversion of the lactam (XI) to the acid (IV) proceeds as outlined in reaction Scheme 2. Alternately, the olefin in compounds of general formula (XVIII) may be left in place and manipulation of the lactam (XVIII) is carried out as described in reaction Scheme 2 to afford (XIX). (XIX) may be converted to (IV) as described in reaction Scheme 2 with or without reduction of the olefin in (XIX), as appropriate. The alkyne (XX) may be treated with tri(butyltin) hydride in the presence of a radical initiator such as azobis (isobutyronitrile) to afford an alkyl tin intermediate (XXI), which may be treated with $R_{34}$-$L_1$ and a catalyst such as Pd(PPh$_3$)$_4$ in a solvent such as DMF in the presence or LiCl to afford (XXII). Alternately, (XXI) may be treated with iodine in an organic solvent such as ether to afford the destannylated vinyl iodide. The iodide may be treated with $R_{34}$-$L_2$ in the presence of a palladium catalyst such as Pd(PPh$_3$)$_4$ in a solvent such as DMF or THF at a temperature of 25° C. to 140° C. to afford (XXII). The alkyne (XXIII) may be treated with $R_{35}$-$L_1$, CuCl or CuI and an alkylamine such as TEA in the presence of a catalyst such as Pd(PPh$_3$)$_4$ to afford (XXIV). (XXIV and (XXII) may be manipulated to the intermediate (IV) via the operations described in reaction scheme 2.

Reaction Scheme 5 depicts the preparation of compounds of general formula (VIII).

Reaction Scheme 5

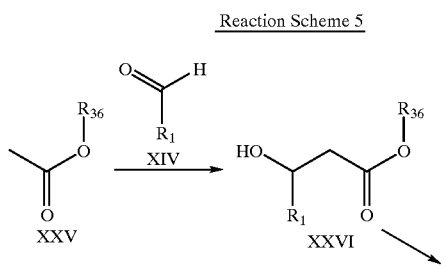
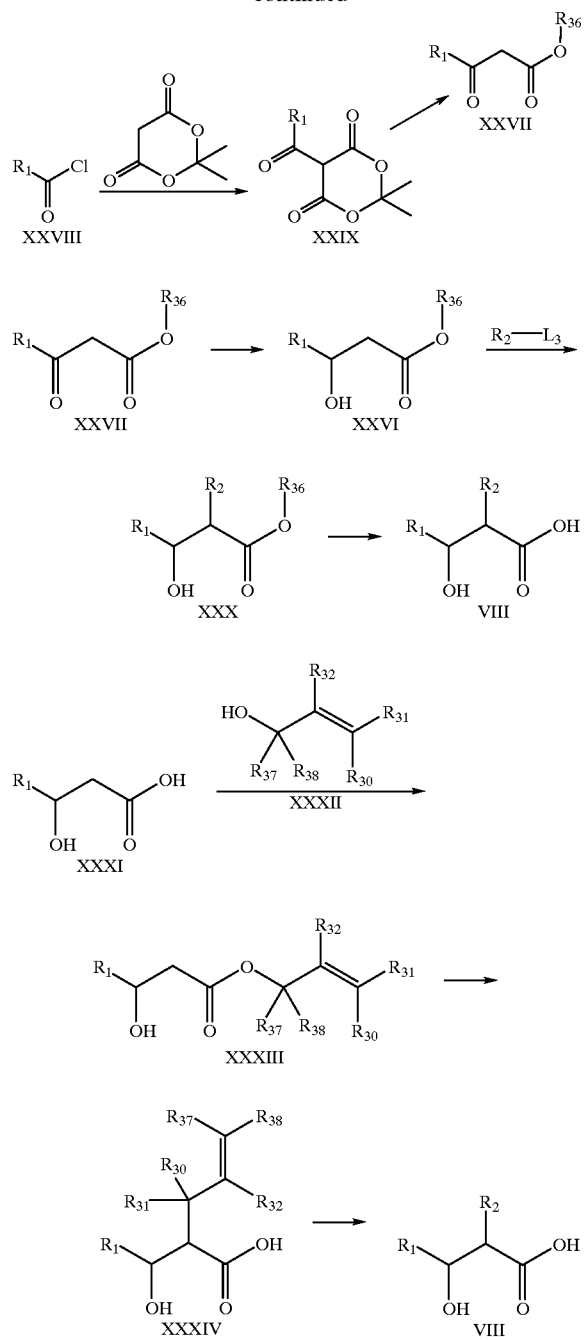

$R_1$ and $R_2$ are as defined for formula (II).
$R_{36}$ is lower alkyl.
$RPG_1$ is as defined for reaction Scheme 1.
$L_3$ is bromide, iodide, or trifluoromethanesulfonyloxy.
$R_{30}$, $R_{31}$, and $R_{32}$ are as defined for reaction scheme 4.
$R_{37}$ and $R_{38}$, may be, independently, alkyl, alkenyl, alkynyl, or hydrogen.

The ketoester of general formula (XXVII), if not commercially available, may be prepared by reaction of ester (XXV) with a strong base such as LDA followed by treatment with the aldehyde (XIV). The resulting hydroxyester (XXVI) may be used directly or converted to the ketoester (XXVII) by oxidation with, for example, pyridinium dichromate in a solvent such as dichloromethane. Alternately the acid chloride (XXVIII) may be condensed with 2,2- dimethyl-4,6-dioxo-1,3-dioxane in the presence of pyridine to afford (XXIX), which may be treated with excess $R_{36}$—OH at a temperature of from 25° C. to 150° C. to provide (XXVII). The ketoester of general formula (XXVII) may be reduced with a reducing agent such as sodium borohydride to afford the hydroxyester (XXVI). Alternately, a chiral catalyst or chiral ligand in the presence of a reducing agent such as hydrogen or a metal hydride such as borane or LAH may be employed to afford (XXVI) with chiral induction at the newly formed asymmetric center. The alcohol (XXVI) may be converted to (XXX) by treatment with a strong base such as LDA in a suitable solvent such as THF, followed by the addition of $R_2$-$L_3$ in the presence or absence of a cosolvent such as DMPU. Where $R_2$ contains an unsaturated group, (XXX) may be reduced under appropriate conditions. Removal of the ester group by hydrolysis with aqueous hydroxide or, in the case where $R_{36}$ is tert-butyl, by treatment with a strong acid such as TFA, affords (VIII). Hydroxy acid (XXXI) is obtained by hydrolysis of the ester group of (XXVI) with aqueous alkali. (XXXI) may be obtained by treatment of (XXVI) with TFA, where $R_{36}$ is tert-butyl. Coupling of the hydroxy acid (XXXI) with an allylic alcohol (XXXII) in the presence of a dehydrating agent such as EDC and a catalyst such as 4-dimethylaminopyridine provides the ester (XXXIII). Alternately, protection of the alcohol functionality of ester (XXVI) with, for example, a tert-butyldimethylsilyl group may be required before processing of (XXVI) to the acid. Hydrolysis of the ester grouping of the protected (XXVI) as before with aqueous base followed by activation of the acid functionality as its acid chloride with oxalyl chloride and addition of the alcohol (XXXII) in the presence of an organic base such as TEA provides the ester (XXXIII) with the hydroxyl group protected. Deprotection of the hydroxyl group, if so protected, and treatment of the resulting ester (XXXIII) with a strong base such as LDA in a solvent such as 1,2-dimethoxyethane at a temperature of −78° C., followed by warming of the mixture to a temperature of between 0° C. and 90° C., followed by acidification of the mixture provides the acid (XXXIV). Reduction of the olefinic group in (XXXIV) with hydrogen and a metal catalyst such as palladium on carbon provides the acid (VIII). Alternately, the olefin in compounds of general formula (XXXIV) may be left in place until a later stage and then saturated with, for example, hydrogen gas in the presence of palladium on carbon.

The preparation of compounds of general formula (VI) is shown in reaction Scheme Reaction Scheme 6

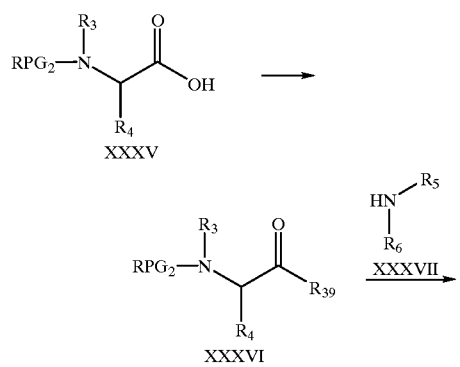

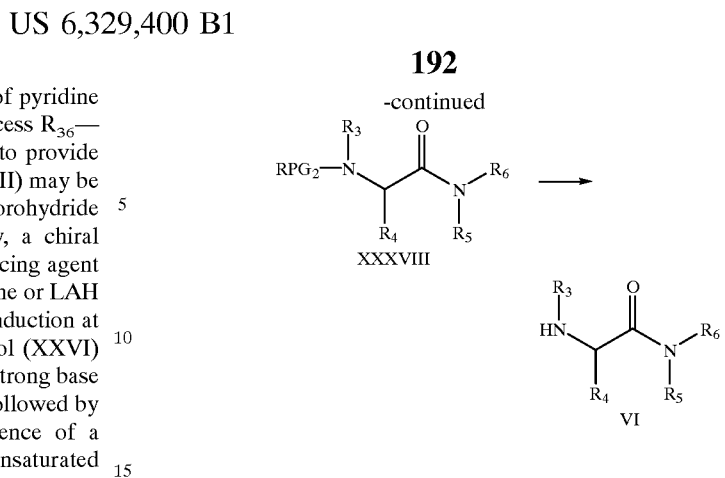

$R_3$, $R_4$, $R_5$, and $R_6$ are as defined for general formula (II). $RPG_2$ is selected from the group consisting of tert-butoxycarbonyl, allyloxycarbonyl, or benzyloxycarbonyl. $R_{39}$ is selected from the group consisting of 1-benzotriazolyloxy, or bromine.

The acid of formula (XXXV) may be converted in situ to (XXXVI), where $R_{39}$ is bromine, by treatment with bromo-tris(pyrrolidino)phosphonium hexafluorophosphate in a suitable solvent such as DMF in the presence of an organic base such as DIEA. The acid of formula (XXXV) may be converted in situ to (XXXVI), where $R_{39}$ is benzotriazolyloxy, by treatment with BOP in a suitable solvent such as DMF in the presence of an organic base such as NMM. Addition of the amine (XXXVII) in the displacement step in the presence of a suitable solvent such as DMF and an organic base such as DIEA affords the amide (XXXVIII). Alternatively, the intermediate of formula (XXXV) may be treated with carbonyldiimidazole in a solvent such as dichloromethane, followed by treatment with the amine (XXXVII) to afford (XXXVIII). Alternatively, the intermediate of formula (XXXV) may be treated with HOBt, the amine (XXXVII), an organic base such as NMM, and a carbodiimide reagent such as EDC in a suitable solvent such as DMF, at a temperature of 0° C. to 80° C. to provide (XXXVIII). The compound of formula (XXXVIII) may be converted to (VI) by deprotection, conditions being particular to the nature of $RPG_2$. For example, where $RPG_2$ is tert-butoxycarbonyl, conversion of (XXXVIII) to (VI) may be accomplished by treatment of (XXXVIII) with TFA in the presence or absence of a suitable solvent such as dichloromethane, at a temperature of 0° C. to 50° C.

Reaction scheme 7 depicts an alternate preparation of an intermediate of general formula (XXXV).

Reaction Scheme 7

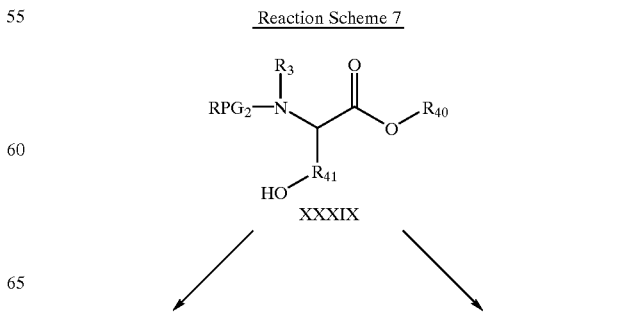

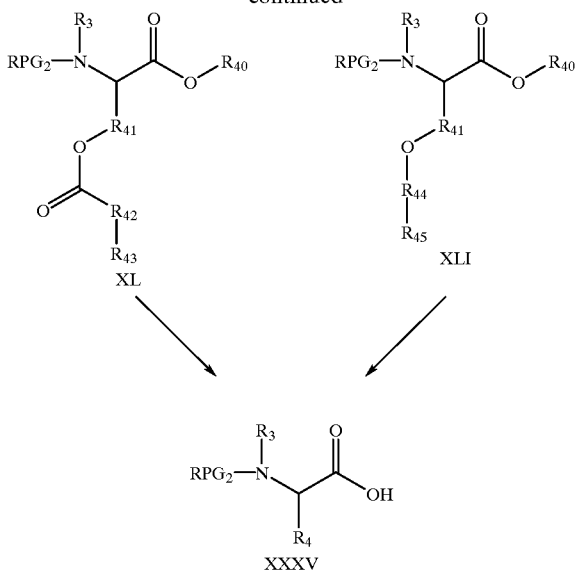

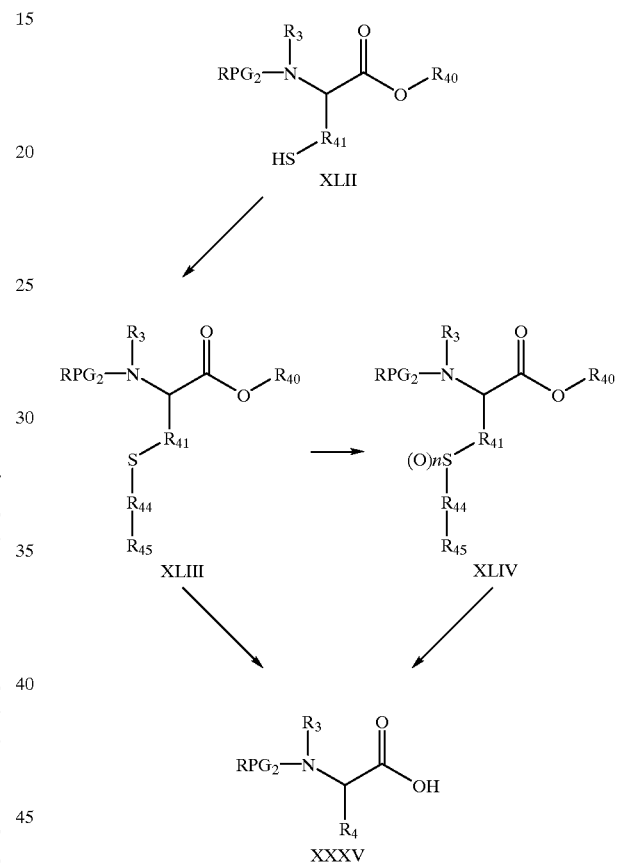

$R_3$ and $R_4$ are as defined for general formula (II).

$RPG_2$ is as defined for reaction scheme 6.

$R_{40}$ is lower alkyl or hydrogen.

$R_{41}$ is alkylene, alkenylene, alkynylene, cycloalkylene, cycloalkenylene, heterocyclylene, arylene, or heteroarylene, where alkylene, alkenylene, alkynylene, cycloalkylene, and cycloalkenylene substituents may contain one or more O, S, SO, or $SO_2$ substituents.

$R_{42}$ is alkylene, alkenylene, alkynylene, cycloalkylene, cycloalkenylene, heterocyclylene, arylene, O, NH, N-alkyl, or heteroarylene, where alkylene, alkenylene, alkynylene, cycloalkylene, and cycloalkenylene substituents may contain one or more O, S, SO, or $SO_2$ substituents.

$R_{43}$ is alkyl, alkenyl, alkynyl, cycloalkyl, cycloalkenyl, heterocyclyl, aryl, heteroaryl, or hydrogen, where alkyl, alkenyl, alkynyl, cycloalkyl, and cycloalkenyl substituents may contain one or more O, S, SO, or $SO_2$ substituents.

$R_{44}$ is alkylene or heteroarylene.

$R_{45}$ is alkyl, alkenyl, alkynyl, cycloalkyl, cycloalkenyl, heterocyclyl, aryl, heteroaryl, or hydrogen, where alkyl, alkenyl, alkynyl, cycloalkyl, and cycloalkenyl substituents may contain one or more O, S, SO, or $SO_2$ substituents.

The hydroxy compound (XXXIX) may be treated with the reagent $R_{43}$—$R_{42}$—COCl in a solvent such as dichloromethane in the presence of tertiary base such as TEA to afford (XL). Alternately, (XXXIX) may be treated with $R_{43}$—$R_{42}$—COOH (where $R_{42}$ is not O, NH, or N-alkyl) and a dehydrating agent such as EDC and a catalyst such as DMAP in a solvent such as DMF or dichloromethane to afford (XL). The compound (XL) where $R_{42}$ is NH may be prepared by treating (XXXIX) with $R_{43}$—NCO in a solvent such as dichloromethane. The ether (XLI) may be prepared by treating (XXXIX) with $R_{45}R_{44}$ Br or $R_{45}R_{44}$ I in the presence of a base such as potassium carbonate or sodium hydride in a solvent such as DMF. Removal of the alkyl group $R_{40}$ by saponification with aqueous base (or, if appropriate and where $R_{40}$ is tert-butyl, by treatment with trifluoroacetic acid) provides the acid (XXXV).

Reaction scheme 8 depicts an alternate preparation of an intermediate of general formula (XXXV).

$R_3$ and $R_4$ are as defined for general formula (II).
$RPG_2$ is as defined for reaction scheme 6
$R_{40}$, $R_{41}$, $R_{44}$ and $R_{45}$ are as defined for reaction scheme 7.
n is 1 to 2.

The thioether (XLIII) may be prepared by treating (XLII) with $R_{45}R_{44}$Br or $R_{45}R_{44}$I and a base such as potassium carbonate or sodium hydride in a solvent such as DMF. The sulfur atom may be oxidized with a reagent such as m-chloroperoxybenzoic acid. Use of one molar equivalent of oxidant may be employed to provide (XLIV) where n is 1. Use of two molar equivalents of oxidant may be employed to provide (XLIV) where n is 2. Removal of the alkyl group $R_{40}$ in either (XLIII) or (XLIV) by saponification with aqueous base (or, if appropriate and where $R_{40}$ is tert-butyl, by treatment with trifluoroacetic acid) provides the acid (XXXV).

Reaction scheme 9 depicts an alternate preparation of an intermediate of general formula (XXXV).

Reaction Scheme 9

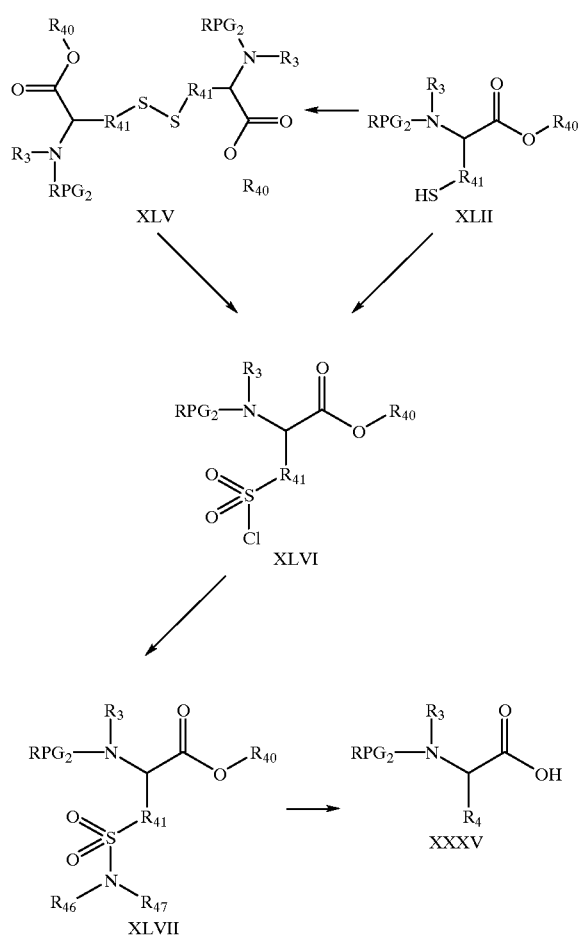

$R_3$ and $R_4$ are as defined for general formula (II).

$RPG_2$ is as defined for reaction scheme 6.

$R_{40}$ and $R_{41}$ are as defined for reaction scheme 7.

$R_{46}$ and $R_{47}$ are, independently, alkyl, alkenyl, alkynyl, cycloalkyl, cycloalkenyl, heterocyclyl, aryl, heteroaryl, carboxamidine, or hydrogen, where alkyl, alkenyl, alkynyl, cycloalkyl, and cycloalkenyl substituents may contain one or more O, S, SO, or $SO_2$ substituents.

$R_{46}$ and $R_{47}$ may be taken together to constitute a three- to ten-membered ring.

The thiol (XLII) may be oxidized to the disulfide (XLV) by treatment with a mild base such as TEA and oxygen or air. Either the thiol (XLII) or the di sulfide (XLV) may be converted to the sulfonyl chloride (XLVI) by treatment with chlorine gas in tetrachioromethane. Treatment of the sulfonyl chloride (XLVI) with an amine $R_{46}R_{47}NH$ in the presence of a tertiary amine base such as TEA or NMM affords (XLVII). Removal of the alkyl group $R_{40}$ in (XLVII) by saponification with aqueous base (or, if appropriate and where $R_{40}$ is tert-butyl, by treatment with trifluoroacetic acid) provides the acid (XXXV).

Reaction scheme 10 depicts an alternate preparation of an intermediate of general formula (XXXV).

Reaction Scheme 10

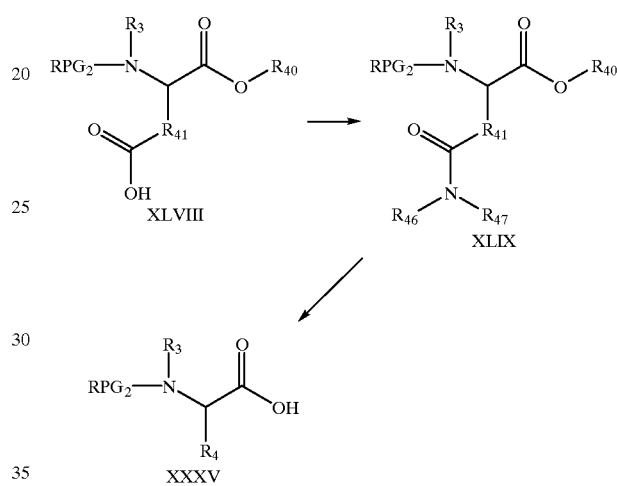

$R_3$ and $R_4$ are as defined for general formula (II).

$RPG_2$ is as defined for reaction scheme 6.

$R_{40}$ and $R_{41}$, are as defined for reaction scheme 7.

$R_{46}$ and $R_{47}$ are as defined for reaction scheme 9.

$R_{46}$ and $R_{47}$ may be taken together to constitute a three-to ten-membered ring.

The acid (XLVIII) may be converted to the amide (XLIX) by treatment of (XLVIII) and the amine $R_{46}R_{47}NH$ with a dehydrating agent such as EDC or BOP in the presence of HOBt. Removal of the alkyl group $R_{40}$ in (XLIX) by saponification with aqueous base (or, if appropriate and where $R_{40}$ is tert-butyl, by treatment with trifluoroacetic acid) provides the acid (XXXV).

Reaction Scheme 11 depicts an alternate preparation of an intermediate of general formula (XXXV).

Reaction Scheme 11

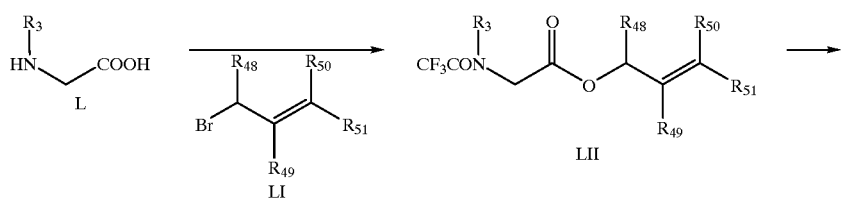

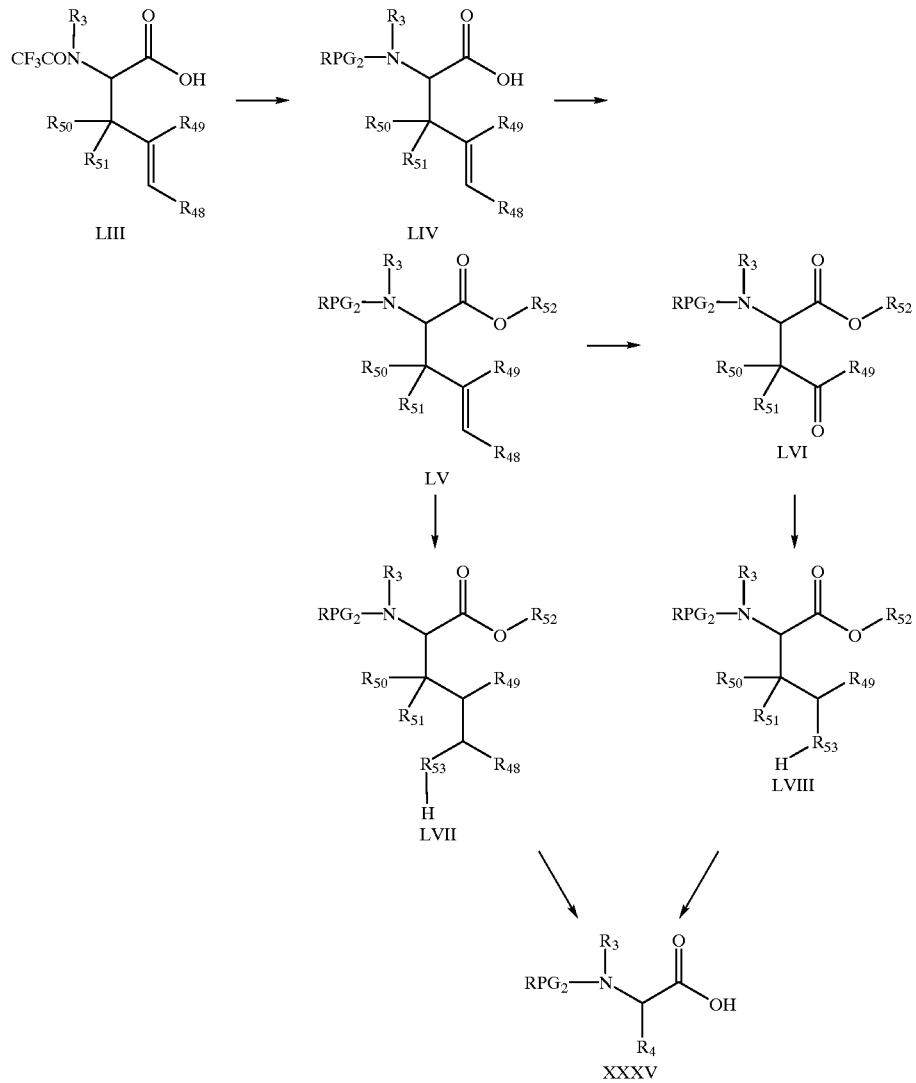

-continued where $R_3$ and $R_4$ are as defined for general formula (II).
$RPG_2$ is defined as for reaction scheme 6.
$R_{48}$ is hydrogen, lower alkyl, or aryl.
$R_{49}$, $R_{50}$, and $R_{51}$ are, independently, alkyl, alkenyl, alkynyl, cycloalkyl, cycloalkenyl, heterocyclyl, aryl, or heteroaryl.
$R_{50}$ and $R_{51}$ may be taken together to constitute a five- to ten-membered ring.
$R_{49}$ and $R_{51}$ may be taken together to constitute a five- to ten-membered ring.
$R_{48}$ and $R_{50}$ may be taken together to constitute a five- to ten-membered ring.
$R_{52}$ is lower alkyl or benzyl.
$R_{53}$ is O or NH.
$L_4$ is Br or I.

The acid (L) is treated with trifluoroacetic anhydride and TFA to afford the trifluoroacetamide, which is then treated with the bromide (LI) and a base such as potassium carbonate or DBU in a solvent such as DMF to provide the ester (LII). (LII) is treated with LDA and aluminum trilsopropoxide in the presence of quinidine or quinine in a solvent such as THF at a temperature of from −78° C. to 25° C. to afford (LIII) with a high degree of asymmetric induction. (LIII) is subjected to hydrolysis with aqueous base and the resulting amine is protected with $RPG_2$—Cl (where $RPG_2$ is benzyloxycarbonyl) or $(RPG_2)_2O$ (where $RPG_2$ is tert-butoxycarbonyl) and aqueous base. (LIV) is then esterified with $R_{52}$—$L_4$ (where $R_{52}$ is methyl or ethyl) and potassium carbonate in DMF or by treatment with dimethylformamide di-tert-butyl acetal (where $R_{52}$ is tert-butyl). (LV) may be treated with ozone in dichloromethane or dichloromethane/MeOH, followed by reduction with, for example, dimethyl sulfide to afford the carbonyl compound (LVI). (LVI) may be reduced with sodium borohydride to afford the alcohol (LVIII) (where $R_{53}$ is O), which may be treated in with methanesulfonyl chloride in pyridine to afford the mesylate. The methanesulfonate may be then treated with sodium azide in a solvent such as DMF at a temperature of from 25° C. to 120° C. to afford the azide, which may be reduced with, for example, palladium on barium sulfate and hydrogen gas to provide (LVIII) where $R_{53}$ is NH. (LV) may be hydroborated with a borane reagent such as diborane followed by treatment with aqueous alkaline hydrogen peroxide to afford (LVII) where $R_{53}$ is O. (LVII) may be manipulated at $R_{53}$ in the manner described for (LVIII), and $R_{53}$ may be acylated alkylated, or sulfonylated as desired. The $R_{52}$ group may be removed by treatment with sodium hydroxide in aqueous THF (where $R_{52}$ is ethyl or methyl), or by treatment with TFA or anhydrous HCl (where $R_{52}$ is tert-butyl). Selection of $R_{52}$ as tert-butyl and $RPG_2$ as benzyloxycarbonyl is optimal for the preparation of (XXXV) according to reaction scheme 11.

Reaction scheme 12 depicts an alternate preparation of an intermediate of general formula (XXXV).

Reaction Scheme 12

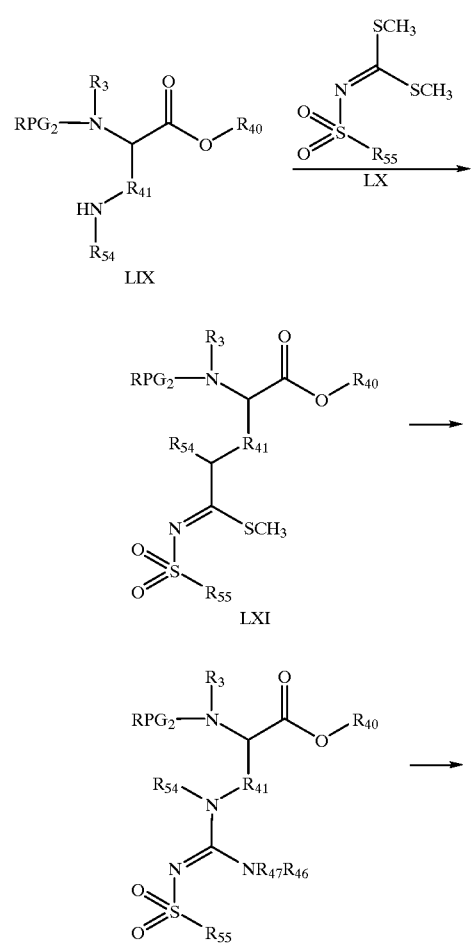

$R_3$ and $R_4$ are as defined for general formula (II).
$RPG_2$ is as defined for reaction scheme 6.
$R_{40}$ and $R_{41}$ are as defined for reaction scheme 7.
$R_{46}$ and $R_{47}$ are as defined for reaction scheme 9.
$R_{46}$ and $R_{47}$ may be taken together to constitute a three- to ten-membered ring.
$R_{54}$ and $R_{55}$ may be, independently, alkyl, alkenyl, alkynyl, cycloalkyl, cycloalkenyl, heterocyclyl, aryl, heteroaryl, or hydrogen, where alkyl, alkenyl, alkynyl, cycloalkyl, and cycloalkenyl substituents may contain one or more O, S, SO, or $SO_2$ substituents.

The amine compound (LIX) is treated with (LX) in the presence of a tertiary base such as TEA or NMM to afford (LXI). Treatment of (LXI) with silver nitrate and an amine $HNR_{46}R_{47}$ provides (LXII). Removal of the alkyl group $R_{40}$ by saponification with aqueous base (or, if appropriate and where $R_{40}$ is tert-butyl, by treatment with trifluoroacetic acid) provides (XXXV).

Reaction scheme 13 describes an alternate preparation of an intermediate of formula (XXXV).

Reaction Scheme 13

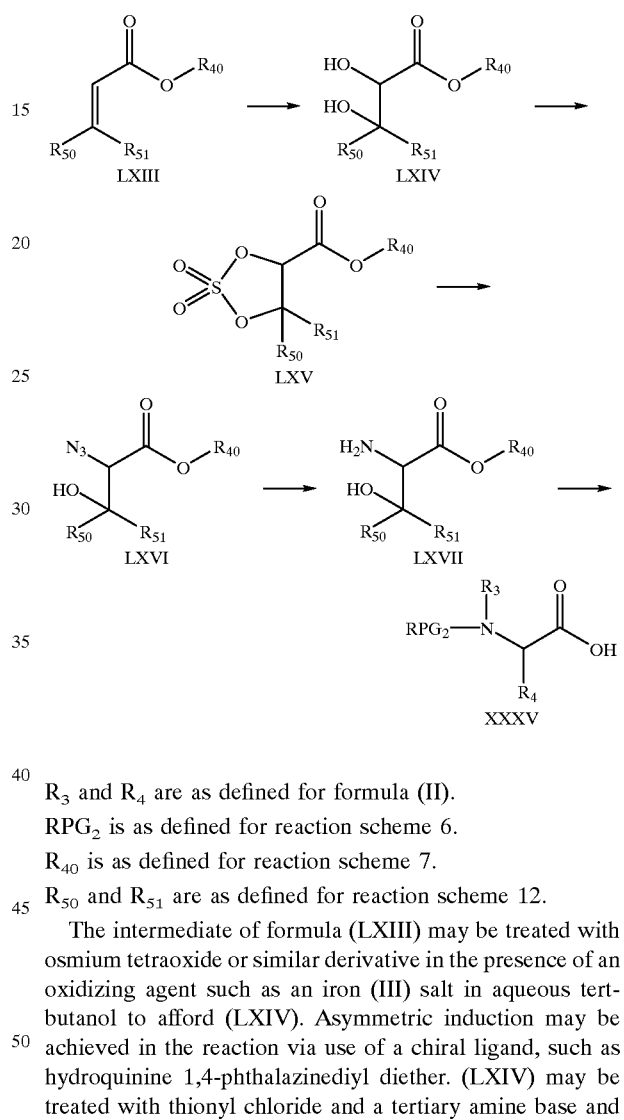

$R_3$ and $R_4$ are as defined for formula (II).
$RPG_2$ is as defined for reaction scheme 6.
$R_{40}$ is as defined for reaction scheme 7.
$R_{50}$ and $R_{51}$ are as defined for reaction scheme 12.

The intermediate of formula (LXIII) may be treated with osmium tetraoxide or similar derivative in the presence of an oxidizing agent such as an iron (III) salt in aqueous tert-butanol to afford (LXIV). Asymmetric induction may be achieved in the reaction via use of a chiral ligand, such as hydroquinine 1,4-phthalazinediyl diether. (LXIV) may be treated with thionyl chloride and a tertiary amine base and the resulting sulfite may be oxidized with $RuO_4$ or $RuCl_3$ and $NaIO_4$ in aqueous acetonitrile/$CCl_4$ to afford the sulfate (LXV). Treatment of the sulfate with sodium azide in aqueous acetone affords (LXVI). Reduction of the azide with palladium on carbon and hydrogen gives the amine (LXVII). The amine may be alkylated with $R_3$ if desired, protected with $RPG_2$ (as described in previous schemes), and the $R_{40}$ ester group removed to provide (XXXV). Selection of $R_{40}$ as benzyl and $RPG_2$ as tert-butoxycarbonyl are desirable for the sequence of reactions in reaction scheme 13.

Reaction scheme 14 describes an alternate preparation of an intermediate of formula (XXXV).

Reaction Scheme 14

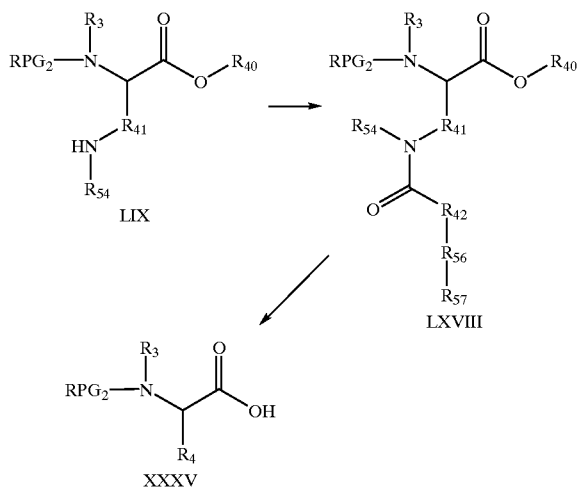

$R_3$ and $R_4$ are as defined for general formula (II).
$RPG_2$ is as defined for reaction scheme 6.
$R_{40}$, $R_{41}$, and $R_{42}$ are as defined for reaction scheme 7.
$R_{54}$ is as defined for reaction scheme 12.
$R_{56}$ is alkylene, alkenylene, alkynylene, cycloalkylene, cycloalkenylene, heterocyclylene, arylene, O, NH, N-alkyl, or heteroarylene, where alkylene, alkenylene, alkynylene, cycloalkylene, and cycloalkenylene substituents may contain one or more O, S, SO, or $SO_2$ substituents.
$R_{57}$ is alkyl, alkenyl, alkynyl, cycloalkyl, cycloalkenyl, heterocyclyl, aryl, heteroaryl, or hydrogen, where alkyl, alkenyl, alkynyl, cycloalkyl, and cycloalkenyl substituents may contain one or more O, S, SO, or $SO_2$ substituents.

The amine compound (LIX) may be treated with the reagent $R_{57}$—$R_{56}$—$R_{42}$—COCl in a solvent such as dichloromethane in the presence of tertiary base such as TEA to afford (LXVIII). Alternately, (LIX) may be treated with $R_{57}$—$R_{56}$—$R_{42}$—COOH (where $R_{42}$ is not O, NH, or N-alkyl) and a dehydrating agent such as EDC in a solvent such as DMF or dichloromethane to afford (LXVIII). The compound (LXVIII) where $R_{42}$ is NH may be prepared by treating (LIX) with $R_{57}$—$R_{56}$—NCO in a solvent such as dichloromethane. Removal of the alkyl group $R_{40}$ by saponification with aqueous base (or, if appropriate and where $R_{40}$ is tert-butyl, by treatment with trifluoroacetic acid) provides the acid (XXXV).

PHARMACEUTICAL FORMULATION AND DOSES

The compounds of the present invention can be administered in such oral (including buccal and sublingual) dosage forms as tablets, capsules (each including timed release and sustained release formulations), pills, powders, granules, elixirs, tinctures, suspensions, syrups and emulsions. Likewise, they may also be administered in nasal, ophthalmic, otic, rectal, topical, intravenous (both bolus and infusion), intraperitoneal, intraarticular, subcutaneous or intramuscular inhalation or insufflation form, all using forms well known to those of ordinary skill in the pharmaceutical arts.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.1 to 2000 mg/kg of body weight per day, and particularly 1 to 100 mg/kg of body weight per day. Oral dosage units will generally be administered in the range of from 1 to about 250 mg and more preferably from about 25 to 250 mg. The daily dosage for a 70 kg mammal will generally be in the range of about 10 mg to 5 grams of a compound of formula (I) or(II).

While the dosage to be administered is based on the usual conditions such as the physical condition of the patient, age, body weight, past medical history, route of administrations, severity of the conditions and the like, it is generally preferred for oral administration to administer to a human. In some cases, a lower dose is sufficient and, in some cases, a higher dose or more doses may be necessary. Topical application similarly may be once or more than once per day depending upon the usual medical considerations. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (II) in combination with a pharmaceutically acceptable carrier.

Parenteral administration can be effected by utilizing liquid dosage unit forms such as sterile solutions and suspensions intended for subcutaneous, intramuscular, intrathecal, intraarterial or intravenous injection. These are prepared by suspending or dissolving a measured amount of the compound in a non-toxic liquid vehicle suitable for injection such as aqueous oleaginous medium and sterilizing the suspension or solution.

Alternatively, a measured amount of the compound is placed in a vial and the vial and its contents are sterilized and sealed. An accompanying vial or vehicle can be provided for mixing prior to administration. Non-toxic salts and salt solutions can be added to render the injection isotonic. Stabilizers, preservations and emulsifiers can also be added.

Rectal administration can be effected utilizing suppositories in which the compound is admixed with low-melting water-soluble or insoluble solids such as polyethylene glycol, cocoa butter, higher ester as for example flavored aqueous solution, while elixirs are prepared through myristyl palmitate or mixtures thereof.

Topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The preferred pharmaceutical compositions are those in a form suitable for oral administration, such as tablets and liquids and the like and topical formulations.

EXAMPLES

The following examples are illustrative embodiments of the invention, not limiting the scope of the invention in any way. Reagents are commercially available or are prepared according to procedures in the literature.

Example 1

(2R,3S)-3-(Formyl-hydroxyamino)-2-(3-phenyl-1-propyl)butanoic Acid [(1S)-2,2-Dimethyl-1-(3-pyridylcarbamoyl)-1-propyl]amide

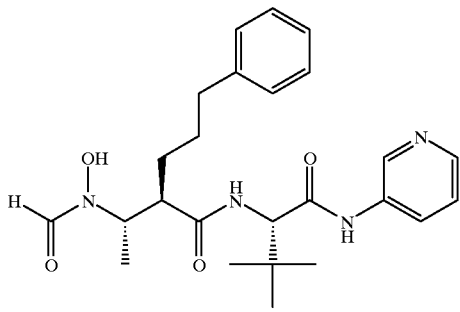

Example 1a

Methyl (2R,3R)-2-[(2E)-3-Phenyl-2-propen-1-yl]-3-hydroxybutanoate

To a solution of diisopropylamine (47.1 g, 466.1 mmol) in THF (500 mL) cooled to −50° C. is added n-butyllithium (466.1 mmol, 2.5M in hexanes) and the resulting solution is stirred at −50° C. for 0.5 h. The reaction mixture is cooled to −78° C. followed by slow addition of methyl (3R)-3-hydroxybutanoate (25 g, 211.9 mmol). After 0.5 h a solution of cinnamyl bromide (45.9 g, 233.0 mmol) in HMPA (10 mL) is added and the reaction mixture is allowed to warm to 0° C. and stirred for 16 h. The reaction mixture is quenched by addition 30 mL of saturated aqueous ammonium chloride solution, is poured into 400 mL of 1 N hydrochloric acid, and is extracted with two 500-mL portions of EtOAc. The combined organic layers are dried over magnesium sulfate, concentrated in vacuo, and purified by silica gel chromatography (elution with 25% EtOAc-hexanes) to afford methyl (2R,3R)-2-[(2E)-3-phenyl-2-propen-1-yl]-3-hydroxybutanoate as a yellow oil (42 g, 85% yield).

$^1$H NMR (400 MHz, CDCl$_3$) δ 7.32–7.18 (m, 5H), 6.44 (d, 1H), 6.13 (m, 1H), 3.98 (m, 1H), 3.69 (s, 3H), 2.56 (m, 4H), 1.25 (t, 3H) ppm. ESI-MS m/z 257 (M+Na)$^+$.

Example 1b

Methyl (2R,3R)-2-(3-Phenyl-1-propyl)-3-hydroxybutanoate

A solution of methyl (2R,3R)-2-[(2E)-3-phenyl-2-propen-1-yl]-3-hydroxybutanoate (42.0 g, 179.5 mmol) in 400 mL of methanol is treated with 400 mg of 10% palladium on carbon. The resulting suspension is repeatedly evacuated and purged with a hydrogen balloon, then stirred under 1 atmosphere pressure of hydrogen gas for 16 h. The catalyst is filtered and the filtrate is concentrated in vacuo to provide methyl (2R,3R)-2-(3-phenyl-1-propyl)-3-hydroxybutanoate as an oil (42.2 g, 100% yield).

$^1$H NMR (400 MHz, CDCl$_3$) δ 7.25 (m, 2H), 7.17 (m, 3H), 3.88 (m, 1H), 3.69 (s, 3H), 2.61 (m, 2H), 2.42 (m, 2H), 1.72 (m, 1H), 1.62 (m, 3H), 1.19 (d, 3H) ppm. ESI-MS m/z 259 (M+Na)$^+$.

Example 1c (2R,3R)-2-(3-Phenyl-1-propyl)-3-hydroxybutanoic Acid

To a solution of methyl (2R,3R)-2-(3-phenyl-1-propyl)-3-hydroxybutanoate (42.2 g, 179.5 mmol) in THF-methanol (3:1, 535 mL) is added 2 N aqueous sodium hydroxide solution (135 mL, 269.3 mmol). The solution is stirred at 23° C. for 20 h, then concentrated and extracted with hexanes (100 mL). The aqueous layer is acidified to pH 3 with saturated aqueous sodium bisulfate and is extracted with two 500-mL portions of EtOAc. The combined organic layers are dried over magnesium sulfate and concentrated under reduced pressure to provide (2R,3R)-2-(3-phenyl-1-propyl)-3-hydroxybutanoic acid as an oil (33.0 g, 83% yield).

$^1$H NMR (400 MHz, CDCl$_3$) δ 7.28 (m, 2H), 7.16 (m, 3H), 3.93(m, 1H), 2.63 (m, 2H), 2.43 (m, 1H), 1.69 (m, 4H), 1.26 (d, 3H) ppm. ESI-MS m/z 221 (M−1)$^-$.

Example 1d (2R,3R)-2-(3-Phenyl-1-propyl)-3-hydroxybutanoic Acid 2-Tetrahydropyranyloxyamide To a solution of (2R,3R)-2-(3-phenyl-1-propyl)-3-hydroxybutanoic acid (33.0 g, 148.7 mmol) in dichloromethane (300 mL) is added 2-tetrahydropyranyloxyamine (18.3 g, 156.1 mmol) and EDC (31.2 g, 163.5 mmol). The resulting solution is stirred at 23° C. for 16 h, then diluted with dichloromethane (500 mL) and washed sequentially with 1 N hydrochloric acid, saturated aqueous sodium bicarbonate solution, and saturated aqueous sodium chloride solution. The reaction mixture is dried over magnesium sulfate and concentrated under reduced pressure to provide (2R,3R)-2-(3-phenyl-1-propyl)-3-hydroxybutanoic acid 2-tetrahydropyranyloxyamide as a foam (47.8 g, 100% yield).

$^1$H NMR (400 MHz, CDCl$_3$) δ 8.66 (bs, 1H), 7.25 (m, 2H), 7.17 (m, 3H), 4.94 (m, 1H), 3.89 (m, 2H), 3.61 (m, 1H), 2.62 (t, 2H), 1.93 (m, 1H), 1.78 (m, 4H), 1.66 (m, 6H), 1.23 (d, 3H) ppm. ESI-MS m/z 320 (M−1)$^-$.

Example 1e (3R,4S)-1-(2-Tetrahydropyranyloxy)-3-(3-phenyl-1-propyl)-4-methylazetidin-2-one To a solution of (2R,3R)-2-(3-phenyl-1-propyl)-3-hydroxybutanoic acid 2-tetrahydropyranyloxyamide (47.8 g, 148.7 mmol) in 150 mL of dichloromethane at 0° C. is added pyridine (64 mL) and methanesulfonyl chloride (20.4 g, 178.4 mmol). The resulting solution is allowed to warm to 23° C. and is stirred at 23° C. for 14 h, concentrated in vacuo, and diluted with dichloromethane (500 mL). The organic layer is washed with 1 N hydrochloric acid, saturated aqueous sodium chloride solution, dried over anhydrous magnesium sulfate, and concentrated to provide the methanesulfonate intermediate.

A suspension of potassium carbonate (61.5 g) in acetone (500 mL) is heated to reflux for 1 h. A solution of the above methanesulfonate in acetone (1 L) is added and the resulting suspension is heated at reflux for 28 h. The mixture is allowed to cool to 25° C. and is filtered, concentrated under reduced pressure, and purified by silica gel chromatography (elution with 3:1 hexanes-EtOAc) to provide (3R,4S)-1-(2-tetrahydropyranyloxy)-3-(3-phenyl-1-propyl)-4-methylazetidin-2-one as an oil (34.0 g, 75% yield).

$^1$H NMR (400 MHz, CDCl$_3$) δ 7.25 (m, 2H), 7.17 (m, 3H), 5.13 and 4.99 (two m, 1H), 4.15–3.98 (m, 2H), 2.64 (m, 1H), 2.93 (m, 1H), 2.67 (m, 2H), 1.89–1.51 (m, 10H), 1.28 and 1.26 (two d, 3H) ppm. ESI-MS m/z 326 (M+Na)$^+$.

Example 1f (2R,3S)-2-(3-Phenyl-1-propyl)-3-(2-tetrahydropyranyloxyamino)butanoic Acid To a solution of (3R,4S)-1-(2-tetrahydropyranyloxy)-3-(3-phenyl-1-propyl)-4-methylazetidin-2-one (20.5 g, 67.6 mmol) in dioxane (220 mL) is added 1 N aqueous sodium hydroxide (102 mL). The solution is stirred at 23° C. for 20 h, then extracted with hexanes (200 mL). The aqueous layer is acidified to pH 3 with saturated aqueous sodium bisulfate solution, and is; extracted with two 300-mL portions of EtOAc. The combined organics are washed with saturated aqueous sodium chloride, dried over anhydrous magnesium sulfate, and concentrated under reduced pressure to provide (2R,3S)-2-(3-phenyl-1-propyl)-3-(2-tetrahydropyranlyloxyamino)butanoic acid as an oil (21.5 g, 99% yield).

$^1$H NMR (400 MHz, CDCl$_3$) δ 7.28 (m, 2H), 7.18 (m, 3H), 4.84 and 4.70 (two m, 1H), 3.96 and 3.89 (two m, 1H), 3.56 (m, 1H), 3.34 and 3.24 (two m, 1H), 2.97 and 2.81 (two m, 1H), 2.65 (m, 2H), 1.96–1.45 (m, 10H), 1.31 (m, 1H), 1.06 and 0.99 (two d, 3H) ppm. ESI-MS m/z 344 (M+H)$^+$.

Example 1g (2R,3S)-2-(3-Phenyl-1-propyl)-3-(formyl-2-tetrahydropyranyloxyamino)butanoic Acid To a solution of (2R,3S)-2-(3-phenyl-1-propyl)-3-(2-tetrahydropyranyloxyamino)butanoic acid (21.4 g, 66.7 mmol) in pyridine (100 mL) at 0° C. is added formic acetic anhydride (30 mL). The resulting solution is allowed to warm to 25° C., stirred for 6 h, and then concentrated to dryness under reduced pressure. The resulting gum is dissolved in EtOAc (300 mL) and washed sequentially with 1 N hydrochloric acid (200 mL) and saturated aqueous sodium chloride solution. The organic layer is dried over anhydrous magnesium sulfate and concentrated under reduced pressure providing (2R,3S)-2-(3-phenyl-1-propyl)-3-(formyl-2-tetrahydropyranyloxyamino)butanoic acid as an oil (18.9 g, 81% yield). ESI-MS m/z 372 (M+Na)$^+$348 (M−1)$^{31}$.

Example 1h (2S)-2-tert-Butoxycarbonylamino-3,3-dimethylbutanoic Acid 3-Pyridylamide To a solution of (2S)-2-tert-butoxycarbonylamino-3,3-dimethylbutanoic acid (3 g, 12.99 mmol) in DMF (25 mL) is added EDC (2.73 g, 14.29 mmol) and HOBT (1.93 g, 14.29 mmol). The resulting solution is stirred at 25° C. for 0.5 h and 3-aminopyridine (1.83 g, 19.48 mmol) is; added and the reaction is heated to 50° C. for 18 h. The mixture is concentrated, diluted with EtOAc (50 mL), and washed with saturated aqueous sodium bicarbonate. The organic layer is dried over anhydrous magnesium sulfate and concentrated in vacuo to provide (2S)-2-tert-butoxycarbonylamino-3,3-dimethylbutanoic acid 3-pyridylamide as a foam (1.6 g, 40% yield).

$^1$H NMR (400 MHz, CDCl$_3$) δ 8.56 (s, 1H), 8.24 (bs, 1H), 7.99 (bs, 1H), 7.18 (bs, 1H), 5.16 (m, 1H), 4.06 (m, 1H), 1.43 (s, 9H), 1.02 (s, 9H) ppm. ESI-MS m/z 308 (M+H)$^+$.

Example 1i (2S)-2-Amino-3,3-dimethylbutanoic Acid 3-pyridylamide Dihydrochloride To a solution of (2S)-2-tert-butoxycarbonylamino-3,3-dimethylbutanoic acid 3-pyridylamide (1.6 g, 5.21 mmol) in dichloromethane (10 mL) cooled at 0° C. is added 4 M HCl in dioxane (10 mL). The resulting solution is allowed to warm to 25° C. and is stirred for 3 h. The reaction mixture is concentrated and the solid is filtered to provide (2S)-2-amino-3,3-dimethylbutanoic acid 3-pyridylamide dihydrochloride (1.40 g, 94% yield) as a white solid.

$^1$H NMR (400 MHz, CD$_3$OD) δ 9.44 (s, 1H), 8.69 (d, 1H), 8.64 (d, 1H), 8.09 (dd, 1), 3.96 (s, 1H), 1.17 (s, 9H) ppm. ESI-MS m/z 208 (M+H)$^+$.

Example 1j (2R,3S)-3-(Formyl-2-tetrahydropyranyloxyamino)-2-(3-phenyl-1-propyl)butanoic Acid [(1S)-2,2-Dimethyl-1-(3-pyridylcarbamoyl)-1-propyl]amide To a solution of (2R,3S)-2-(3-phenyl-1-propyl)-3-(formyl-2-tetrahydropyrariyloxyamino)butanoic acid (120 mg, 0.344 mmol) in DMF (1 mL) is added BOP reagent (167 mg, 0.378 mmol), HOBt (51 mg, 0.378 mmol), and NMM (174 mg, 1.72 mmol). After 30 min, (2S)-2-amino-3,3-dimethylbutanoic acid 3-pyridylamide dihydrochloride (118 mg, 0.410) is added and the resulting solution is stirred at 25° C. for 18 h. The reaction mixture is concentrated, diluted with EtOAc (20 mL) and washed sequentially with 1 M aqueous sodium carbonate and saturated aqueous sodium chloride. The organic layer is dried over magnesium sulfate, concentrated in vacuo, and purified by silica gel chromatography (elution with 2:1 EtOAc-hexane) to provide (2R,3S)-3-(formyl-2-tetrahydropyranyloxyamino)-2-(3-phenyl-1-propyl)butanoic acid [(1S)-2,2-dimethyl-1-(3-pyridylcarbamoyl)-1-propyl]amide as a solid (115 mg, 62% yield). ESI-MS m/z 529 (M+H)$^+$.

Example 1

(2R,3S)-3-(Formyl-hydroxyamino)-2-(3-phenyl-1-propyl)butanoic Acid [(1S)-2,2-Dimethyl-1-(3-pyridylcarbamoyl)-1-propyl]amide A solution of (2R,3S)-3-(formyl-2-tetrahydropyranyloxyamino)-2-(3-phenyl-1-propyl)butanoiic acid [(1S)-2,2-dimethyl-1-(3-pyridylcarbamoyl)-1-propyl]amide (115 mg, 0.214 mmol) in acetic acid-water (4:1, 1 mL) is heated to 50° C. for 18 h. The reaction mixture is concentrated, then dissolved in toluene and concentrated in vacuo. The procedure is repeated once again to afford the crude product which is triturated from hot dichloromethane-ether to provide (2R,3S)-3-(formyl-hydroxyamino)-2-(3-phenyl-1-propyl)butanoic acid [(1S)-2,2-dimethyl-1-(3-pyridylcarbamoyl)-1-propyl]amide as an off-white solid (70 mg, 72% yield).

$^1$H NMR (400 MHz, CD$_3$OD) δ 8.76 (s, 1H), 8.25 and 7.99 (two s, 1H), 8.22 (d, 1H), 8,02 (t, 1H), 7.36 (dd, 1H), 7.00 (m, 5H), 4.48 and 3.82 (two dq, 1H), 4.44 (s, 1H), 2.94 and 2.82 (two m, 1H), 2.58 (m, 1H), 2.42 (m, 1H), 1.50 (m, 4H), 1.24 and 1.18 (two d, 3H), 1.02 (s, 9H) ppm. ESI-MS m/z 4:55 (M+H)$^+$. Anal. Calcd. for $C_{25}H_{34}N_4O_4 \cdot 0.5$ CH$_3$CO$_2$H: C, 64.44; H, 7.49; N, 11.56. Found: C, 64.52; H, 7.49; N, 11.48.

Example 2

(2R,3S)-3-(Formyl-hydroxyamino)-2-(4-phenylcyclohexylmethyl)butanoic Acid [(1S)-2,2-Dimethyl-1-(1,3-thiazol-2-ylcarbamoyl)-1-propyl] amide

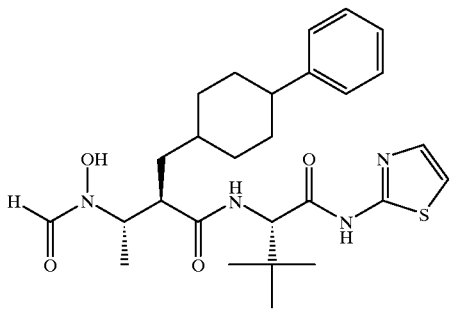

Example 2a

4-Phenyl-1-methylenecyclohexane

μ-Chloro-μ-methylene[bis(cyclopentadienyl)titanium] dimethylaluminum (172 mL, 0.086 mol, 0.5 M in toluene) is added dropwise to a solution of 4-phenylcyclohexanone (15.0 g, 0.086 mol) in THF (100 mL) at 0° C. The mixture is allowed to come to 25° C. After 15 min., ether (100 mL) is added followed by dropwise addition of 0.1 M sodium hydroxide (120 mL). The mixture is stirred an 25° C. for 18 h, filtered, and the filtrate is dried over sodium sulfate and concentrated in vacuo . The residue is purified by column chromatography on silica gel using dichloromethane-hexanes (1:1) as eluent. The resulting yellow oil is rechromatographed using hexanes as eluent to give 8.9 g (61%) of 4-phenyl-1-methylenecyclohexane as an oil.

$^1$H NMR (300 MHz, CDCl$_3$) δ 7.36–7.23 (m, 5H), 4.72 (s, 2H), 2.71 (m, 1H), 2.47 (m, 2H), 2.22 (m, 2H), 2.03 (m, 2H), 1.54 (m, 2H) ppm. ESI-MS m/z 173 (M+H)$^+$.

Example 2b

4-Phenylcyclohexylmethanol

A solution of 4-phenyl-1-methylenecyclohexane (8.9 g, 0.051 mol) in THF (10 mL) is added dropwise to a solution of borane (15 mL, 0.015 mol, 1 M in THF) at 0° C. under argon. The mixture is stirred at 25° C. for 2.5 h. A solution of aqueous sodium hydroxide (5 mL, 0.015 mol, 3 M) is added dropwise, the mixture is chilled to 0° C. and aqueous hydrogen peroxide (6 mL, 0.06 mol, 30%) is added dropwise. After stirring at 25° C. for 1 h the mixture is poured into water and extracted with ether. The organic phase is dried over sodium sulfate and concentrated in vacuo to give 9.9 g of a colorless oil. The oil is purified by column chromatography on silica gel using hexanes-EtOAc (2:1) as eluent to give 7.0 g (72%) of 4-phenylcyclohexylmethanol as an oil.

$^1$H NMR (300 MHz, CDCl$_3$) δ 7.36–7.20 (m, 5H), 3.75 (m, 1H), 3.56 (m, 1H), 2.59 (m, 1H), 2.08–1.15 (m, 10H) ppm.

Example 2c

4-Phenylcyclohexylmethyl Iodide

Imidazole (4.4 g, 0.065 mol) is added in one portion to a solution of triphenylphosphine (17.0 g, 0.065 mol) in dichloromethane (300 mL) at 25° C. After all of the solids dissolved, iodine (16.5 g, 0.065 mol) is added in four portions. The mixture is stirred for 10 min. then a solution of 4-phenylcyclohexylmethanol (10.5 g, 0.055 mol) is added dropwise and the mixture is stirred at 25° C. for 18 h. The reaction mixture is poured into pentane and the resulting solids filtered. The filtrate is concentrated in vacuo and the residue is dissolved in dichloromethane. This solution is poured into hexanes, the solids were filtered, and the filtrate is concentrated in vacuo. The residue is passed through a pad of silica gel using hexanes as eluent to afford 14.6 g (89%) of 4-phenylcyclohexylmethyl iodide as an oil.

$^1$H NMR (400 MHz, CDCl$_3$) δ 7.32–7.17 (m, 5H), 3.35 (dd, 1H), 3.17 (dd, 1H), 2.60 and 2.47 (two m, 1H), 2.05 (m, 1H), 1.95–1.84 (m, 2H), 1.77–1.64 (m, 3H), 1.56–1.47 (m, 2H), 1.18 (m, 1H) ppm.

Example 2d

Methyl (2R,3R)-3-Hydroxy-2-(4-phenylcyclohexylmethyl)butanoate

A solution of methyl (3R)-3-hydroxybutyrate (5.6 g, 0.047 mol) in THF (20 mL) is added dropwise to a solution of LDA prepared by dropwise addition of n-butyllithium (49.5 mL, 0.099 mol, 2 M in cyclohexane) to diisopropylamine (10.0 g, 0.099 mol) in THF (20 mL) at −78° C. After stirring at −50° C. to −40° C. for 0.5 h, a solution of 4-phenylcyclohexylmethyl iodide (14.6 g, 0.049 mol) in a mixture of HMPA (10 mL) and THF (15 mL) is added dropwise. The mixture is kept at −20° C. for 48 h, then allowed to warm to 4 ° C. and kept at that temperature for 48 h. The reaction mixture is chilled to 0° C. and quenched by dropwise addition of saturated aqueous ammonium chloride solution. The aqueous phase is extracted with ether and the combined organic phase is washed with ice-cold 0.1 M HCl, then saturated sodium chloride solution and dried over sodium sulfate. Concentration of the organic phase gives 14.6 g of crude product. Column chromatography on silica gel with hexanes-EtOAc (2:1) as eluent affords 4.18 g (31%) of methyl (2R,3R)-3-hydroxy-2-(4-phenylcyclohexylmethyl)butanoate as a pale yellow oil which solidified on standing.

$^1$H NMR (300 MHz, CDCl$_3$) δ 7.35–7.22 (m, 5H), 3.93 (m, 1H), 3.78 (s, 3H), 3.52 (m, 4H), 2.09–1.64 (m, 5H), 1.55–1.30 (m, 3H), 1.28 (d, 3H), 1.21–1.00 (m, 2H) ppm. Anal. Calcd. for C$_{18}$H$_{26}$O$_3$: C, 74.45; H, 9.03. Found: C, 74.52; H, 8.96.

Example 2e

(2R,3R)-3-Hydroxy-2-(4-phenylcyclohexylmethyl) butanoic Acid

A mixture of methyl (2R,3R)-3-hydroxy-2-(4-phenylcyclohexylmethyl)butanoate (4.17 g, 0.014 mol) and lithium hydroxide monohydrate (0.59 g, 0.014 mol) is stirred at 25° C. in a mixture of THF (30 mL), methanol (15 mL) and water (15 mL) for 72 h. The reaction is not complete and an additional 0.88 g (0.021 mol) of lithium hydroxide monohydrate in water (10 mL) is added. After 6 h an additional 0.59 g (0.014 mol) of solid lithium hydroxide monohydrate and the mixture is stirred at 25° C. for 18 h.

The mixture is concentrated in vacuo and the residue is taken up in water, chilled in an ice-bath and the pH is adjusted to 2 with sodium bisulfate. The mixture is extracted with dichloromethane. The combined extracts were washed with saturated sodium chloride, dried over sodium sulfate and concentrated in vacuo to give 3.43 g (89%) of (2R,3R)-3-hydroxy-2-(4-phenylcyclohexylmethyl)butanoic acid as a yellow solid.

$^1$H NMR (300 MHz, DMSO-$d_6$) δ 11.9 (br, 1H), 7.31–7.17 (m, 5H), 4.80 (br, 1H), 3.75 (m, 1H), 2.53–2.30 (m, 2H), 1.98–0.90 (m, 11H), 1.08 (d, 3H) ppm.

Example 2f (2R,3R)-3-Hydroxy-2-(4-phenylcyclohexylmethyl) butanoic Acid 2-Tetrahydropyranyloxyamide A mixture of (2R,3R)-3-hydroxy-2-(4-phenylcyclohexylmethyl)butanoic acid (3.43 g, 0.012 mol), 2-tetrahydropyranyloxyamine (1.64 g, 0.014 mol), BOP (5.75 g, 0.013 mol), HOBt (1.76 g, 0.13 mol) and NMM (2.63 g, 0.026 mol) in DMF (30 mL) is stirred at 25° C. for 18 h. The mixture is concentrated in vacuo and the residue is taken up in EtOAc. The mixture is washed with ice-cold 0.1 M HCl, saturated aqueous sodium bicarbonate, and saturated aqueous sodium chloride. The organic phase is dried over sodium sulfate and concentrated in vacuo to give 6.02 g of a white solid. Chromatography on silica gel using EtOAc as eluent gives 4.05 g (90%) of (2R,3R)-3-hydroxy-2-(4-phenylcyclohe,(ylmethyl)butanoic acid 2-tetrahydropyranyloxyamide as a white solid.

$^1$H NMR (400 MHz, DMSO-$d_6$) δ 10.90 (m, 1H), 7.25–7.10 (m, 5H), 4.81 (m, 1H), 4.53 (t, 1H), 3.90 (m, 1H), 3.61 (m, 1H), 3.45 (m, 1H), 2.39 (br t, 1H), 2.09 (m, 1H), 1.95 (m, 1H), 1.73–0.85 (m, 16H), 1.01 (d, 3H) ppm.

Example 2g (3R,4S)-1-(2-Tetrahydropyranyloxy)-3-(4-phenylcyclohexylmethyl)-4-methylazetidin-2-one Myethanesulfonyl chloride (1.4 g, 0.012 mol) is added dropwise to a solution of (2R,3R)-3-hydroxy-2-(4-phenylcyclohexylmethyl)butanoic acid 2-tetrahydropyranyloxyamide (4.02 g, 0.011 mol) in pyridine (30 mL) at 0° C. After 3 h at 25° C. the mixture is concentrate in vacuo and the. residue is taken up in a mixture of EtOAc and cold 1M HCl. The organic phase is washed with cold 1 M HCl and saturated sodium chloride solution. The organic phase is dried over sodium sulfate and concentrated in vacuo to give the crude methanesulfonate as a white foam $^1$H NMR (400 MHz, DMSO-$d_6$) δ 11.25 (d, 1H), 7.25–7.12 (m, 5H), 4.86 (br s, 1H), 4.63 (m, 1H), 4.10 (m, 2H), 3.98 (m, 1H), 3.02 (d, 3H), 2.41 (m, 2H), 2.00 (m, 1H), 1.74–0.80 (m, 15H), 1.33 (dd, 3H) ppm.

A solution of the above mesylate (5.0 g, 0.011 mol) in acetone (30 mL) is added dropwise to a mixture of potassium carbonate (4.7 g, 0.034 mol) in refluxing acetone (100 mL). After refluxing for 18 h, the mixture is filtered and the filtrate is concentrated in vacuo. The residue is purified by column chromatography on silica gel with hexanes-EtOAc (1:1) as eluent to give 3.85 g (98%) of (3R,4S)-1-(2-tetrahydropyranyloxy)-3-(4-phenylcyclohexylmethyl)-4-methylazetidin-2-one as an oil.

$^1$H NMR (300 MHz, DMSO-$d_6$) δ 7.32–7.18 (m, 5H), 5.05 (d, 1H), 4.06 (m, 2H), 3.57 (br t, 1H), 3.10 (m, 1H), 2.52 (m, 1H), 1.95–1.39 (m, 15H), 1.24 (dd, 3H), 1.09 (m, 2H) ppm. ESI-MS m/z 358 (M+H)$^+$. Anal. Calcd. for $C_{22}H_{31}NO_3$: C, 73.91; H, 8.74; N, 3.92. Found: C, 73.66; H, 8.77; N, 3.89.

Example 2h (2R,3S)-2-(4-phenylcyclohexylmethyl)-3-(2-tetrahydropyranyloxyamino)butanoic acid A solution of 3 N sodium hydroxide (18.7 mL) is added dropwise to a solution of (3R,4S)-1-(2-tetrahydropyranyloxy)-3-(4-phenylcyclohexylmethyl)-4-methylazetidin-2-one (3.6 g, 0.010 mol) in dioxane (50 mL) at 25° C. and the mixture is stirred for 18 h. Water (10 mL) is added to the reaction mixture and an additional 5 mL of 3 N sodium hydroxide is added dropwise and the mixture is stirred an additional 8 h. The reaction mixture is mixed with water (200 mL), 1 M sodium hydrogen sulfate (60 mL) and EtOAc (100 mL). The aqueous phase is extracted with EtOAc. The combined organic phase is washed with water and saturated sodium chloride solution, dried (sodium sulfate) and concentrated in vacuo to give 3.44 g (92%) of (2R,3S)-2-(4-phenylcyclohexylmethyl)-3-(2-tetrahydropyranyloxyamino)butanoic acid as a white solid. The product is used without further purification.

$^1$H NMR (300 MHz, DMSO-$d_6$) δ 12.07 (br, 1H), 7.28–7.17 (m, 5H), 6.52 (br, 1H), 4.70 (br d, 1H), 3.81 (m, 1H), 3.45 (m, 1H), 3.05 (m, 1H), 2.55 (m, 2H), 1.93–1.12 (m, 17H), 1.03 (dd, 3H) ppm. ESI-MS m/z 3.74 (M–H)$^-$.

Example 2i (2R,3S)-3-(Formyl-2-tetrahydropyranyloxyamino)-2-(4-phenylcyclohexylmethyl)butanoic acid Formic acetic anhydride (2.03 g, 0.023 mol) is added via syringe to a mixture of (2R,3S)-2-(4-phenylcyclohexylmethyl)-3-(2-tetrahydropyranyloxyamino)butanoic acid (3.44 g, 0.009 mol) in pyridine (35 mL) at 0° C. The mixture is allowed to come to 25° C. Additional formic acetic anhydride (0.97 g, 0.011 mol) is added. The mixture is stirred at 25° C. for 8 h and concentrated in vacuo. The residue is taken up in diethyl ether and washed with saturated aqueous copper sulfate solution, water, saturated sodium chloride solution and dried over sodium sulfate. Concentration in vacuo gives 3.65 g of (2R,3S)-3-(formyl-2-tetrahydropyrayloxyamino)-2-(4-phenylcyclohexylmethyl)butanoic acid as a foam. The product is used without further purification.

$^1$H NMR (300 MHz, DMSO-$d_6$) δ 12.55 (br, 1H), 8.43 and 8.20 (two m, 1H), 7.31–7.15 (m, 5H), 4.92 (m, 1H), 4.29 (m, 1H), 3.95 (m, 1H), 3.49 (m, 1H), 2.66 (m, 1H), 2.47 (m, 2H), 2.05–0.90 (m, 19H) ppm. ESI-MS m/z 402 (M–H)$^-$.

Example 2j

Pentafluorophenyl 3(2R,3S)-3-(Formyl-2-tetrahydropyranyloxyamino)-2-(4-phenylcyclohexylmethyl)butanoate To a solution of (2R,3S)-3-(formyl-2-tetrahydropyranyloxyamino)-2-(4-phenylcyclohexylmethyl)butanoic acid (3.65 g, 0.009 mol) in dichloromethane (20 mL) at 25° C. is added via syringe pyridine (0.87 g, 0.011 mol) followed by pentafluorophenyl trifluoroacetate (3.1 g, 0.011 mol). The mixture is stirred for 6 h, diluted with dichloromethane and washed with 0.1 M aqueous HCl, 1 M aqueous sodium carbonate, saturated aqueous sodium chloride and dried over sodium sulfate. Concentration in vacuo followed by chromatography on silica gel with hexanes-EtOAc (2:1) as eluent gives 3.05 g (60%) of pentafluorophenyl (2R,3S)-3-(formyl-2-tetrahydropyranyloxyamino)-2-(4-phenylcyclohexylmethyl)butanoate as an oil.

$^1$H NMR (300 MHz, DMSO-$d_6$) δ 8.49 and 8.30 (two m, 1H), 7.32–7.16 (m, 5H), 4.97 (br s, 1H), 4.48 and 4.22 (two m, 1H), 3.97 (m, 1H), 3.64 (m, 1H), 3.32 (m, 1H), 2.46 (m, 1H), 2.12–0.99 (m, 20H) ppm. Anal. Calcd. for $C_{29}H_{32}F_5NO_5$: C, 61.15; H, 5.66; N, 2.46. Found: C, 61.23; H, 5.71; N, 2.40.

Example 2k (2S)-2-tert-Butoxycarbonylamino-3,3-dimethylbutanoic Acid 1,3-Thiazol-2-ylamide A solution of 10.0 g (76.2 mmol) of (2S)-2-amino-3,3-dimethylbutanoic acid in 100 mL of THF and 50 mL of water is treated at 25° C. with 20 mL (100 mmol) of 5 N aqueous sodium hydroxide followed by 20 g (91.6 mmol) of di-tert-butyl dicarbonate. The mixture is stirred vigorously at 25° C. for 24 h. The mixture is chilled to 0° C. and is treated dropwise with saturated aqueous sodium bisulfate solution to adjust the reaction mixture to pH 2. The mixture is extracted with two 200-mL portions of EtOAc. The combined organic phases are dried over magnesium sulfate and concentrated in vacuo to afford 18.5 g of crude (2S)-2-tert-butoxycarbonylamino-3,3-dimethylbutanoic acid. The crude acid is stirred in 200 mL of DMF at 0° C. as 12.3 g (91.1 mmol) of HOBt, 30 mL (273 mmol) of NMM, and 17.5 g (91.2 mmol) of EDC are added in turn. After 30 min at 0° C. 9.1 g (90.1 mmol) of 2-amino-1,3-thiazole is added. The mixture is stirred at 0° C. for 30 min and at 50° C. for 2 h. The mixture is then concentrated in vacuo and the residue is diluted with 250 mL of EtOAc. The organic phase is washed with water, saturated aqueous sodium chloride, is dried over magnesium sulfate, and concentrated in vacuo. Chromatography on silica gel (elution with 30% EtOAc-hexanes followed by 70% EtOAc-hexanes) affords 20.1 g (84%) of (2S)-2-tert-butoxycarbonylamino-3,3-dimethylbutanoic acid 1,3-thiazol-2-ylamide as an oil.

$^1$H NMR (300 MHz, CDCl$_3$) δ 7.52 (d, 1H), 7.03 (d, 1H), 5.42 (bd, 1H), 3.41 (s, 1H), 1.43 (s, 9H), 1.12 (s, 9H) ppm.

Example 2l (2S)-2-Amino-3,3-dimethylbutanoic Acid 1,3-Thiazol-2-ylamide

A solution of 18.3 g (58.4 mmol) of (2S)-2-tert-butoxycarbonylamino-3,3-dimethylbutanoic acid 1,3-thiazol-2-ylamide in 50 mL of dichloromethane is treated dropwise at 25° C. with 50 mL of TFA. After 4 h at 25° C. the mixture is concentrated in vacuo and the residue is diluted with 20 mL of dichloromethane. The mixture is stirred at 0° C. as saturated aqueous sodium carbonate is added dropwise to bring the mixture to pH 8. The mixture is diluted with water to a volume of 200 mL and the solid product is collected and dried in vacuo affording, 11.6 g (93%) of (2S)-2-amino-3,3-dimethylbutanoic acid 1,3-thiazol-2-ylamide.

$^1$H NMR (300 MHz, CDCl$_3$) δ 7.50 (d, 1IH), 7.01 (d, 1H), 3.42 (s, 1H), 1.62 (bs, 2H), 1.11 (s, 9H) ppm.

Example 2m (2R,3S)-3-(Formyl-tetrahydropyranyloxyamino)-2-(4-phenylcyclohexylmethyl)butanoic Acid [(1S)-2,2-Dimethyl-1-(1,3-thiazol-2-ylcarbamoyl)-1-propyl]amide A mixture of pentafluorophenyl (2R,3S)-3-(formyl-2-tetrahydropyranyloxyamino)-2-(4-phenylcyclohexylmethyl)butanoate (0.25 g, 0.44 mmol), (2S)-2-amino-3,3-dimethylbutanoic acid 1,3-thiazol-2-ylamide (0.10 g, 0.49 mmol), HOBt (6.1 mg, 0.040 mmol) and TEA (0.07 g, 0.67 mmol) in DMF (3 mL) is heated at 41° C. for 18 h. The reaction mixture is poured into a mixture of hexanes (100 mL) and EtOAc (100 mL) and the resulting mixture is washed with water, 1 M aqueous sodium carbonate and water. The organic phase is dried (sodium sulfate) and concentrated in vacuo and the residue is purified by column chromatography on silica gel with EtOAc-hexanes (1:1) as eluent to give 0.12 g (46%) of (2R,3S)-3-(formyltetrahydropyranyloxyamino)-2-(4-phenylcyclohexylmethyl)butanoic acid [(1S)-2,2-dimethyl-1-(1,3-thiazol-2-ylcarbamoyl)-1-propyl]amide as a white solid.

$^1$H NMR (400 MHz, DMSO-$d_6$) δ 12.36 (m, 1IH), 8.40 (m, 1H), 8.32 and 8.09 (two s, 1H), 7.50 (m, 1H), 7.23–7.06 (m, 4H), 6.80 (m, 2H), 4.91 and 4.79 (two m, 1H), 4.27 and 4.12 (two m, 1H), 3.89 and 3.78 (two m, 1H), 3.53 (m, 1H), 3.02 (m, 1H), 2.27 (m, 1H), 2.05 (m, 1H), 1.86–1.22 (m, 10H), 1.00 (m, 6H), 0.95 (s, 9H), 0.91 (m, 1H), 0.74 (m, 2H) ppm. ESI-MS m/z 597 (M–H)$^{31}$.

Example 2

(2R,3S)-3-(Formyl-hydroxyamino)-2-(4-phenylcyclohexylmethyl)butanoic Acid [(1S)-2,2-Dimethyl-1-(1,3-thiazol-2-ylcarbamoyl)-1-propyl]amide A mixture of (2R,3S)-3-(formyl-tetrahydropyranyloxyamino)-2-(4-phenylcyclohexylmethyl)butanoic acid [(1S)-2,2-dimethyl-1-(1,3-thiazol-2-ylcarbamoyl)-1-propyl]amide (0.12 g, 0.20 mmol) in 80% acetic acid (10 mL) is heated at 40° C. for 18 h. The mixture is concentrated in vauco, the residue is taken up in ethanol and concentrated in vacuo. Repeating the ethanol treatment several times and addition of water is followed by stirring at 25° C. for 18 h. The resulting solid is filtered, washed with water, and dried to give 0.083 g (80%) of (2R,3S)-3-(formyl-hydroxyamino)-2-(4-phenylcyclohexylmethyl)butanoic acid [(1S)-2,2-dimethyl-1-(1,3-thiazol-2-ylcarbamoyl)-1-propyl]amide as a white solid, m.p. 213–214° C.

$^1$H NMR (300 MHz, DMSO-$d_6$) δ 12.33 (s, 1H), 9.82 and 9.45 (two s, 1H), 8.35 and 8.02 (two s, 1H), 7.:54 (d, 1H), 7.19 (m, 4H), 6.92 (d, 2H), 4.76 (d, 1H), 4.34 and 3.76 (two m, 1H), 2.98 (m, 1H), 2.32 (m, 1H), 2.06 (m, 1H), 1.72–0.76 (m, 22H) ppm. ESI-MS m/z 513 (M–H)$^-$. Anal. Calcd. for $C_{27}H_{38}N_4O_4S \cdot 0.3$ $C_2H_4O_2$: C, 62.23; H, 7.42; N, 10.52. Found: C, 62.44; H, 7.46; N, 10.32.

Example 3

(2R,3S)-3-(Formyl-hydroxyamino)-2-(3-phenyl-1-propyl)hexanoic Acid [(1S)-5-Benzyloxycarbonylamino-1-(1,3,4-thiadiazol-2-yl-carbamoyl)-1-pentyl]amide

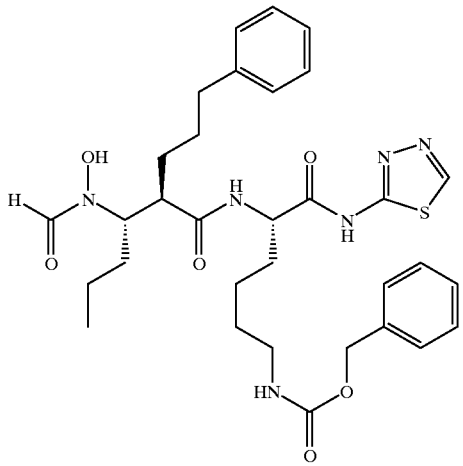

Example 3a

Ethyl (3R)-3-Hydroxyhexanoate and Methyl (3R)-3-Hydroxyhexanoate

Ethyl butyrylacetate (50.0 g, 316 mmol) is stirred in 75 mL of absolute ethanol as [RuCl$_2$(BINAP)]$_2$•NEt$_3$ (0.139 g, 0.158 mmol) is added along with 2 N hydrochloric acid (0.158 mL, 0.316 mmol). The mixture is placed on a pressure hydrogenation apparatus and degassed by evacuating and filling with nitrogen several times. The vessel is then pressurized with hydrogen to 65 psi. The reaction is heated to 70° C. for 36 h and then is allowed to cool to 25° C. The resulting reddish brown solution is concentrated under reduced pressure and the product distilled (40–50° C., 200 millitorr) to give a clear oil (50.0 g, 99% yield, >99% enantiomeric excess determined by chiral analytical HPLC).

$^1$H NMR (400 MHz, CDCl$_3$) δ 4.17 (q, 2H), 4.01 (m, 1H), 2.95 (d, 1H), 2.47 (dd, 1H), 2.40 (dd, 1H), 1.58–1.38 (m, 4H), 1.38 (t, 3H), 0.94 (t, 3H) ppm.

Methyl (3R)-3-hydroxyhexanoate is prepared in the same manner described above in methanol employing methyl butyrylacetate as the starting ketoester. The enantiomeric excess is 99% as determined by chiral analytical HPLC methods.

$^1$H NMR (300 MHz, CDCl$_3$) δ 4.04 (m, 1H), 3.72 (s, 3H), 2.87 (d, 1H), 2.50 (dd, 1H), 2.46 (dd, 1H), 1.58–1.38 (m, 4H), 0.94 (t, 3H) ppm.

Example 3b

Ethyl (2R,3R)-2-[(2E)-3-Phenyl-2-propen-1-yl]-3-hydroxyhexanoate

To a solution of diisopropylamine (2.28 g, 20.63 mmol) in THF (20 mL) cooled to 0° C. is added n-butyllithium (20.63 mmol, 2.5 M in hexanes) and the resulting solution is stirred at 0° C. or 0.5 h. The reaction mixture is cooled to –50° C. followed by slow addition of ethyl (3R)-3-hydroxyhexanoate (1.5 g, 9.38 mmol). After 0.5 h a solution of cinnamyl bromide (2.67 g, 14.06 mmol) in HMPA (2 mL) is added and the reaction mixture is allowed to warm to –20° C. and stirred for 16 h. The reaction mixture is quenched by addition 3 mL of saturated aqueous ammonium chloride solution, is poured into 20 mL of 1 N hydrochloric acid, and is extracted with two 50-mL portions of EtOAc. The combined organic layers are dried over magnesium sulfate, concentrated in vacuo, and purified by silica gel chromatography (elution with 25% EtOAc-hexanes) to afford ethyl (2R,3R)-2-[(2E)-3-phenyl-2-propen-1-yl]-3-hydroxyhexanoate as a yellow oil (1.82 g, 70% yield).

$^1$H NMR (300 MHz, CDCl$_3$) δ 7.42–7.22 (m, 5H), 6.52 (d, 1H), 6.20 (dt, 1H), 4.22 (q, 2H), 3.78 (m, 1H), 2.64 (m, 4H), 1.54 (m, 2H), 1.26 (t, 3H), 0.96 (t, 3H) ppm. APCI-MS m/z 299 (M+Na)$^+$.

Example 3c

Ethyl (2R,3R)-2-(3-Phenyl-1-propyl)-3-hydroxyhexanoate

A solution of ethyl (2R,3R)-2-[(2E)-3-phenyl-2-propen-1-yl]-3-hydroxyhexanoate (1.76 g, 6.38 mmol) in 30 mL of EtOAc is treated with 200 mg of 10% palladium on carbon. The resulting suspension is repeatedly evacuated and purged with a hydrogen balloon, then stirred under 1 atmosphere pressure of hydrogen gas for 6 h. The catalyst is filtered and the filtrate is concentrated in vacuo to provide ethyl (2R,3R)-2-(3-phenyl-1-propyl)-3-hydroxyhexanoate as an oil (1.70 g, 96% yield).

$^1$H NMR (300 MHz, CDCl$_3$) δ 7.42–7.20 (m, 5H), 4.22 (q, 2H), 3.70 (m, 1H), 2.64 (m, 2H), 2.52 (m, 2H), 1.82 (m, 1H), 1.70–1.40 (m, 6H), 1.26 (t, 3H), 0.96 (t, 3H) ppm. APCI-MS m/z 301 (M+Na)$^+$.

Example 3d (2R,3R)-2-(3-Phenyl-l1-propyl)-3-hydroxyhexanoic Acid

To a solution of ethyl (2R,3R)-2-(3-phenyl-1-propyl)-3-hydroxyhexanoate (1.70 g, 6.12 mmol) in THF-ethanol (2:1, 18 mL) is added 1 N aqueous sodium hydroxide solution (6.7 mL, 6.7 mmol). The solution is stirred at 23° C. for 20 h and is acidified to pH 3 with saturated aqueous sodium bisulfate and is extracted with two 50-mL portions of EtOAc. The combined organic layers are dried over anhydrous magnesium sulfate and concentrated under reduced pressure to provide (2R,3R)-2-(3-phenyl-1-propyl)-3-hydroxyhexanoic acid as an oil (1.53 g, 100% yield).

$^1$H NMR (300 MHz, CDCl$_3$) δ 7.40–7.20 (m, 5H), 3.78 (m, 1H), 2.74 (m, 2H), 2.56 (m, 1H), 1.94–1.64 (m, 4H), 1.58–1.40 (m, 4H), 0.96 (t, 3H) ppm. APCI-MS m/z 273 (M+Na)$^+$.

Example 3e (2R,3R)-2-(3-Phenyl-1-propyl)-3-hydroxyhexanoic Acid 2-Tetrahydropyranyloxyamide To a solution of (2R,3R)-2-(3-phenyl-1-propyl)-3-hydroxyhexanoic acid (1.53 g, 6.12 mmol) in dichloromethane (6 mL) is added 2-tetrahydropyranyloxyamine (0.93 g, 7.96 mmol) and EDC (1.29 g, 6.73 mmol). The resulting solution is stirred at 23° C. for 3 h, concentrated in vacuo, and diluted with 50 mL of EtOAc. The organic layer is washed sequentially with 1 N hydrochloric acid, saturated aqueous sodium bicarbonate solution, saturated aqueous sodium chloride solution, and is dried over anhydrous magnesium sulfate. Concentration under reduced pressure and purification by silica gel chromatography (elution with 2:1 EtOAc-hexanes) provides (2R,3R)-2-(3-phenyl-1-propyl)-3-hydroxyhexanoic acid 2-tetrahydropyranyloxyamide as a solid (1.62 g, 76% yield).

$^1$H NMR (400 MHz, CDCl$_3$) δ 7.25 (m, 2H), 7.18 (m, 3H), 4.95 (m, 1H), 3.93 (m, 1H), 3.62 (m, 2H), 2.80 (d, 1H), 2.62 (t, 2H), 2.04 (m, 1H), 1.84 (m, 4H), 1.66–1.54 (m, 6H), 1.46–1.30 (m, 4H), 0.96 (t, 3H) ppm. APCI-MS m/z 372 (M+Na)$^+$.

Example 3f (3R,4S)-1-(2-Tetrahydropyranyloxy)-3-(3-phenyl-1-propyl)-4-propylazetidin-2-one To a solution of (2R,3R)-2-(3-phenyl-1-propyl)-3-hydroxyhexanoic acid 2-tetrahydropyranyloxyamide (1.62 g, 4.64 mmol) in 7 mL of dichloromethane at 0° C. is added pyridine (1 mL) and methanesulfonyl chloride (0.58 g, 5.10 mmol). The resulting solution is allowed to warm to 23° C. and is stirred at 23° C. for 24 h, concentrated in vacuo, and diluted with EtOAc (40 mL). The organic layer is washed with 1 N hydrochloric acid, saturated aqueous cupric sulfate solution, dried over anhydrous magnesium sulfate, and concentrated to provide the desired methanesulfonate intermediate.

A suspension of potassium carbonate (1.92 g) in acetone (90 mL) is heated to reflux for 1 h. A solution of the above methanesulfonate in acetone (10 mL) is added and the resulting suspension is heated at reflux for 1 h. The mixture is allowed to cool to 25° C. and is filtered, concentrated under reduced pressure, and purified by silica gel chromatography (elution with 2:1 hexanes-EtOAc) to provide (3R,4S)-1-(2-tetrahydropyranyloxy)-3-(3-phenyl-1-prop)y)-4-propylazetidin-2-one as an oil (1.22 g, 79% yield).

$^1$H NMR (300 MHz, CDCl$_3$) δ 7.25 (m, 2H), 7.18 (m, 3H), 5.20 and 5.02 (two m, 1H), 4.30–4.08 (m, 1H), 3.92 (m, 1H), 3.62 (m, 1H), 2.98 (m, 1H), 2.68 (m, 2H), 1.96 (m, 1H), 1.84–1.32 (m, 13H), 0.96 (m, 3H) ppm. APCI-MS m/z 354 (M+Na)$^+$.

Example 3g (2R,3S)-2-(3-Phenyl-1-propyl)-3-(2-tetrahydropyranyloxyamino)hexanoic Acid To a solution of (3R,4S)-1-(2-tetrahydropyranyloxy)-3-(3-phenyl-1-propyl)-4-propylazetidin-2-one (1.22 g, 3.69 mmol) in THF-methanol (2:1, 15 mL) is added 1 N aqueous sodium hydroxide (5.5 mL). The solution is stirred at 23° C. for 36 h, is acidified to pH 3 with saturated aqueous sodium bisulfate solution, and is extracted with two 100-mL portions of EtCOAc. The combined organics are dried over anhydrous sodium sulfate and concentrated under reduced pressure to provide (2R,3s)-2-(3-phenyl-1-propyl)-3-(2-tetrahydropyranyloxyamino)hexanoic acid as an oil (0.93 g, 72% yield).

$^1$H NMR (300 MHz, CDCl$_3$) δ 7.34 (m, 2H), 7.21 (m, 3H), 4.84 and 4.75 (two m, 1H), 4.06 and 3.94 (two m, 1H), 3.62 (m, 1H), 3.20 and 3.10 (two m, 1H), 3.01 and 2.92 (two m, 1H), 2.62 (m, 1H), 1.96–1.21 (m, 14H), 0.96 (m, 3H) ppm. APCI-MS m/z 350 (M+H)$^+$.

Example 3h

Pentafluorophenyl (2R,3S)-2-(3-Phenyl-1-propyl)-3-(formyl-2-tetrahydropyranyloxyamino)hexanoate To a solution of (2R,3S)-2-(3-phenyl-1-propyl)-3-(2-tetrahydropyranyloxyamino)hexanoic acid (0.93 g, 2.66 mmol) in pyridine (2 mL) at 0° C. is added formic acetic anhydride (0.4 mL). The resulting solution is stirred at 0° C. for 1 h, concentrated in vacuo, and diluted with 11 mL of EtOAc. To the solution of crude acid is added pentafluorophenol (0.51 g, 2.79 mmol), NMM (0.28 g, 2.79 mmol) and dicyclohexylcarbodiimide (0.58 g, 2.79 mmol). The resulting solution is stirred at 23° C. for 20 h and is filtered. The filtrate is washed with 1 N hydrochloric acid, 1 M aqueous sodium carbonate solution, and saturated aqueous sodium chloride solution. The organic layer is dried over magnesium sulfate, concentrated, and purified by silica gel chromatography (elution with 9:1 hexanes-EtOAc) to provide pentafluorophenyl (2R,3S)-2-(3-phenyl-1-propyl)-3-(formyl-2-tetrahydropyranyloxyamino)hexanoate as an oil (0.84 g, 58% yield).

$^1$H NMR (400 MHz, CDCl$_3$) δ 8.56 and 8.02 (two s, 1H), 7.28–7.14 (m, 5H), 4.76 and 4.72 (two m, 1H), 4.56 and 3.68 (m, 1H), 3.96 (m, 1H), 3.56 (m, 1H), 3.18 and 3.02 (two m, 1H), 2.64 (m, 2H), 2.02–1.38 (m, 14H), 0.90 (m, 3H) ppm. APCI-MS m/z 566 (M+Na)$^+$.

Example 3i (2S)-6-Benzyloxycarbonylamino-2-tert-butoxycarbonylaminohexanoic Acid 1,3,4-Thiadiazol-2-ylamide To a solution of (2S)-6-benzyloxycarbonylamino-2-tert-butoxycarbonylaminohexanoic acid (1.09 g, 2.87 mmol) in dichloromethane (5 mL) is added 1,1-carbonyldiimidazole (0.47 g, 2.87 mmol). The resulting solution is stirred at 25° C. for 1 h and 2-amino-1,3,4-thiadiazole (0.29 g, 2.87 mmol) is added and the reaction is stirred for an additional 18 h. The mixture is diluted with dichloromethane (60 mL) and washed with 1 M aqueous sodium carbonate solution. The organic layer is dried over anhydrous magnesium sulfate, concentrated in vacuo, and purified by silica gel chromatography (elution with 1:1 EtOAc-hexanes) to provide (2S)-6-benzyloxycarbonylamino-2-tert-butoxycarbonylaminohexanoic acid 1,3,4-thiadiazol-2-ylamide as a foam (0.81 g, 61% yield).

$^1$H NMR (300 MHz, CDCl$_3$) δ 13.35 (bs, 1H), 8.78 (bs, 1H), 7.32 (m, 5H), 6.56 (m, 1H), 5.09 (m, 3H), 4.46 (m, 1H), 3.21 (m, 2H), 2.91 (m, 2H), 1.95–1.56 (m, 4H), 1.26 (s, 9H) ppm. APCI-MS m/z 464 (M+H)$^+$.

Example 3j (2S)-6-Benzyloxycarbonylamino-2-aminohexanoic Acid 1,3,4-Thiadiazol-2-ylamide To a solution of (2S)-6-benzyloxycarbonylamino-2-tert-butoxycarbonylaminohexanoic acid 1,3,4-thiadiazol-2-ylamide (0.81 g, 1.75 mmol) in dichloromethane (8 mL) is added trifluoroacetic acid (2 mL). The resulting solution is stirred for 4 h at 25° C., is concentrated, diluted with 50 mL of EtOAc, and washed with 1 N aqueous sodium hydroxide solution. The organic layer is dried over anhydrous sodium sulfate and concentrated under reduced pressure to provide (2S)-6-benzyloxycarbonylamino-2-aminohexanoic acid 1,3,4-thiadiazol-2-ylamide as a solid (0.62 g, 98% yield).

$^1$H NMR (300 MHz, CDCl$_3$) δ 8.82 (s, 1H), 7.31 (m, 5H), 5.42 (bs, 1H), 5.04 (s, 2H), 3.64 (m, 1H), 3.16 (m, 4H), 1.85 (m, 1H), 1.62 (m, 1H), 1.51 (m, 4H) ppm. APCI-MS m/z 364 (M+H)$^+$.

Example 3k (2R,3S)-3-(Formyl-2-tetrahydropyranyloxyamino)-2-(3-phenyl-1-propyl)hexanoic Acid [(1S)-5-Benzyloxycarbonylamino-1-(1,3,4-thiadiazol-2-ylcarbamoyl)-1-pentyl]amide To a solution of pentafluorophenyl (2R,3S)-2-(3-phenyl-1-propyl)-3-(formyl-2-tetrahydropyranyloxyamino)

hexanoate (90 mg, 0.166 mmol) in DMF (0.5 mL) is added (2S)-6-benzyloxycarbonylamino-2-aminohexanoic acid 1,3,4-thiadiazol-2-ylamide (78 mg, 0.215 mmol) and HOBt (2.2 mg, 0.017 mmol). The resulting solution is heated to 50° C. and is stirred for 18 h. The reaction mixture is cooled to 25° C., concentrated in vacuo, diluted with 20 mL of EtOAc, and washed with 1 M aqueous sodium carbonate solution. The organic layer is dried over magnesium sulfate, concentrated in vacuo, and purified by silica gel chromatography (elution with 2:1 EtOAc-hexane) to provide (2R,3S)-3-(formyl-2-tetrahydropyranyloxyamino)-2-(3-phenyl-1-propyl)hexanoic acid [(1S)-5-benzyloxycarbonylamino-1-(1,3,4-thiadiazol-2-ylcarbamoyl)-1-pentyl]amide as an oil (24.1 mg, 25% yield). APCI-MS m/z 745 (M+Na)+.

Example 3

(2R,3S)-3-(Formyl-hydroxyamino)-2-(3-phenyl-1-propyl)hexanoic Acid [(1S)-5-Benzyloxycarbonylamino-1-(1,3,4-thiadiazol-2-ylcarbamoyl)-1-pentyl]amide A solution of (2R,3S)-3-(formyl-2-tetrahydropyranyloxyamino)-2-(3-phenyl-1-propyl)hexanoic acid [(1s)-5-benzyloxycarbonylamino-1-(1,3,4-thiadiazol-2-ylcarbamoyl)-1-pentyl]amide (23 mg, 0.032 mmol) in acetic acid-water (4:1, 1 mL) is heated to 50° C. for 16 h. The reaction mixture is concentrated, then dissolved in toluene and concentrated in vacuo. The procedure is repeated once again to afford the crude product which is recrystallized from dichloromethane-methanol-diethyl ether to provide (2R,3S)-3-(formyl-hydroxyamino)-2-(3-phenyl-1-propyl)hexanoic acid [(1S)-5-benzyloxycarbonylamino-1-(1,3,4-thiadiazol-2-ylcarbamoyl)-1-pentyl]amide as a solid (14 mg, 69% yield).

$^1$H NMR (400 MHz, CD$_3$OD) δ 9.04 (s, 1H), 8.35 and 7.95 (two s, 1H), 7.30 (m, 5H), 7.12 (m, 5H), 5.03 i(m, 2H), 4.57 (m, 1H), 4.39 and 3.61 (two dt, 1H), 3.11 (t, 2H), 2.78–2.46 (m, 2H), 1.78–1.14 (m, 14H), 0.88 (m, 3H) ppm. APCI-MS m/z 585 (M+Na)+. Anal. Calcd. for C$_{26}$H$_{38}$N$_6$O$_6$S.0.5 H$_2$O: C, 54.62; H, 6.87; N, 14.70. Found: C, 54.70; H 6.72; N, 14.41.

Example 195

(2R,3S)-3-(Formylhydroxyamino)-2-(3-(4-chlorophenyl)-1-propyl)butanoic Acid [(1S)-2,2-Dimethyl-(1-(3-pyridyl)carbamoyl)-1-propyl]amide

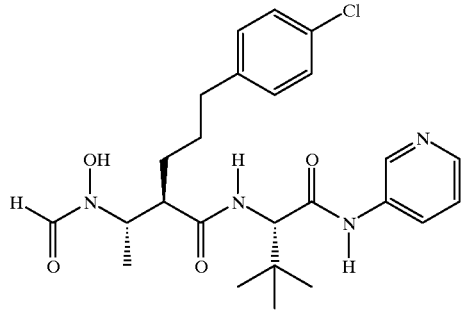

Example 195a

Methyl (2R,3R)-2-(3-trimethylsilyl-2-propyne-1-yl)-3-hydroxybutanoate

To a solution of diisopropylamine (9.42 g, 93.22 mmol) in THF (100 mL) cooled to −50° C. is added n-butyllithium (93.22 mmol, 2.5M in hexanes) and the resulting solution is stirred at −50° for 0.5 h. The reaction mixture is cooled to −78° C. followed by slow addition of methyl (3R)-3-hydroxybutanoate (5 g, 42.37 mmol). After 0.5 h a solution of 3-trimethylsilylropargyl bromide (9.76 g, 50.85 mmol) in HMPA (1 mL) is added and the reaction mixture is allowed to warm to 0° C. and stirred for 16 h. The reaction mixture is quenched by addition 10 mL of saturated aqueous ammonium chloride solution, is poured into 100 mL of 1 M hydrochloric acid, and is extracted with two 100 mL portions of EtOAc. The combined organic layers are dried over magnesium sulfate, concentrated in vacuo, and purified by silica gel chromatography (elution with 20% EtOAc-hexanes) to afford methyl (2R,3R)-2-(3-trimethylsilyl-2-propyne-1-yl)-3-hydroxybutanoate as a yellow oil (5.6 g, 58% yield).

$^1$H NMR (400 MHz, CDCl$_3$) δ 4.04 (m, 1H), 3.72 (s, 3H), 2.62 (m, 3H), 1.23 (t, 3H), 0.09 (s, 9H) ppm. ESI-MS m/z 251.2 (M+Na)+.

Example 195b (2R,3R)-2-(2-propyne-1-yl)-3-hydroxybutanoic Acid

To a solution of methyl (2R,3R)-2-(3-trimethylsilyl-2-propyne-1-yl)-3-hydroxybutanoate (5.6 g, 24.56 mmol) in THF-methanol (3:1, 160 mL) is added 2 M aqueous sodium hydroxide solution (40 mL, 36.8 mmol). The solution is stirred at 23° C. for 20 h, then concentrated and extracted with hexanes (100 mL). The aqueous layer is acidified to pH 3 with 1 M HCl and is extracted with two 100 mL portions of EtOAc. The combined organic layers are dried over anhydrous magnesium sulfate and concentrated under reduced pressure to provide (2R,3R)-2-(2-propyne-1-yl)-3-hydroxybutanoic acid as an oil (3.0 g, 86% yield).

$^1$H NMR (400 MHz, CDCl$_3$) δ 7.28 (m, 2H), 7.16 (m, 3H), 3.93(m, 1H), 2.63 (m, 2H), 2.43 (m, 1H), 1.69 (m, 4H), 1.26 (d, 3H) ppm. ESI-MS m/z 221.3 (M−H)−.

Example 195c (2R,3R)-2-(2-propyne-1-yl)-3-hydroxybutanoic Acid 2-Tetrahydropyrziyloxyamide To a solution of (2R,3R)-2-(2-propyne-1-yl)-3-hydroxybutanoic acid (3.0 g, 21.13 mmol) in dichloromethane (50 mL) is added 2-tetrahydropyranyloxyamine (3.0 g, 25.35 mmol) and EDC (4.5 g, 23.24 mmol). The resulting solution is stirred at 23° C. for 4 h, then diluted with dichloromethane (100 mL) and washed with 1 M hydrochloric acid. The combined organic layers were dried over anhydrous magnesium sulfate and concentrated under reduced pressure to provide (2R,3R)-2-(2-propyne-1-yl)-3-hydroxybutanoic acid 2-tetrahydropyranyloxyamide as a foam (1.9 g, 37% yield). $^1$H NMR (400 MHz, CDCl$_3$) δ 8.82 (bs, 1H), 4.96 (m, 1H), 3.94 (m, 2H), 3.62 (m, 1H), 2.64 (m, 1H), 2.56 (m, 1H), 2.23 (m, 1H), 2.04 (m, 1H), 1.82 (m, 2H), 1.61 (m, 4H), 1.23 (d, 3H) ppm. ESI-MS m/z 240.4 (M−H)−.

Example 195d (3R,4S)-1-(2-Tetrahydropyranyloxy)-3-(2-propyne-1-yl)-4-methylazetidin-2-one To a solution of (2R,3R)-2-(2-propyne-1-yl)-3-hydroxybutanoic acid 2-tetrahydropyranyloxyamide (1.9 g, 7.88 mmol) in 20 mL of dichloromethane at 0° C. is added pyridine (5 mL) and methanesulfonyl chloride (0.99 g, 8.67 mmol). The resulting solution is allowed to warm to 23° C.

and is stirred at 23° C. for 16 h, concentrated in vacuo, and diluted with dichloromethane (100 mL). The organic layer is washed with 1 M hydrochloric acid, saturated aqueous sodium chloride solution, dried over anhydrous magnesium sulfate, and concentrated to, provide the desired methanesulfonate intermediate.

A suspension of potassium carbonate (3.26 g) in acetone (10 mL) is heated to reflux for 1 h. A solution of the above methanesulfonate in acetone (100 mL) is added and the resulting suspension is heated at reflux for 6 h. The mixture is allowed to cool to 25° C. and is filtered, concentrated under reduced pressure, and purified by silica gel chromatography (elution with 4:1 hexanes-EtOAc) to provide (3R, 4S)-1-(2-tetrahydropyranyloxy)-3-(2-propyne-1-yl)-4-methylazetidin-2-one as an oil (1.3 g, 74% yield).

$^1$H NMR (400 MHz, CDCl$_3$) δ 5.15 (m, 0.5H), 4.99 (m, 0.5H), 4.20–4.01 (m, 2H), 3.62 (m, 1H), 3.18 (m, 1H), 2.63 (m, 1H), 2.40 (m, 1H), 1.99 (m, 1H), 1.89–1.51 (m, 6H), 1.42 (d, 1.5H), 1.38 (d, 1.5H) ppm. ESI-MS m/z 246.3 (M+Na)$^+$.

Example 195e (3R,4S)-1-(2-Tetrahydropyranyloxy)-3-((2E)-3-tributylstannyl-2-propene-1-yl)-4-methylazetidin-2-one To a solution of (3R,4S)-1-(2-tetrahydropyranyloxy)-3-(2-propyne-1-yl)-4-methylazetidin-2-one (1.32 g, 5.83 mmol) in 20 mL of toluene is added tributyltin hydride (1.70 g, 5.83 mmol) and AIBN (30 mg). The resulting solution is heated at reflux for 4 h then concentrated ir vacuo. The reaction mixture is purified by silica gel chromatography (elution with 8:1 hexanes-EtOAc) to provide (3R,4S)-1-(2-tetrahydropyranyloxy)-3-((2E)-3-tributylstannyl-2-propene-1-yl)-4-methylazetidin-2-one as an oil (2.6 g, 87% yield).

$^1$H NMR (400 MHz, CDCl$_3$) δ 5.94 (m, 2H), 5.16 (m, 0.5H), 4.99 (m, 0.5H), 4.20–4.01 (m, 2H), 3.62 (m, 1H), 3.12 (m, 1H), 2.61 (m, 1H), 2.36 (m, 1H), 1.76 (m, 2H), 1.58 (m, 4H), 1.44 (m, 6H), 1.26 (m, 9H), 0.86 (m, 15H) ppm. ESI-MS m/z 538.2 (M+Na)$^+$.

Example 195f (3R,4S)-1-(2-Tetrahydropyranyloxy)-3-((2E)-3-(4-chlorophenyl)-2-propene-1-yl)-4-methylazetidin-2-one To a solution of (3R,4S)-1-(2-tetrahydropyranyloxy)-3-((2E)-3-tributylstannyl-2-propene-1-yl)-4-methylazetidin-2-one (0.92 g, 1.79 mmol) in 3 mL of dimethylformamide is added 4-chloroiodobenzene (470 mg, 1.97 mmol) and triphenyphosphine palladium (II) dichloride (63 mg, 0.09 mmol). The resulting solution is heated at 80° C. for 16 h, then 0.5 mL ammonium hydroxide is added. The reaction mixture is poured into saturated sodium chloride solution (20 mL) and extracted with 1:1 EtOAc-hexane (50 mL). The combined organic layers were dried over anhydrous magnesium sulfate, concentrated under reduced pressure, and purified by silica gel chromatography (elution with 3:1 hexanes-EtOAc) to provide (3R,4S)-1-(2-tetrahydropyranyloxy)-3-((2E)-3-(4-chlorophenyl)-2-propene-1-methylazetidin-2-one as an oil (370 mg, 61% yield).

$^1$H NMR (400 MHz, CDCl$_3$) δ 7.30 (d, 2H), 7.16 (d, 2H), 6.38 (m, 1H), 6.18 (m, 1H), 5.16 (m, 0.5H), 4.99 (m, 0.5H), 4.20–4.01 (m, 2H), 3.62 (m, 1H), 3.12 (m, 1H), 2.62 (m, 1H), 2.42 (m, 1H), 1.76 (m, 2H), 1.58 (m, 4H), 1.36 (m, 3H) ppm. ESI-MS m/z 358.2 (M+Na)$^+$.

Example 195g (3R,4S)-1-(2-Tetrahydropyranyloxy)-3-(3-(4-chlorophenyl)-1-propyl)-4-methylazetidin-2-one To a solution of (3R,4S)-1-(2-tetrahydropyranyloxy)-3-((2E)-3-(4-chlorophenyl)-2-propene-1-yl)-4-methylazetidin-2-one (0.37 g, 1.10 mmol) in 5 mL of methanol is treated with 30 mg of 5% palladium on barium sulfate. The resulting suspension is repeatedly evacuated and purged with a hydrogen balloon, then stirred under 1 atmosphere pressure of hydrogen gas or 30 h. The catalyst is filtered and the filtrate is concentrated in vacuo to provide (3R,4S)-1-(2-tetrahydropyranyloxy)-3-(3-(4-chlorophenyl)-1-propyl)-4-methylazetidin-2-one as an oil (360 mg, 97% yield).

$^1$H NMR (400 MHz, CDCl$_3$) δ 7.22 (d, 2H), 7.08 (d, 2H), 5.16 (m, 0.5H), 4.96 (m, 0.5H), 4.16–3.96 (m, 2H), 3.62 (m, 1H), 2.88 (m, 1H), 2.62 (m, 2H), 1.82–1.44 (m, 10H), 1.22 (m, 3H) ppm. ESI-MS m/z 360.3 (M+Na)$^+$.

Example 195h (2R,3S)-2-(3-(4-chlorophenyl)-1-propyl)-3-(2-tetrahydropyranyloxyamino)butanoic Acid To a solution of (3R,4S)-1-(2-tetrahydropyranyloxy)-3-(3-(4-chlorophenyl)-1-propyl)-4-methylazetidin-2-one (360 mg, 1.07 mmol) in dioxane (3.2 mL) is added 1 M aqueous sodium hydroxide (1.6 mL). The solution is stirred at 23° C. for 72 h, then extracted with hexanes (20 mL). The aqueous layer is acidified to pH 3 with saturated aqueous sodium bisulfate solution, and is extracted with two 30 mL portions of EtOAc. The combined organics are washed with saturated aqueous sodium chloride, dried over anhydrous magnesium sulfate, and concentrated under reduced pressure to provide (2R,3S)-2-(3-(4-chlorophenyl)-1-propyl)-3-(2-tetrahydropyranyloxyamino)butanoic acid as an oil (380 mg, 99% yield).

$^1$H NMR (400 MHz, CDCl$_3$) δ 7.22 (d, 2H), 7.06 (d, 2H), 4.92 (m, 0.5H), 4.78 (m, 0.5H), 3.95 (m, 0.5H), 3.86 (m, 0.5H), 3.57 (m, 1H), 3.36 (m, 0.5H), 3.24 (m, 0.5H), 2.94 (m, 0.5H), 2.81 (m, 0.5H), 2.62 (m, 2H), 1.94–1.66 (m, 4H), 1.62–1.44 (m, 6H), 1.24 (m, 1H), 1.08 (d, 1.5H), 1.02 (d, 1.5H) ppm. ESI-MS m/z 3:54.2 (M–H)$^-$.

Example 195i (2R,3S)-2-(3-(4-chlorophenyl)-1-propyl)-3-(formyl-2-tetrahydropyranyloxyamino)butanoic Acid To a solution of (2R,3S)-2-(3-(4-chlorophenyl)-1-propyl)-3-(2-tetrahydropyraiyloxyamino)butanoic acid (380 mg, 1.07 mmol) in pyridine (4 mL) at 0° C. is added formic acetic anhydride (0.9 mL). The resulting solution is allowed to warm to 25° C., stirred for 3 h, and then concentrated to dryness under reduced pressure. The resulting gum is dissolved in EtOAc (30 mL) and washed sequentially with 1 M hydrochloric acid (20 mL) and saturated aqueous sodium chloride solution. The organic layer is dried over anhydrous magnesium sulfate and concentrated under reduced pressure to provide (2R,3S)-2-(3-(4-chlorophenyl)-1-propyl)-3-(formyl-2-tetrahydropyranyloxyamino)butanoic acid as an oil (385 mg, 94% yield). ESI-MS m/z 406.2 (M+Na)$^+$, 382.3 (M–H)$^-$.

Example 195j (2R,3S)-3-(Formyl-2-tetrahydropyranyloxyamino)-2-(3-(4-chlorophenyl)-1-propyl)butanoic Acid [(1S)-2,2-Dimethyl-(1-(3-pyridyl)carbamoyl)-1-propyl] amide To a solution of (2R,3S)-2-(3-(4-chlorophenyl)-1-propyl)-3-(formyl-2-tetrahydropyrariyloxyamino)butanoic acid (400 mg, 1.04 mmol) in DMF (4 mL) is added BOP reagent (507 mg, 1.15 mmol), HOBt ( 155 mg, 1.15 mmol), and NMM (527 mg, 5.22 mmol). After 30 min, addition of (2S)-2-Amino-3,3-dimethylbutanoic acid 3-pyridylamide hydrochloride (447 mg, 1.56 mmol) occurs and the resulting solution is stirred at 25° C. for 72 h. The reaction mixture is poured into EtOAc-hexanes (1:1, 200 mL) and washed sequentially with 1 M aqueous sodium carbonate and saturated aqueous sodium chloride. The organic layer is dried over magnesium sulfate, concentrated in vacuo, and purified by silica gel chromatography (elution with 3:1 EtOAc-hexane) to provide (2R,3S)-3-(Formyl-2-tetrahydropyraiiyloxyamino)-2-(3-(4-chlorophenyl)-1-propyl)butanoic acid [(1S)-2,2-dimethyl-(1-(3-pyridyl)carbamoyl)-1-propyl]amide as a white solid (441 mg, 74% yield). ESI-MS m/z 595.1 (M+Na)+.

Example 195

(2R,3S)-3-(Formylhydroxyamino)-2-(3-(4-chlorophenyl)-1-propyl)butanoic acid [(1S)-2,2-dimethyl-1-(3-pyridyl)carbamoyl)-1-propyl]amide A solution of (2R,3S)-3-(Formyl-2-tetrahydropyranyloxyamino)-2-(3-(4-chlorophenyl)-1-propyl)butanoic acid [(1S)-2,2-dimethyl-(1-(3-pyridyl)carbamoyl)-1-propyl]amide (440 mg, 0.77 mmol) in acetic acid-water (4:1, 2 mL) is heated to 50° C. for 20 h. The reaction mixture is concentrated, then dissolved in toluene and concentrated in vacuo. The procedure is repeated once again to afford the crude product which is triturated from hot dichloromethane-diethyl ether to provide (2R,3S)-3-(formylhydroxyamino)-2-(3-(4-chlorophenyl)-1-propyl)butanoic acid [(1S)-2,2-dimethyl-(1-(3-pyridyl)carbamoyl)-1-propyl]amide as a white solid (297 mg, 79% yield).

$^1$H NMR (400 MHz, $CD_3OD$) δ 8.75 (s, 1H), 8.27 (m, 1H), 8.25 and 7.98 (s, 1H), 8.00 (m, 1H), 7.38 (m, 1H), 6.97 (m, 4H), 4.48 and 3.82 (m, 1H), 4.45 (m, 1H), 2.94 and 2.84 (m, 1H), 2.58 (m, 1H), 2.39 (m, 1H), 1.48 (m, 4H), 1.24 and 1.18 (d, 3H), 1.03 (s, 9H) ppm. ESI-MS m/z 511.3 (M+Na)+.

PHARMACOLOGY

The efficacy of compounds of the present invention as inhibitors of matrix metalloproteases, TNFα converting enzyme and TNFα cellular release can be evaluated and measured using pharmacological methods known in the art or as described in detail below based on similarly established methodologies.

Pharmacological Example 1
A. Matrix Metalloprotease Inhibition Protocol

The potency of compounds of the invention as inhibitors of 19 kD truncated collagenase-1 (MMP-1), 20 kD truncated collagenase-3 (MMP-13), stromelysin-1 (MMP-3), and 50 kD truncated gelatinase B (MMP-9) is determined according to the general procedure of Bickett et. al. (*Anal. Biochem.* 1993, 212, 58–64) using the fluorogenic substrate, DNP-Pro-Cha-Gly-Cys(Me)-His-Ala-Lys(NMA)-$NH_2$ (DNP=2, 4-dinitrophenyl, NMA=N-methylanthranilic acid). Assays are conducted in a total volume of 0.180 mL assay buffer (200 mM NaCl, 50 mM Tris, 5 mM $CaCl_2$, 10 $\mu$M $ZnSO_4$, 0.005% Brij 35, pH 7.6) in each well of a black 96 well microtiter plate. 19 kD collagenase-1, 20 kD collagenase-3, stromelysin-1, and 50 kD gelatinase B concentrations are adjusted to 500 pM, 30 pM, 5 nM, and 100 pM, respectively. A dose response is generated using an eleven-point, 3-fold serial dilution with initial starting test compound concentrations of 100, 10, or 1 $\mu$M. Inhibitor and enzyme reactions are incubated for 30 minutes at ambient temperature and then initiated with 10 $\mu$M fluorogenic substrate (above). The product formation is measured at $Excitation_{343}/Emission_{450}$ nm after 45–180 minutes using a Fluostar SLT fluorescence analyzer. Percent inhibition is calculated at each inhibitor concentration and the data were plotted using standard curve fitting programs. $IC_{50}$ values were determined from these curves. Assays were run at low substrate concentration ($[S]<<K_m$) such that the calculated $IC_{50}$ values are equivalent to $K_i$ within experimental error.

B. TNFα Converting Enzyme Inhibition Protocol

The potency of compounds of the invention as inhibitors of cell-free tumor necrosis factor a converting enzyme is determined as follows; Membrane preparation from Mono-Mac 6 cells (subfractionated extract from equivalent of $6 \times 10^6$ cells per 60 $\mu$l assay) is incubated for 1 h with 200 nM radiolabeled substrate (Biotin-SPLAQAVRSSSRT-($^3$H)P—S—$NH_2$, 4.1 Ci/mmol, ref #0935 from Zeneca) in 10 mM hepes buffer, 250 mM sucrose, pH 7.5. The reaction is quenched by addition of streptavidin SPA beads (Amersham RPNQ0006), with excess binding capacity relative to substrate, suspended in 250 mM EDTA, pH 8.0. Binding is complete within 15 minutes and plates are counted in a Wallac 1450 Microbeta liquid scintillation counter. Percent inhibition is calculated at each inhibitor concentration and the data were plotted using standard curve fitting programs. $IC_{50}$ values were determined from these curves. Assays were run at low substrate concentration ($[S]<<K_m$) such that the calculated $IC_{50}$ values are equivalent to $K_i$ within experimental error.

C. Cell-Based TNFα Release Inhibition Protocol

The potency of compounds of the invention as inhibitors of release of soluble tumor necrosis factor a from stimulated monocytes in vitro is determined as follows; LPS/PMA solution for assay consisting of a) 4 $\mu$L of 5 mg/mL LPS stock and b) 6 $\mu$L of 10 mg/mL PMA stock are added to 500 $\mu$L of medium (RPMI 1640 (Gibco)+10% FBS+penicillin/streptomycin+1-glutamine). This solution is then diluted 1:1000 (40 ng/mL and 120 ng/mL) for use later in the assay. Compounds (10 mM) are serially diluted 1:3 in DMSO. Compound dilutions (20 $\mu$L) are added to a sterile round bottom 96 well plate (20 $\mu$L:200 $\mu$L total volume=1:10 for final concentrations of 50 $\mu$M for test compounds). Mono-Mac 6 cell suspension (130 $\mu$L, $1.5 \times 10^6$ cells/mL) is then added to each well resulting in $2 \times 10^5$ cells/well. LPS/PMA (50 $\mu$L) solution is then added to each well to begin stimulation (final concentrations of 10 ng/mL and 30 ng/mL respectively). The plate is incubated at 37° C. for 2 hours then spun at 1,500 rpm for 3 minutes to pellet cells. The supernatant (120 $\mu$L/well) is removed to a new round bottom 96 well plate and diluted 1:10 in PBS. Then, 20 $\mu$L of the supernatant is transferred to a Cistron TNFα ELISA plate and processed according to the manufacturer's instructions to quantitate levels of TNFα. Percent inhibition of TNFα release is calculated at each inhibitor concentration and the data were plotted using standard curve fitting programs. $IC_{50}$ values were determined from these curves.

Results are listed in Table 3.

TABLE 3

| Example | TNFα Converting Enzyme $K_i$ | Collagenase-1 $K_i$ | Collagenase-3 $K_i$ | Gelatinase B $K_i$ | Stromelysin-1 $K_i$ | TNFα Release Inhibition $IC_{50}$ |
|---|---|---|---|---|---|---|
| Example 1 | +++ | + | + | + | + | nd |
| Example 2 | + | +++ | + | ++ | ++ | ++++ |
| Example 3 | + | ++++ | + | ++ | + | ++ |

TABLE 3-continued

| Example | TNFα Converting Enzyme $K_i$ | Collagenase-1 $K_i$ | Collagenase-3 $K_i$ | Gelatinase B $K_i$ | Stromelysin-1 $K_i$ | TNFα Release Inhibition $IC_{50}$ |
|---|---|---|---|---|---|---|
| Example 4 | + | ++++ | + | ++ | + | + |
| Example 5 | + | +++ | + | + | + | ++ |
| Example 6 | + | ++++ | ++ | ++++ | ++ | ++++ |
| Example 7 | ++ | ++++ | +++ | ++++ | ++++ | ++++ |
| Example 8 | + | ++++ | ++ | ++++ | ++++ | ++++ |
| Example 9 | + | ++++ | +++ | ++++ | ++++ | ++ |
| Example 183 | ++ | ++++ | + | + | ++ | nd |
| Example 195 | ++++ | + | + | + | + | nd |

Key;
+ <100 nM
++ 100 nM–500 nM
+++ 500 nM–1 μM
++++ >1 μM
nd not done

Pharmacological Example 2
Murine LPS—Stimulated Serum TNF Inhibition Protocol

The potency of compounds of the invention as inhibitors of serum TNFα elevation in mice treated with lipopolysaccharide (LPS) is determined as follows; a) for subcutaneous (s.c.) administration, test compound is dissolved in DMSO and added to a mixture of 0.9% sodium chloride solution and 30% Trappsol HPB-20 (Cyclodextrin Technology Development Inc., Gainesville, Fla. USA) for a final DMSO concentration of 1%. The dosing solution is sonicated briefly and 0.2 mL is injected subcutaneously 10 min prior to LPS injection, b) for per oral (p.o.) administration, test compounds are formulated in 0.2 mL of PBS and 0.1% Tween 80 and given orally via gavage 10 min prior to LPS administration.

C3/hen female mice are injected intraperitoneally with 200 μg/kg LPS (*Escherichia coli*, Serotype 0111:B4, Sigma Chemical Co, St. Louis, Mo.) in PBS and sacrificed 90 min later by $CO_2$ asphyxiation. Blood is immediately taken from the caudal vena cava and plasma prepared and frozen at –80° C. Plasma concentrations of TNF are measured by ELISA (Genzyme Co., Cambridge Mass.).

Result,; are listed in Table 4.

TABLE 4

| Compound | Route of Administration | Dose | Percentage Inhibition of Serum TNFα |
|---|---|---|---|
| Example 146 | s.c. | 40 mg/kg | ++ |
| Example 183 | p.o. | 40 mg/kg | ++ |
| Key; | + | 25%–50% | |
| | ++ | 50%–75% | |
| | +++ | >75% | |

Throughout this application, various publications are may be recited. Such publications are hereby incorporated by reference in their entirety.

While the invention has been described and illustrated with reference to certain preferred embodiments thereof, those skilled in the art will appreciate that various changes, modifications and substitutions can be made therein without departing from the spirit and scope of the invention. For example, effective dosages other than the preferred dosages as set forth herein above may be applicable as a consequence of variations in the responsiveness of the mammal being treated for inflammatory conditions, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of the formula

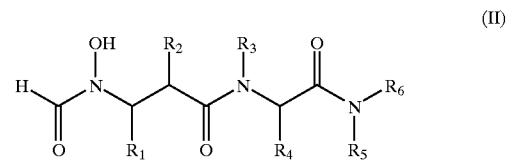

(II)

where $R_1$ is methyl, isopropyl, or n-propyl;

$R_2$ is 5-methylthiophene-2-methyl, 3-phenyl-1-propyl, 3-(thiophene-2-yl)-1-propyl, 3-(4-chlorophenyl)-1-propyl, 3-(4-phenoxyphenyl)-1-propyl, or 5-phenyl-1-pentyl;

$R_3$ is hydrogen;

$R_4$ is tert-butyl;

$R_5$ is hydrogen;

$R_6$ is pyridyl;

or a pharmaceutically acceptable salt, or solvate thereof.

2. A compound selected from:

(2R,3S)-3-(Formyl-hydroxyamino)-2-(3-phenyl-1-propyl)butanoic Acid [(1S)-2,2-Dimethyl-1-(pyridine-3-ylcarbamoyl)-1-propyl]amide;

(2R,3S)-3-(Formyl-hydroxyamino)-2-(3-phenyl-1-propyl)hexanoic Acid [(1S)-2,2-Dimethyl-1-(pyridine-3-ylcarbamoyl)-1-propyl]amide;

(2R,3S-3-(Formyl-hydroxyamino)-2-(5-methyl-2-thiophenemethyl)hexanoic Acid [(1S)-2,2-Dimethyl-1-(pyridine-3-ylcarbamoyl)-1-propyl]amide;

(2R,3S)-3-(Formyl-hydroxyamino)-2-(3-phenyl-1-propyl)-4-methylpentanoic Acid [(1S)-2,2-Dimethyl-1-(pyridine-3-ylcarbamoyl)-1-propyl]amide;

(2R,3S)-3-(Formyl-hydroxyamino)-2-(3-(4-chlorophenyl)-1-propyl)-4-methylpentanoic Acid [(1S)-2,2-Dimethyl-1-(pyridine-3-ylcarbamoyl)-1-propyl]amide;

(2R,3S)-3-(Formyl-hydroxyamino)-2-(3-(thiophene-2-yl)-1-propyl)butanoic Acid [(1S)-2,2-Dimethyl-1-(pyridine-3-ylcarbamoyl)-1-propyl]amide;

(2R,3S)-3-(Formyl-hydroxyamino)-2-(5-phenyl-1-pentyl)butanoic Acid [(1S)-2,2-Dimethyl-1-(pyridine-3-ylcarbamoyl)-1-propyl]amide; and (2R,3S)-3-(Formyl-hydroxyamino)-2-(3-(4-phenoxyphenyl)-1-propyl)butanoic Acid [(1S)-2,2-Dimethyl-1-(pyridine-3-ylcarbamoyl)-1-propyl]amide.

3. A pharmaceutical composition comprising a pharmaceutically acceptable carrier and a pharmacologically effective amount of a compound as claimed in claim 1.

4. A method of inhibiting the intracellular release of tumor necrosis factor alpha, comprising the step of administering to a mammal in need thereof a pharmacologically effective amount of a compound as claimed in claim 1.

5. A method of inhibiting a matrix metalloprotease, comprising the step of administering to a mammal in need thereof a pharmacologically effective amount of a compound as claimed in claim 1.

6. A method of inhibition of shedding of cell surface protein ectodomains, comprising the step of administering to a mammal in need thereof a pharmacologically effective amount of a compound as claimed in claim 1.

7. A method of inhibition of CD23 proteolysis, compromising the step of administering to a mammal in need thereof a pharmocologically effective amount of a compound as claimed in claim 1.

* * * * *

UNITED STATES PATENT AND TRADEMARK OFFICE
CERTIFICATE OF CORRECTION

PATENT NO.    : 6,329,400 B1
DATED         : December 11, 2001
INVENTOR(S)   : Andrews et al.

It is certified that error appears in the above-identified patent and that said Letters Patent is hereby corrected as shown below:

Title page,
Item [75], Inventors, should read:
-- Robert Carl Andrews, Durham;
Michael David Gaul, Apex
Daryl Lynn McDougald, Durham;
David Lee Musso, Raleigh --

Signed and Sealed this

Twenty-second Day of March, 2005

JON W. DUDAS
*Director of the United States Patent and Trademark Office*